US007449342B2

(12) United States Patent
Kane et al.

(10) Patent No.: US 7,449,342 B2
(45) Date of Patent: Nov. 11, 2008

(54) METHODS OF MANIPULATING SMALL AMOUNTS OF SOLIDS

(75) Inventors: Nathan Kane, Arlington, MA (US); Michael Cima, Winchester, MA (US); Javier Gonzalez-Zugasti, N. Billerica, MA (US); Jeanie Cherng, Framingham, MA (US); Anthony Lemmo, Sudbury, MA (US); J. Richard Gyory, Sudbury, MA (US)

(73) Assignee: Transform Pharmaceuticals, Inc., Lexington, MA (US)

( * ) Notice: Subject to any disclaimer, the term of this patent is extended or adjusted under 35 U.S.C. 154(b) by 910 days.

(21) Appl. No.: 10/700,146

(22) Filed: Nov. 3, 2003

(65) Prior Publication Data
US 2004/0146434 A1  Jul. 29, 2004

Related U.S. Application Data

(60) Provisional application No. 60/423,377, filed on Nov. 4, 2002, provisional application No. 60/424,001, filed on Nov. 6, 2002, provisional application No. 60/430,089, filed on Dec. 2, 2002, provisional application No. 60/449,554, filed on Feb. 24, 2003, provisional application No. 60/450,285, filed on Feb. 27, 2003.

(51) Int. Cl.
*G01N 1/10* (2006.01)
*B65H 5/00* (2006.01)

(52) U.S. Cl. .................... 436/180; 221/224; 422/99; 422/100

(58) Field of Classification Search ............... 436/180; 422/99–100; 221/224; 141/12, 71, 73
See application file for complete search history.

(56) References Cited

U.S. PATENT DOCUMENTS

| 4,515,753 | A | * | 5/1985 | Smith et al. ........... 422/102 |
| 4,542,835 | A | * | 9/1985 | Gamberini ............... 222/1 |
| 4,791,060 | A | * | 12/1988 | Chandler ............. 435/287.2 |
| 5,549,144 | A | * | 8/1996 | Dworak et al. ......... 141/146 |

(Continued)

FOREIGN PATENT DOCUMENTS

WO    WO 01/51919    7/2001

(Continued)

OTHER PUBLICATIONS

U.S. Appl. No. 09/628,667, filed Jul. 28, 2000, Putnam et al.

(Continued)

*Primary Examiner*—Brian R. Gordon

(57) ABSTRACT

The invention relates to methods and apparatuses for manipulating small amounts of solids. Specific embodiments of the invention are particularly suited for the automated transfer of small amounts of solids. In one embodiment, a uniform powder bed is lightly compressed into plugs of powder and dispensed. In another embodiment, the solid is placed in a liquid carrier to form a slurry, dispensed, and the liquid component is subsequently removed. In yet another embodiment, solids are manipulated using adhesive surfaces.

3 Claims, 57 Drawing Sheets

U.S. PATENT DOCUMENTS

| | | | |
|---|---|---|---|
| 6,096,156 A | | 8/2000 | Morin et al. |
| 6,221,268 B1 | | 4/2001 | Li et al. |
| 6,284,329 B1 | | 9/2001 | Matienzo et al. |
| 6,432,719 B1 | * | 8/2002 | Vann et al. .................. 436/180 |
| 6,674,022 B2 | | 1/2004 | Fermier et al. |
| 6,686,207 B2 | | 2/2004 | Tupper et al. |
| 6,805,175 B1 | | 10/2004 | Pinkas et al. |
| 6,886,612 B2 | | 5/2005 | Duffield |
| 7,101,510 B2 | * | 9/2006 | Vann et al. .................... 422/99 |
| 7,134,459 B2 | * | 11/2006 | Carlson et al. .............. 141/130 |
| 7,159,740 B2 | * | 1/2007 | Nanthakumar et al. ...... 221/224 |
| 7,179,420 B2 | * | 2/2007 | Hatcher et al. ................. 422/73 |
| 2001/0042317 A1 | * | 11/2001 | Yarborough et al. .......... 34/287 |
| 2002/0015666 A1 | | 2/2002 | Vann et al. |
| 2002/0048610 A1 | | 4/2002 | Cima et al. |
| 2003/0087442 A1 | | 5/2003 | Popa-Burke et al. |
| 2003/0124735 A1 | * | 7/2003 | Nanthakumar et al. ...... 436/180 |
| 2004/0168529 A1 | | 9/2004 | Carlson et al. |
| 2005/0084423 A1 | * | 4/2005 | Zarowitz et al. ............. 422/100 |
| 2005/0145291 A1 | * | 7/2005 | Ede et al. ...................... 141/12 |
| 2005/0265900 A1 | * | 12/2005 | Gard et al. .................. 422/100 |

FOREIGN PATENT DOCUMENTS

WO    WO 03/100390    12/2003

OTHER PUBLICATIONS

Allsopp et al., "Impedance Technique for Measuring Dielectrophoretic Collection of Microbiological Particles," J. Phys. D: Appl. Phys. 32:1066-1074 (1999).

Brown et al., "Evaluation of a Dielectrophoretic Bacterial Counting Technique," Biosensors & Bioelectronics, 14:341-351 (1999) http://www.cell-analysis.com.

Green et al., "Dielectrophoretic Separation of Nano-particles," J. Phys. D: Appl. Phys. 30:L41-44 (1997).

Suehiro et al., "Qualitative Estimation of Biological Cell Concentration Suspended in Aqueous Medium by Using Dielectrophoretic. . .," J. Phys. D: Appl. Phys. 32:2814-2820(1999).

Tupper et al., "Electrostatic Dispensing of Dry Dielectric Materials," Proceedings of the Materials Research Society Symposium (2002).

\* cited by examiner

METHODS OF MANIPULATING SMALL AMOUNTS OF SOLIDS

RELATED APPLICATIONS

This application claims priority under 35 USC 119(e) to U.S. Provisional Application No. 60/423,377, filed Nov. 4, 2002, U.S. Provisional Application No. 60/424,001, filed Nov. 6, 2002, U.S. Provisional Application No. 60/430,089, filed Dec. 2, 2002, U.S. Provisional Application No. 60/449,554, filed Feb. 24, 2003 and U.S. Provisional Application No. 60/450,285, filed Feb. 27, 2003, all of which are incorporated herein by reference in their entireties.

TECHNICAL FIELD OF THE INVENTION

The invention relates to methods and apparatuses for manipulating small amounts of solids. Specific embodiments of the invention are particularly suited for the automated transfer of small amounts of solids.

BACKGROUND OF THE INVENTION

A variety of methods and devices exist for obtaining and dispensing small amounts of liquids that have found use in a variety of applications. However, few methods and devices exist for manipulating small amounts (e.g., less than about 25, 10, 5, or 1 mg) of solids (e.g., powders). In the laboratory, such small amounts of solids are often dispensed by hand using a highly accurate scale. Unfortunately, such methods are not amenable to the rapid or automated manipulation of compounds, as they are tedious, time consuming, and prone to error.

Recently, methods and systems have been disclosed for the preparation and analysis of arrays of samples, each of which can contain very small amounts of one or more compounds. See e.g., International Publication WO01/51919, published on Jul. 19, 2001. In such applications, it is often desirable to rapidly and accurately measure and dispense small amounts of solids. In some circumstances, this can be done by dissolving a compound in a solvent to provide a solution of known concentration, dispensing controlled amounts of that solution using micropipettors, and then evaporating the solvent. In certain applications, however, it is necessary that a solid compound be manipulated in a manner that does not substantially affect its physical form. For example, if the crystallinity of a solid is important, it is desirable to measure and dispense the solid in a manner that does not affect its crystalline form (e.g., its crystal structure and habit). Similarly, if the amorphous nature (e.g., average particle size and distribution of particle sizes) of a solid is important, it is preferred that the methods and devices used to manipulate the solid do not substantially affect that quality. Physical characteristics such as these cannot be controlled using solution-based dispensing techniques.

A need therefore exists for methods and devices that can be used to rapidly and accurately dispense small amounts of solids. A need also exists for methods and devices that can be used to manipulate solids without substantially affecting their form.

SUMMARY OF THE INVENTION

This invention encompasses methods of manipulating (e.g., obtaining, transferring, dispensing, mixing and/or weighing) small amounts of solids (e.g., powders), and apparatuses that can be used in such methods. Particular embodiments of the invention are particularly useful in the high throughput preparation and screening of arrays of compounds and compositions. Specific embodiments of the invention do not substantially affect the form of the solid being manipulated.

One embodiment of the invention encompasses methods and apparatuses for dispensing solids by producing plugs with a controlled amount of a solid material of interest. Specific plugs are formed in a way that does not substantially affect the form of the solid.

Another embodiment of the invention encompasses methods and apparatuses for dispensing solids using slurries. Specific methods of this embodiment do not substantially affect the form of the solid.

Another embodiment of the invention encompasses methods and apparatuses for manipulating solids, wherein particles of the solid are adhered non-electrostatically to an adhesive surface. Specific methods of this embodiment do not substantially affect the form of the solid.

Another embodiment of the invention encompasses methods and apparatuses for transferring the solid content inside one container into another container. Specific methods of this embodiment do not substantially affect the form of the solid.

Another embodiment of the invention encompasses methods and apparatuses for mixing small amounts of solid in a container. Specific methods of this embodiment do not substantially affect the form of the solid.

Another embodiment of the invention encompasses methods and apparatuses for transferring and measuring the mass of small amounts of solid. Specific methods of this embodiment do not substantially affect the form of the solid.

BRIEF DESCRIPTION OF THE FIGURES

Specific embodiments of the invention can be understood with reference to the attached figures, described below.

DEFINITIONS

Figure 1A:
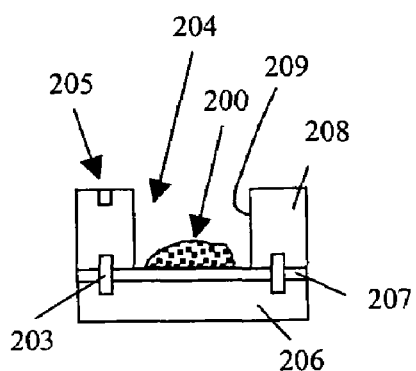
FIG. 1 illustrates a method of forming a uniform powder bed that involves lifting a rotating pin from a packed powder bed.

As used herein and unless otherwise indicated, the term "controlled amount" refers to an amount of a compound that is weighed, aliquotted, or otherwise dispensed in a manner that attempts to control the amount of the compound. Preferably, a controlled amount of a compound differs from a target amount by less than about 30, 20, 10, 5, or 1 percent of the target amount. For example, if a target amount of 100 micrograms is specified for a particular application, a controlled amount for that application would be a mass that is between about 70 micrograms to about 130 micrograms, or about 80 micrograms to about 120 micrograms, or about 90 micrograms to about 110 micrograms, or about 95 micrograms to about 105 micrograms, or about 99 micrograms to about 101 micrograms.

As used herein and unless otherwise indicated, the term "plug" is used to refer to an agglomeration of a solid or solids. Preferred plugs are not compressed, or are compressed under conditions that do not substantially affect the form of the solid or solids.

As used herein and unless otherwise indicated, the terms "form" and "physical form," when used to refer to a solid, mean the physical characteristics of the solid. Such characteristics include, but are not limited to, crystallinity or lack of crystallinity, appearance, texture, and color. For example, a solid may be in the form of a powder comprised of particles having a particular average size or size distribution, shape, or color. A solid may be amorphous, crystalline, or may comprise both amorphous and crystalline components. Further, the form of a crystalline solid includes, but is not limited to, its crystal structure and habit.

As used herein and unless otherwise indicated, the phrase "without substantially affecting the form," when used to refer to the effect of a method, process, or device on a compound, means that the method, process, or device does not materially change the physical form of a majority of the compound. For example, the phrase encompasses methods, processes, and devices that do not affect the form of about 70, 80, 90, 95, or 99 weight percent of a compound. The phrase also encompasses methods, processes, and devices that affect the average particle size or particle size distribution of a powder of a crystalline compound but that do not affect the crystal structure or habit of the crystalline compound.

As used herein and unless otherwise indicated, the term "slurry" refers to a mixture of solid and liquid wherein a substantial portion of the solid (e.g., greater than about 70, 80, 90, 95, or 99 weight percent) is not dissolved in the liquid.

As used herein and unless otherwise indicated, the term "tube" refers to a hollow instrument (e.g., a hollow needle) with an outer wall and a definable cross-sectional area (e.g, a cylinder, a square, or a hexagon) that can be inserted into a bed of powder.

As used herein and unless otherwise indicated, the term "controlled distance" refers to a distance that does not differ substantially from a predetermined distance. Preferably, a controlled distance differs from a predetermined distance by less than about 10, 5, or 1 percent of the predetermined distance. For example, if one were to insert a tube 2 mm into a bed of powder, a controlled distance of insertion would preferably be from about 1.9 mm to about 2.1 mm, from 1.95 mm to about 2.05 mm, or from about 1.99 mm to about 2.01 mm.

DETAILED DESCRIPTION OF THE INVENTION

This invention encompasses methods and apparatuses that can be used to accurately manipulate small amounts (e.g., less than about 25 mg, 10 mg, 5 mg, 1 mg, 750 micrograms, 500 micrograms, 350 micrograms, 250 micrograms, 175 micrograms, 100 micrograms, 75 micrograms, 50 micrograms, 25 micrograms, 15 micrograms, 10 micrograms, 7.5 micrograms, 5 micrograms, 3 micrograms, 1 micrograms, 900 ng, 750 ng, 500 ng, 350 ng, 250 ng, or 100 ng) of solids. Examples of solids include, but are not limited to, pharmaceuticals, excipients, dietary substances, alternative medicines, nutraceuticals, agrochemicals, sensory compounds, the active components of industrial formulations, and the active components of consumer formulations. Solids can be amorphous, crystalline, or mixtures thereof.

A first embodiment of the invention encompasses a method and apparatus for manipulating a solid in the form of a powder by compressing a controlled amount of powder into a plug. Preferably, the amount of compression is sufficient to provide a plug that can be manipulated to a desired degree but which is insufficient to substantially affect the physical form of the solid (e.g., by inducing a loss of crystallinity or polymorphism).

A specific method of this embodiment comprises the steps of: (a) forming a bed of powder of predetermined mass and uniform height; (b) inserting a tube a controlled distance into the bed or completely through the bed to obtain a plug of powder, wherein the tube has an interior that accommodates a means of ejecting materials from within the tube; (c) optionally, compressing the powder within the tube; (d) removing the tube with the plug of powder from the bed; (e) moving the tube over a target location; and (f) ejecting the plug of powder.

Another method of the first embodiment comprises the steps of: (a) forming a bed of powder of predetermined mass and uniform height; (b) inserting a grid with multiple hollow partitions with side walls of sufficient width, length (or diameter) and height to create a desired volume of space (e.g., a grid made of thin blades) a controlled distance into the bed or completely through the bed to obtain multiple plugs of powder; (c) optionally, compressing the powder within each partition of the grid; (d) moving the grid with the powder plugs over a target location; and (e) selectively ejecting a plug of powder into the target.

Another method of the first embodiment comprises the steps of: (a) dispensing a predetermined mass of powder into a source chamber; (b) sealing the source chamber with a plate which holds a smaller chamber of variable depth; (c) applying pressure to the powder in the source chamber; (d) sliding the plate against the powder surface in a patterned motion that exposes the smaller chamber to the powder and fills it with powder; (e) releasing the pressure on the source powder; (f) moving the slide plate with its plug of powder away from the source chamber to a target location; and (g) ejecting the plug of powder from the cavity Another method of the first embodiment comprises the steps of: (a) dispensing a predetermined mass of powder into a source chamber; (b) sealing the chamber with a plate which contains a grid with multiple hollow partitions, with side walls of sufficient width, length (or diameter) and height to create a desired volume of space (e.g., a grid made of thin blades), centered above the source chamber and covered by another solid plate; (c) applying pressure to the powder in the source chamber such that the powder flows into the partitions of the grid; (d) releasing the pressure on the source powder; (e) moving the plate with its plugs of powder away from the source chamber to a target location; and (f) selectively ejecting a plug of powder from the cavity Another embodiment of the invention encompasses a method for manipulating a solid by producing a slurry, which comprises the steps of: (a) blending a controlled amount of the solid with a liquid to provide a slurry; (b) dispensing a controlled amount of the slurry; and (c) removing the liquid to provide an amount of the solid, wherein the amount of the solid is less than about 1 mg. In specific embodiments, the amount of the solid is less than about 25 mg, 10 mg, 5 mg, 1 mg, 750 micrograms, 500 micrograms, 350 micrograms, 250 micrograms, 175 micrograms, 100 micrograms, 75 micrograms, 50 micrograms, 25 micrograms, 15 micrograms, 10 micrograms, 7.5 micrograms, 5 micrograms, 3 micrograms, 1 micrograms, 900 ng, 750 ng, 500 ng, 350 ng, 250 ng, or 100 ng. The liquid vehicle can be selected such that it does not dissolve a substantial portion (e.g., which can be specified as less than 10 percent, 5 percent, 2.5 percent, 1 percent, 0.5 percent, 0.25 percent, 0.1 percent, 0.01 percent or 0.001 percent) of the solid to avoid affecting the solid form.

Another embodiment of the invention encompasses a method and apparatus for manipulating a solid by using adhesive surfaces, which comprises contacting particles of the solid with a surface comprising a plurality of discrete adhesive areas separated by non-adhesive areas. In specific embodiments, the size of the adhesive areas are less than about 1 $cm^2$, 50 $mm^2$, 10 $mm^2$, 1 $mm^2$, or 0.5 $mm^2$. As used herein and unless otherwise indicated, the terms "adhesive surface" and "adhesive area" encompass any surface or area on a surface to which a particular solid can adhere by, for example, chemisorption, chemical bonding interactions (e.g., hydrogen bonding and van der Waals interactions), or adsorption (e.g., as a result of vapor deposition). Adhesive surfaces may be a liquid, semi-solid, or solid. Specific adhesive surfaces may utilize conventional adhesives (e.g., glues or gummy or sticky materials). Suitable adhesives are well known to those of ordinary skill in the art. Examples of specific adhesive materials include, but are not limited to, pressure-sensitive adhesives (PSA's), silicones, and hydrogels. Certain pharmaceutically acceptable excipients may also be used as adhesives. In preferred methods of this embodiment, the form of the solid(s) being manipulated does not substantially change during manipulation.

Another embodiment of the invention encompasses a method and apparatus for transferring the solids content inside one container (e.g., a tube or vial) into another container (e.g., a multi-well plate). A specific method of this embodiment comprises the steps of: (a) accelerating a container that holds a controlled amount of solids through an arc trajectory and (b) halting the motion of the container suddenly when it is located above the receiving container in a downward-facing position, thereby causing the solids to be expelled from the initial container and into the receiving container. Another embodiment comprises the steps of: (a) utilizing a container that holds a controlled amount of solids and that has bottom plate which is removable and (b) removing the bottom plate in order to release the solids into a receiving container positioned below the initial container. Another embodiment comprises the steps of: (a) utilizing a container that holds a controlled amount of solids and that has a gas-permeable bottom plate, (b) inverting the container while applying suction through the bottom plate to retain the solids, and (c) reversing the direction of the gas through the bottom plate to expel the solids into a receiving container positioned below the initial container. Another embodiment comprises the steps of: (a) utilizing a container that holds a controlled amount of solids and that has an internal piston, (b) inverting the container, and (c) actuating the piston through the container to eject the solids into a receiving container positioned below the initial container. Another embodiment comprises the steps of: (a) utilizing a container that holds a controlled amount of solids and (b) placing the container inside a well in a receiving plate that has a two-dimensional array of wells.

Another embodiment of the invention encompasses a method and apparatus for mixing small amounts of solid inside a container (e.g., a tube, vial or a well in a multi-well plate). Mixing achieves intimate particulate contact between the solids such that resulting chemical or physical interactions can be analyzed. A specific method of this embodiment comprises applying gas jets through gas-permeable container walls to mix the contents inside the container. Another embodiment comprises vibrating or rotating the container in various directions, orientations, and speeds to mix its contents. Another embodiment comprises placing a mixing tool such as a bar, ball, blade, or wire inside the container and manipulating the mixing tool by means of an oscillating magnet or rotating drive shaft connected to the tool. Another embodiment comprises compressing the walls of the container to mix the contents of the container. Another embodiment comprises dispensing alternate layers of different solids into a container to achieve interparticle contact between different solids.

Another embodiment of the invention encompasses a method and apparatus to manipulate and weigh small amounts of solids. Measuring the mass of a controlled amount of solids is a necessary step for various chemical assays including crystallization, dissolution, and stability analysis. A specific method of this embodiment comprises an apparatus that rapidly dispenses and weighs controlled amounts of solids in a two-dimensional array format with a conventional microbalance. Another method of this embodiment manipulates and measures the mass of a controlled amount of solids without using a conventional microbalance. The method comprises the steps of: (a) measuring a first mechanical resonant frequency of a transfer device, (b) adhering particles to the transfer device, (c) measuring a second mechanical resonant frequency of the transfer device, (d) determining the mass of the attached particles by comparing the first and second resonant frequencies, and (e) removing the particles from the transfer device. Another method of this embodiment comprises the steps of: (a) adhering particles to a transfer device, (b) measuring a first mechanical resonant frequency of the transfer device, (c) removing the particles from the transfer device, (d) measuring a second mechanical resonant frequency of the transfer device, and (e) determining the mass of the removed particles by comparing the first and second resonant frequencies. In addition, the ability to weigh the transferred solids, can be used to provide real-time feedback to the transfer device. Thus, the parameters that control the transfer device can be adjusted to transfer a desired amount of solids.

Specific methods and apparatuses of the invention do not substantially affect the form of the solid being manipulated. Futhermore, specific methods and apparatuses can be readily adapted for use in the high-throughput preparation of arrays of samples. For example, embodiments of the invention can be incorporated into the methods and systems referred to as FAST® and CRYSTALMAX™. The methods and systems referred to as FAST® are described in U.S. patent application Ser. No. 09/628,667, filed Jul. 28, 2000, the entirety of which is incorporated herein by reference. The methods and systems referred to as CRYSTALMAX™ are described in U.S. patent application Ser. No. 09/756,092, filed Jan. 8, 2001, and International Publication WO01/51919, published on Jul. 19, 2001, both of which are incorporated herein by reference in their entireties.

EXAMPLES

Certain embodiments of the invention, as well as certain novel and unexpected advantages of the invention, are illustrated by the following non-limiting examples.

Example 1

Manipulating Solids by Coring a Plug of Powder From a Powder Bed

Solids, such as those in the form of a powder, can be manipulated using systems and methods described for the present invention. For example, solids in the form of fine powders comprising particles having an average size of less than about 200, 150, 100, 50, 10, 5, 1, 0.1, or 0.01 micrometers can be compressed and dispensed in controlled amounts as plugs without the use of solvents, high pressures, or temperatures that may affect the form of the solids. As will be apparent to those of skill in the art, the particular amount of pressure that can be used to provide such plugs will depend on the particular compound and its form. However, that amount is readily determined using little, if any, routine experimentation. Examples of such pressures include, but are not limited to, less than about 30, 20, 10, 5, or 2 psi. The use of such low pressures typically avoids physical form changes such as loss of crystallinity or conversion to a polymorphic form, which can occur under compression conditions used to make conventional tablets.

In a specific embodiment of this method, a known mass of powder (e.g., less than about 1 gram, 500 mg, 100 mg, 25 mg, 1 mg, 500 micrograms, 250 micrograms, or 100 micrograms) is dispensed into a cylindrical cavity of predetermined diameter and depth. The powder is packed evenly across the base of the cavity using a rotating cylinder that applies a predetermined average pressure to the bed that is less than 30, 20, 10, 5, or 1 psi. Next, a hollow tube (e.g. a cylindrical needle with an inner diameter less than 0.01 mm, 0.1 mm, 0.5 mm, 1 mm, 2 mm, 3 mm, 5 mm or 10 mm) with a predetermined cross sectional area is used to core a plug of the powder. The tube, which can be of any shape so long as the volume of the resulting plug can be determined, is inserted a controlled distance into the powder bed to obtain a plug of predictable size. Preferably, the tube is inserted all the way through the powder bed. Reproducible packing inside the tube can result from specific ratios of height to diameter of the coring cavity, for example, a 1:1 height to diameter ratio is effective. The plug is then optionally compressed, as discussed below, and the tube, which still contains the plug, is removed from the powder bed and positioned over a receptacle (e.g., a tube, vial or a well in a multi-well plate). To prevent the bed from breaking apart during punching, a grill (i.e. a thin plate with an array of holes) that the tube can pass through may be placed over the bed prior to punching. The plug is then ejected from the tube using, for example, compressed gas, a liquid in which the solid is soluble, sparingly soluble, or insoluble, vibration of the tube, or mechanical means, such as a piston located within the tube.

Figure 1B:
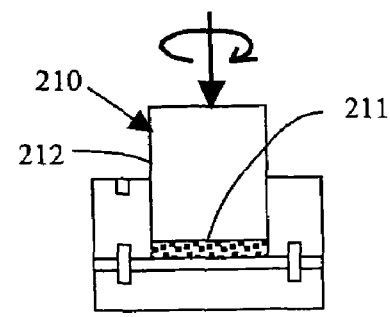
Figure 1C:
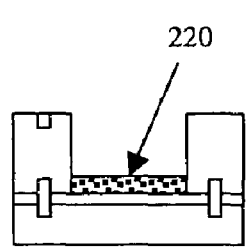
Figure 1D:
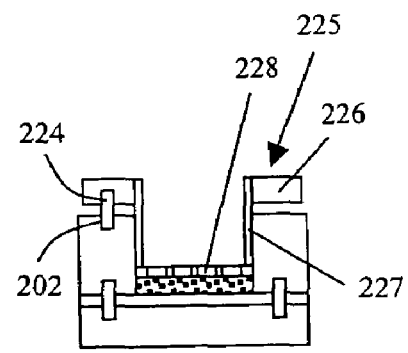
Figure 2:
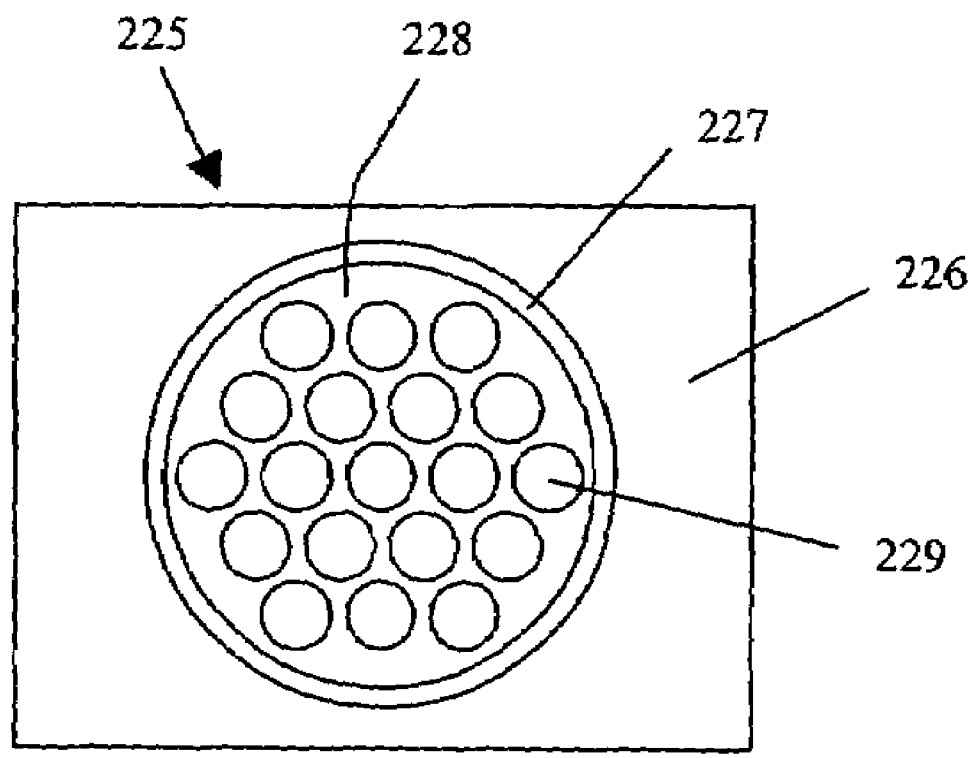
FIG. 2 illustrates a top view of a grille that is placed on top of the uniform powder bed that is produced via the method shown in FIG. 1.

FIGS. 1A through 1D illustrate a method and apparatus for uniform powder bed preparation. A predetermined weight of powder 200 is placed in a cavity (e.g., hollow cylinder) 204 in source receptacle assembly 205, as shown in FIG. 1A. Source receptacle assembly 205 comprises top block 208 with cavity 204 in its interior, strike plate 207, and base 206. Then, as shown in FIG. 1B, rod 210 (preferably cylindrical) is inserted through cavity 204 and pressed into powder 200 with a predetermined force, which results in a powder bed pressure typically in the range of about 0.5 psi to about 30 psi. Cylindrical rod 210 is then rotated through an angle of typically 90 degrees in either direction with pressure applied. Cylindrical rod 210 is then rotated and pulled out (normally rotated and pulled out simultaneously) of cavity 204. The result is powder bed 220 shown in FIG. 1C with a uniform thickness. Next, grille tube 227 of grille assembly 225 is inserted into cavity 204 so that grille plate 228 contacts the top of powder bed 220, and so alignment pin 224 passes into alignment hole 202, as shown in FIG. 1D. FIG. 1D and FIG. 2 shows a cross sectional side view and a top view, respectively, of grille assembly 225, which comprises tube support 226, thin walled tube 227, grille plate 228 and alignment pin 224. As shown in FIG. 2, grille plate 228 includes a closely packed array of equally sized holes 229 that cover the powder bed.

Top block 208 and cylinder (or pin) 210 are preferably made from a corrosion resistant material that is harder than the powders that are processed. For many powders, a suitable material is unhardened stainless steel type 316. For very hard powders, a suitable material is case hardened stainless steel type 440C that is coated with a hard ceramic thin film, such as sapphire coating type MH provided by Surface Conversion Sciences Corporation in State College, Pa., USA. A suitable material for bottom plate 206 is unhardened stainless steel type 316, or a stainless steel grade with similar corrosion resistance.

The material for strike plate 207 should be softer than the coring tool tip if the tip contacts it (e.g., when tip is inserted completely through the packed bed), so as not to blunt the tool. The strike plate should be chosen so that powder bed 220 will preferably cling to it when pin 210 is removed, while also allowing a punched plug to be cleanly lifted off. For a given powder, bed packing tests should be conducted with different strike plate materials to find one that meets these latter two criteria. Suitable strike plate materials for pharmaceutical powders include, but are not limited to: aluminum, copper, polycarbonate, acrylic, polyester, polystyrene, and PVC. To facilitate a clean release, a thin anti-stick material such as Teflon, UHMW, or wax paper can be adhered to pin face 211. For a given powder, bed packing tests should be performed to determine if these materials cling to the powder enough to mix the powder when pin 210 is rotated and thus create an even pack, while at the same time cleanly releasing when pin 210 is pulled out.

Suitable diameters for cavity 204 range from 2 mm to 50 mm depending on how much powder is available and how well it packs. Other sizes can also be used. Pinwall 212, pinface 211, and cavity wall 209 should preferably be ground and polished to a surface finish of 0.5 micrometers or less to minimize powder adhesion and thus waste. Pin 210 and cavity 204 preferably should be honed or ground to a roundness of under 7.5 micrometers and should be sized so the clearance between them is under 20 micrometers, to minimize intrusion of powder particles. Pin face 211 should deviate from a perfectly flat and perpendicular face by no more than 10 micrometers to produce a flat powder bed, and base 206 should be ground flat to within 10 micrometers. Strike plate 207 should be flat to within 10 micrometers in the region that contacts powder 200 to insure a flat powder bed.

A suitable material for grille plate 228 is 0.2 mm thick full hard Invar, and a suitable method for cutting the outer contour and holes such as hole 229, which typically range in diameter from 0.5 mm to 4 mm, is precision laser cutting which provides +/−5 micrometer accuracy. Custom laser cut Invar grille plates can be fabricated and supplied to these specifications by Photo Etch Technology Company, 71 Willie St, Lowell, Mass. 01854, USA. Suitable materials for thin walled tube 227 and tube support 226 are stainless steel type 316. Tube 227 preferably has a wall thickness of less than 0.4 mm to maximize the punched area.

Figure 3A:
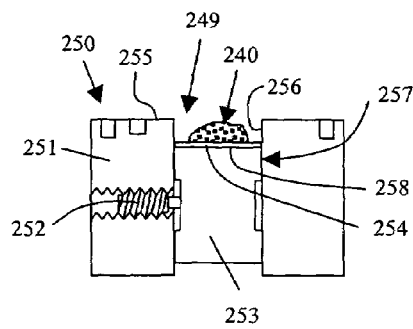
FIG. 3 illustrates a method of forming a uniform powder bed that involves sliding a plate off of a packed powder bed.
Figure 3B:
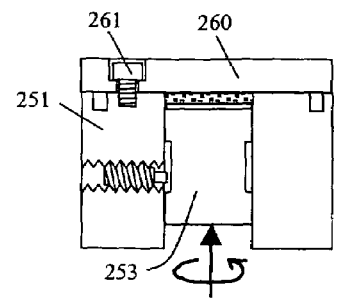
Figure 3C:
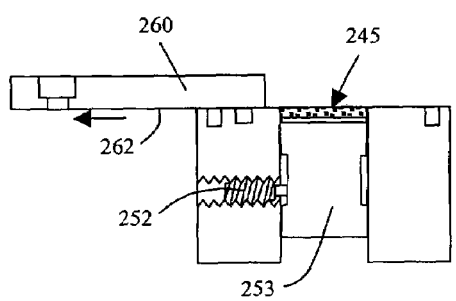
Figure 3D:
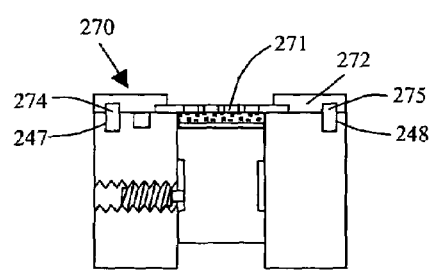
Figure 4:
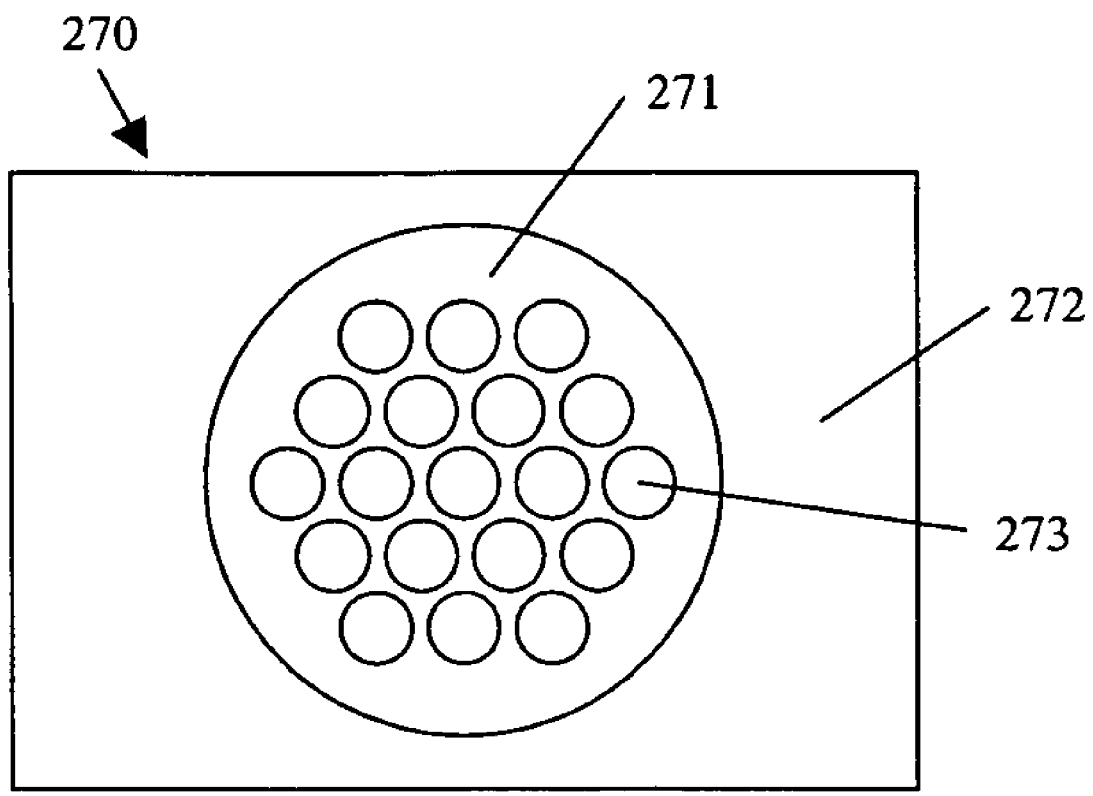
FIG. 4 illustrates a top view of a grille that is placed on top of the uniform powder bed that is produced via the method shown in FIG. 3.

FIGS. 3A through 3D illustrate another method and apparatus for uniform powder bed preparation. A predetermined weight of powder 240 is placed in cavity, typically hollow cylinder 249, of source receptacle assembly 250, as shown in FIG. 3A. Source receptacle assembly 250 comprises block 251 with interior cavity 249, cylinder 253, strike plate 254, and set screw 252. As shown in FIG. 3B, slide plate 260 is affixed on top of block 251 with screw 261. Then a predetermined force which results in a powder bed pressure typically in the range of about 0.5 psi to about 30 psi is applied to cylinder 253. Cylinder 253 is then rotated through an angle of typically 90 degrees in either direction with the pressure applied. Then, as shown in FIG. 3C, set screw 252 is locked against cylinder 253. Then, with screw 261 removed, slide plate 260 is lifted or slid off of powder bed surface 245 while remaining in sliding contact with block surface 255. Next, as shown in FIG. 3D, grille assembly 270 is placed on block surface 255 so that alignment pins 274 and 275 fit into holes 247 and 248 to provide alignment over powder bed 245. FIG. 3D and FIG. 4 show a cross sectional side view and a top view, respectively, of grille assembly 270, which includes grille frame 272, grille plate 271, and alignment pins 274 and 275. As shown in FIG. 4, grille plate 271 comprises a closely packed array of equally sized holes such as hole 273 that cover the powder bed area.

Block 251, cylinder 253, and slide plate 260 are preferably made from a corrosion resistant material that is harder than the powders that are processed. For many powders, a suitable material is unhardened stainless steel type 316. For very hard powders, a suitable material is case hardened stainless steel type 440C that is coated with a hard ceramic thin film, such as sapphire coating type MH provided by Surface Conversion Sciences Corporation in State College, Pa., USA.

The material for strike plate 254 should be softer than the coring tool tip that will contact it, so as not to blunt the tool, and it should be chosen so that powder bed 245 will preferably cling to strike plate 254 when slide plate 260 is removed, while also allowing a punched plug to be cleanly lifted off. For a given powder, bed packing and punch tests must be conducted with different strike plate materials to find one that meets these latter two criteria. The embodiment shown in FIGS. 3A to 3D has the advantage over the embodiment shown in FIGS. 1A to 1D that the sliding action releases a cleaner powder bed surface with a greater variety of powders, including very sticky powders with a low pack density, than the pin lifting method does. Suitable materials for strike plate 254 for use with pharmaceutical powders include, but are not limited to, aluminum, copper, polycarbonate, acrylic, polyester, polystyrene, and PVC. Strike plate 254 is preferably adhered to cylinder 253 with a thin layer (less than 25 micrometers thick) of 5 minute or faster setting epoxy. To facilitate a clean release from powder bed 245, a thin anti-stick material such as Teflon, UHMW, or wax paper can be adhered to slide plate surface 262. Alternately, an assortment of slide plates can be provided with a variety of coatings on surface 262. For a given powder, bed packing tests should be performed to determine if strike plate 254 and slide plate surface 262 cling to powder bed 245 enough so that when cylinder 253 is rotated the powder bed 245 is sheared and mixed thoroughly and thus is packed uniformly, while at the same time allowing for a clean release when slide plate 260 is slid off.

Suitable diameters for cavity 249 range from 2 mm to 50 mm depending on how much powder is available and how well it packs. Other diameters can also be used. Cavity wall 256, block face 255, cylinder wall 257, slide plate surface 262 and block face 255 preferably should be ground and polished to a surface finish of 0.5 micrometers or less to minimize powder adhesion and thus waste. Cylinder 253 and cavity 249 should be ground to a roundness of under 7.5 micrometers and should be sized so the clearance between them is under 20 micrometers. Cylinder face 258 should deviate from a perfectly flat and perpendicular face by no more than 10 micrometers, and slide plate surface 262 and block face 255 should be ground flat to within 5 micrometers. Strike plate 254 should be flat to within 10 micrometers.

A suitable material for grille plate 271 is 0.2 mm thick full hard Invar, and a suitable method for cutting the outer contour and the holes such as hole 273, which range in diameter from 0.5 mm to 4 mm, is precision laser cutting which provides +/−5 micrometer accuracy. Custom laser cut Invar grille plates can be fabricated to these specifications by Photo Etch Technology Company, 71 Willie St, Lowell, Mass. 01854, USA. A suitable material for grille frame 272 is stainless steel type 316.

Figure 5:
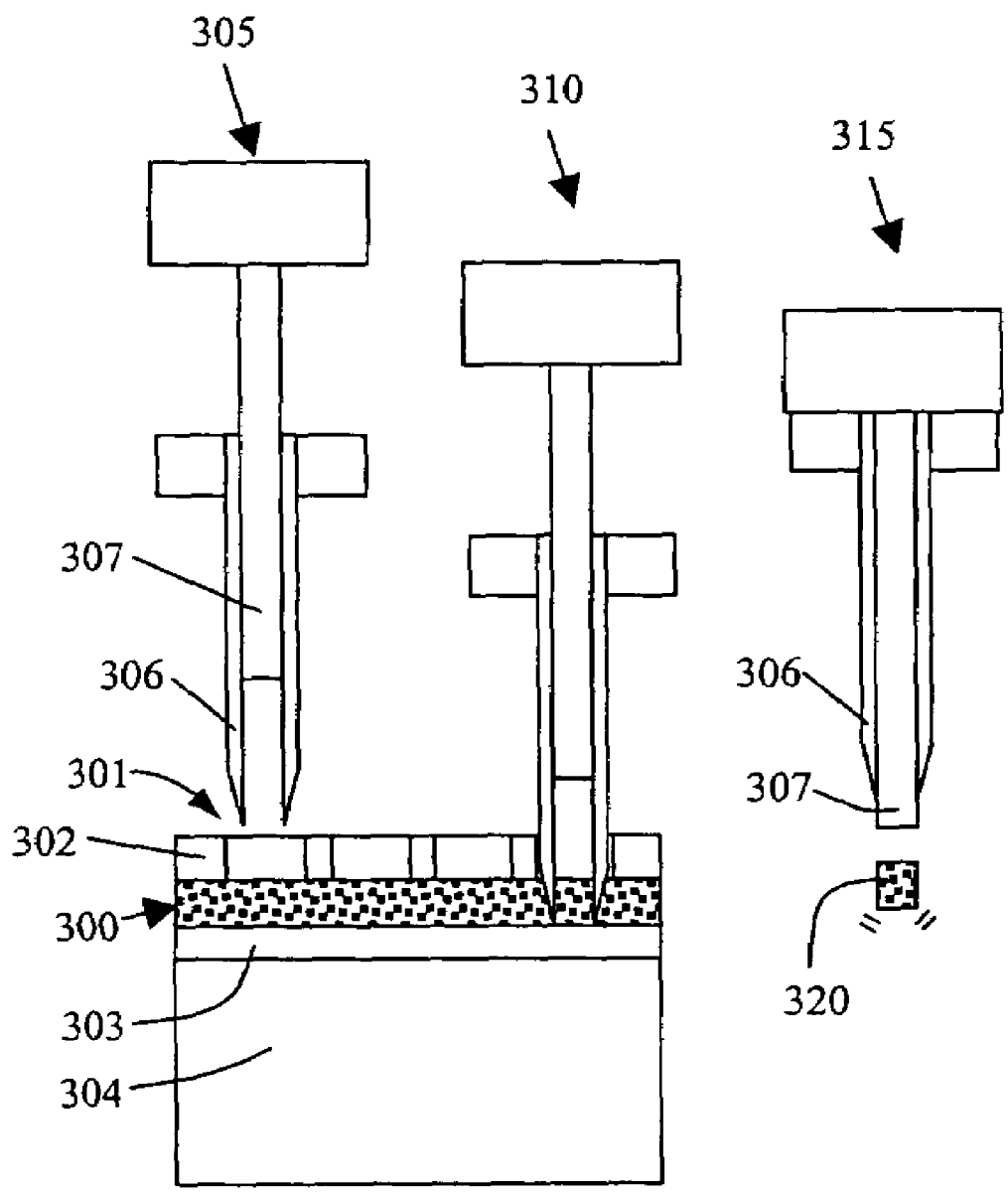
FIG. 5 illustrates a method of creating and dispensing a plug of powder that involves inserting a tube completely through a powder bed, lifting, and then ejecting.

FIG. 5 illustrates a specific method of fabricating a plug from a uniform powder bed. Coring tool 305, which comprises a tube 306 and means of ejecting the plug of powder, e.g. a piston 307, is positioned above hole 301 in grille 302. Next, as shown in view 310, tube 306 is pushed partially through the powder bed or completely through powder bed 300 until it contacts strike plate 303 on base 304. Next, coring tool 305 is lifted and moved to a target location, as shown in view 315, and a plug 320 is ejected out of tube 306 via means of ejecting the plug of powder, e.g. a piston 307, liquid, compressed gas, vibration, etc. This process can be performed without using grille 302; however, for some powders the bed can break apart and portions can stick to the sides of the coring tube, causing large plug mass variation.

With the mass of the powder and the area of the cavity base predetermined, it is possible to calculate the average mass of powder per unit area, W. If, as in this example, the tube is circular and the tube is inserted all the way through the powder bed, then the mass of the plug is given by (1):

$$\text{Powder plug mass} = \pi (d/2)^2 W \qquad (1)$$

where d is the inner diameter of the tube and W is the mass per unit area of the powder bed. Similar relationships for square, hexagonal, and other tube shapes are well known to those skilled in the art. Thus, controlling the shape or interior volume of the tube controls the mass of the plug.

Figure 6:
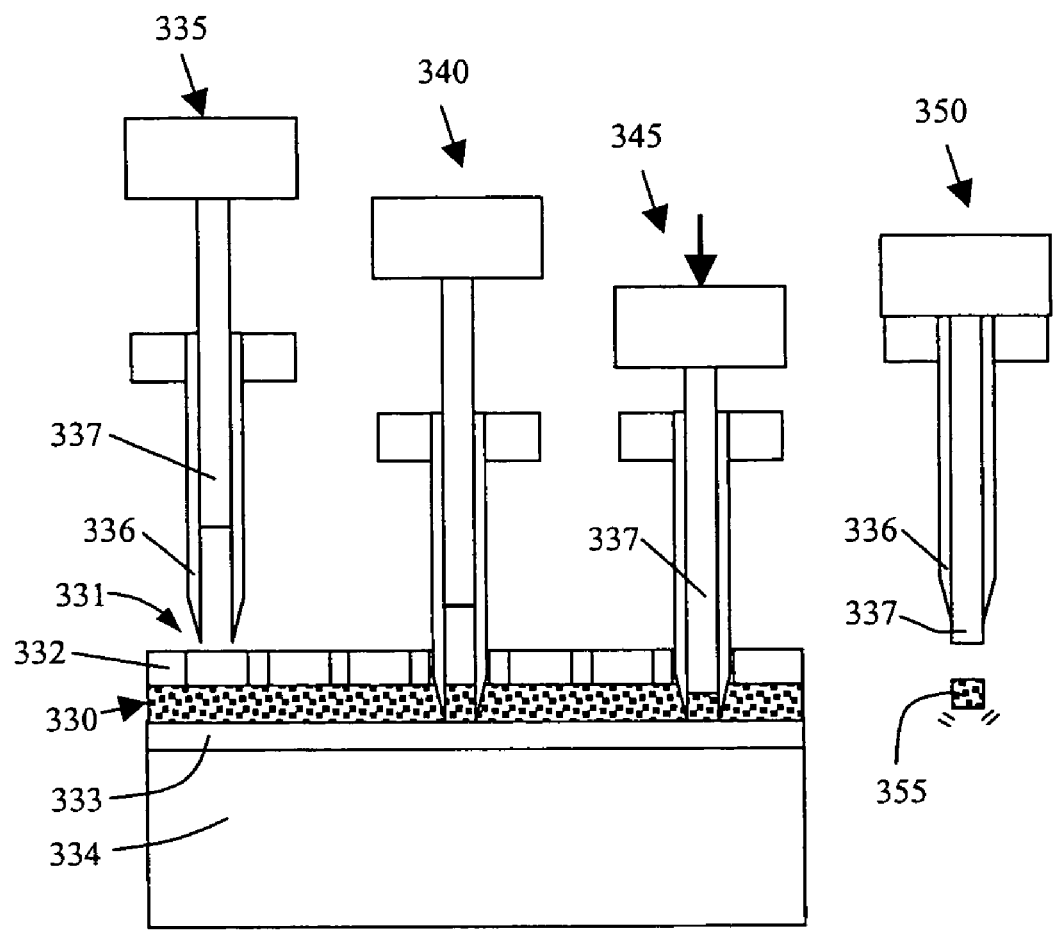
FIG. 6 illustrates a method of creating and dispensing a plug of powder that involves inserting a tube completely through a powder bed, compressing the plug, lifting, and then ejecting.

Plugs of powder may be lifted from the powder bed by simply removing the tube from the bed if the inner diameter of the tube is sufficiently small. For some solids and tube inner diameters, the plug may need to be compacted in order to adhere to the tube interior sufficiently to be lifted. FIG. 6 illustrates a specific method of fabricating and lifting a compacted plug from a uniform powder bed. Coring tool 335, which comprises a tube 336 and means of ejecting the plug of powder, e.g., a piston 337, is positioned above hole 331 in grille 332. As shown in the next view of coring tool 340, tube 336 is pushed through powder bed 330 until it contacts strike plate 333 on base 334. Next, as shown in view 345, piston 337 is pushed into powder bed 330 with a force sufficient to create a pressure in the range of about 5 to about 5000 psi. Next, coring tool 335 is lifted and moved to a target location, and, as shown in view 350, a compacted plug 355 is ejected out of tube 336 via means of ejecting the plug of powder, e.g., a piston or pin 337. This process can be performed without using grille 332, however for some powders the bed can break apart and portions can stick to the sides of the coring tube, causing large plug mass variation.

Figure 7:
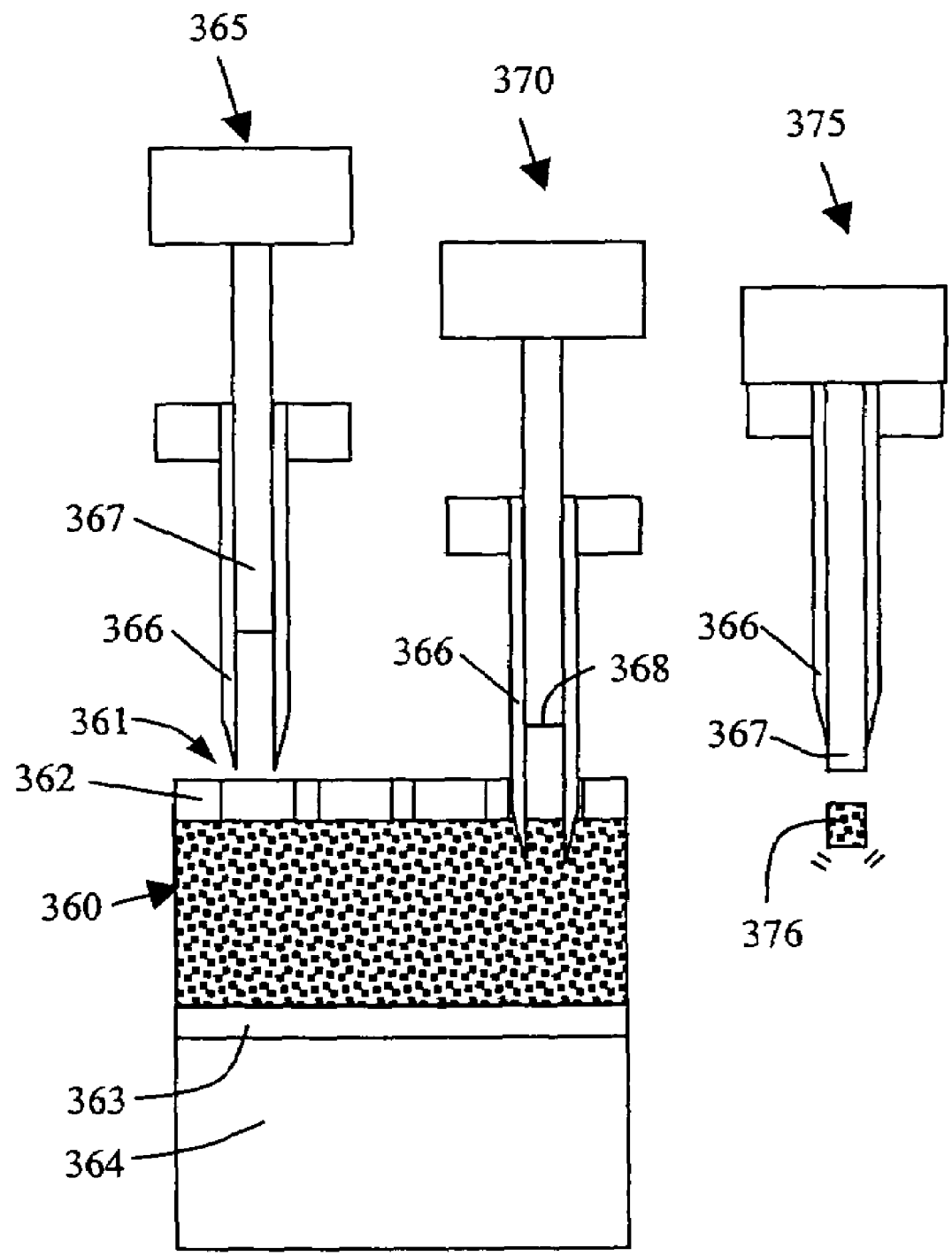
FIG. 7 illustrates a method of creating and dispensing a plug of powder that involves inserting a tube part way through a powder bed, lifting, and then ejecting.

Some powders will have properties that allow a plug with a controlled amount of mass to be produced from a thick bed that is punched multiple times in one place. This is desirable because it increases the number of punches that can be produced from a single packed bed. FIG. 7 illustrates a specific method of fabricating a plug from a uniform powder bed that is taller than the plugs produced. Coring tool 365, which comprises a tube 366 and means of ejecting the plug of powder, e.g., a piston or pin 367, is positioned above hole 361 in grille 362. As shown in the next view of coring tool 370, tube 366 is pushed into powder bed 360 either with a predetermined force, or a predetermined distance. Next, coring tool 365 is lifted and moved to a target location, as shown in view 375, and a plug 376 is ejected out of tube 366 via means of ejecting the plug of powder, e.g., a piston or pin 367. This process can be performed without using grille 362; however, for some powders the bed can break apart and portions can stick to the sides of the coring tool, causing large plug mass variation.

Figure 8:
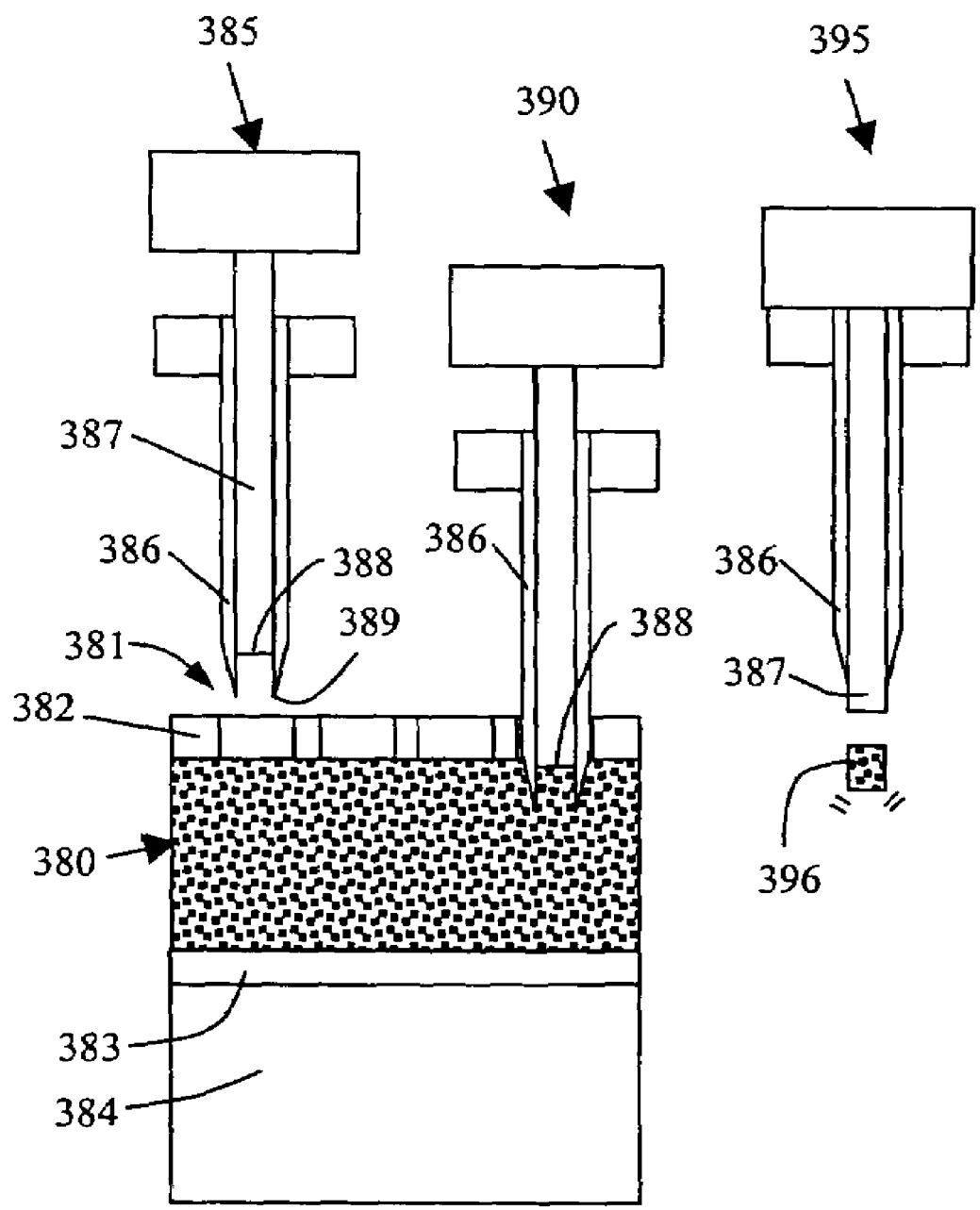
FIG. 8 illustrates a method of creating and dispensing a plug of powder that involves inserting a tube part way through a powder bed with the ejector piston held stationary at a predetermined height relative to the tube, lifting, and then ejecting.

FIG. 8 illustrates another specific method of fabricating a plug from a uniform powder bed that is taller than the plugs produced. Coring tool 385, which comprises a tube 386 and means of ejecting the plug of powder, e.g. a piston or pin 387, is positioned above hole 381 in grille 382. Pin 387 is held stationary to tube 386 so that the distance between piston face 388 and tube edge 389 remains at a fixed and specified value during punching. As shown in the next view of coring tool 390, tube 386 is pushed into powder bed 380 either with a predetermined force, or a predetermined distance. Next, coring tool 385 is lifted and moved to a target location, and, as shown in view 395, a plug 396 is ejected out of tube 386 via means of ejecting the plug of powder, e.g. a piston 387. This process can be performed without using grille 382; however, for some powders the bed can break apart and portions can stick to the sides of the coring tool, causing large plug mass variation.

Commercially available coring tools that are intended for tissue sampling purposes can be used as punching tools for the present invention. A supplier of suitable coring tools for the present invention is Fine Science Tools Inc., 202-277 Mountain Highway, North Vancouver, BC V7J 3P2, Canada, which supplies punching tools with inner tube diameters of 0.35 mm, 0.5 mm, 0.8 mm, 1 mm, 2 mm, 3 mm, and 5 mm. These coring tools include a hardened stainless steel tube and an ejector pin which fits with less than 10 micrometers of clearance. The outside wall of the tube and ejector pin is chrome plated to reduce surface energy so cored materials are less prone to stick. For creating plugs from very hard powders, a custom tungsten carbide tube and pin assembly is appropriate. A tungsten carbide tube and close fitting pin can be manufactured with sufficient precision by Bird Precision, One Spruce Street, Waltham Mass., 02454-0569, USA.

Figure 9:
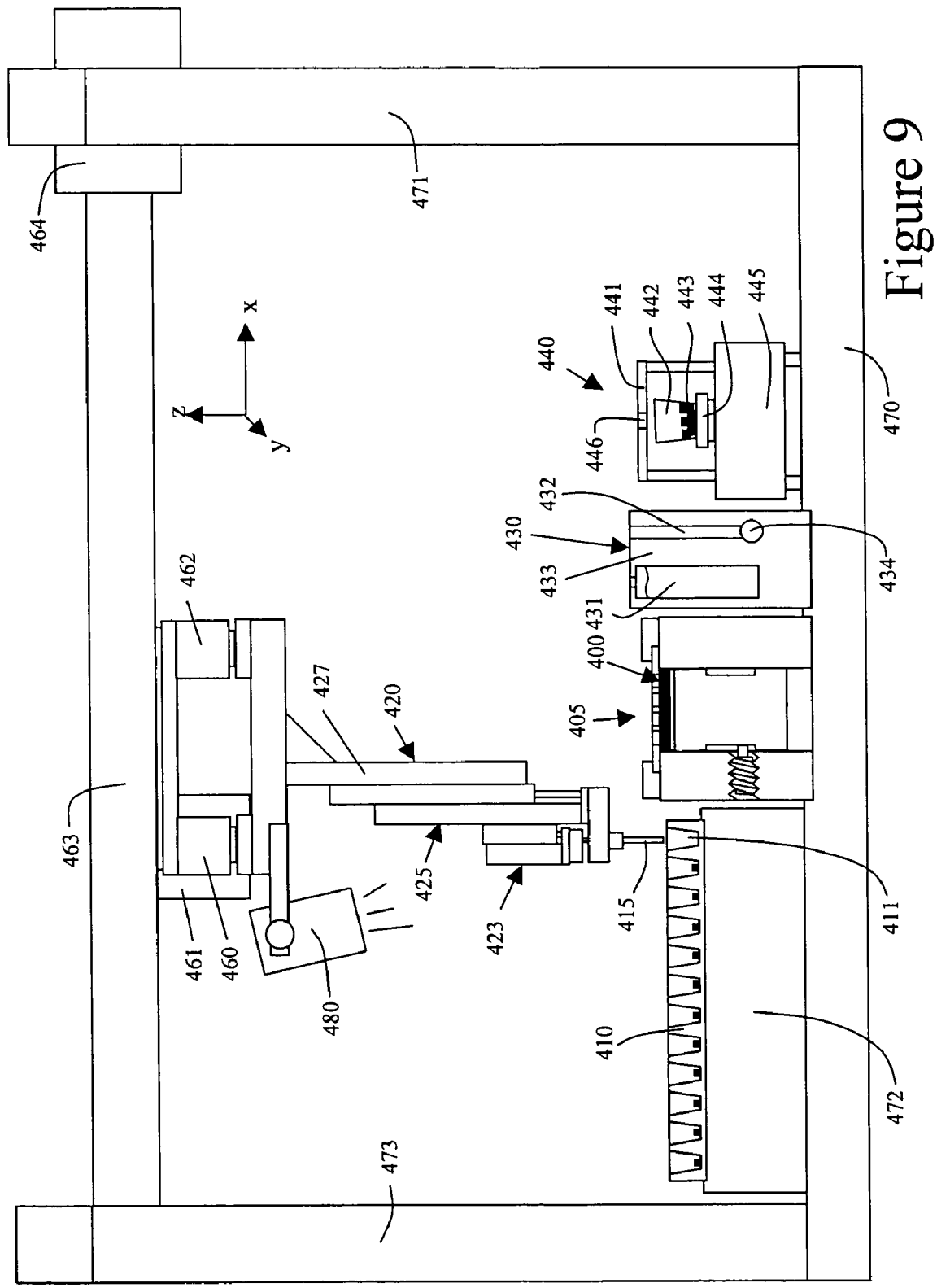
FIG. 9 illustrates a specific apparatus to punch and dispense plugs of solids which includes a punching assembly, x and y linear servos, a receiving plate, a source receptacle assembly, a wash station, a weigh station and a supporting base and frame.

FIG. 9 depicts a specific apparatus for manipulating a solid according to the previously described methods. Punching assembly 420, comprising tube actuator 425, pin actuator 423, coring tool 415, and mounting plate 427, is mounted to y linear actuator 460 and y guide rail 462, which are mounted to x linear actuator 463. Tube actuator 425 and pin actuator 423 together allow a plug to be punched, compressed if desired, and ejected. X linear actuator 463 and y linear actuator 460 has sufficient range to move coring tool 415 over four stations: receiving plate 410, source receptacle assembly 405, wash station 430, and weigh station 440, each with the following functions. Receiving plate 410 is where production plugs are dispensed; source receptacle assembly 405 is where plugs are punched; wash station 430 is where the tip of coring tool or tube 415 can be washed and dried; and weigh station 440 is where plugs can be weighed to characterize and monitor the dispense process. These components are supported by a machine base 470, a receiving plate pedestal 472, and actuator supports 471 and 473.

A suitable x linear actuator 463 is model ERB50-B02LA90-GSS600-A with a 600 mm stroke, a suitable y linear actuator 460 and guide rail 462 are models ERB32-B08LA90-FSS300-A and ERB32-IDLS-FSS300 model with 300 mm strokes, made by Parker Hannifin Corporation based in 6035 Parkland Boulevard Cleveland, Ohio 44124-4141, USA. A suitable product for x servo motor 464 and y servo motor 461 is motor model number NTE-207-CONS-000 by EMERSON, to be used in conjunction with servo drive model Ei-DN-20200-000, also manufactured by EMERSON (8000 West Florissant Avenue, St. Louis, Mo. 63136-8506, USA). Movement commands can be sent to the servo drives from a personal computer programmed with compatible driver software. Products that can be used for tube actuator 425 and pin actuator 423 are pneumatic actuator models MXS8-75A-F9PVL and MXS8-10A-F9PVL respectively, supplied by SMC Corporation of America, 3011 North Franklin Road, Indianapolis, Ind. 46226, USA.

Wash station 430 comprises receptacle 433 with solvent reservoir 431 and drying hole 432. Solvent reservoir 431 is filled with a solvent capable of dissolving powder 400, and the bottom of drying hole 432 is connected to port 434 which is held under vacuum. Suitable solvents for typical powders include, but are not limited to, ethanol, methanol, acetone, ethyl acetate, dimethylsulfoxide, or methylene chloride. An appropriate material for wash receptacle 433 is TEFLON (DuPont) or UHMW polymer (Crown Plastics), which are inert to most useful solvents. To wash and dry, coring tool 415 is first inserted into solvent reservoir 431 for a fixed period of time, and then into drying hole 432 for a fixed period of time. To agitate fluid at the tip and thus speed up washing and drying, pin actuator 423 can be extended and retracted while being washed or dried.

Weigh station 440 comprises microbalance 445 with weighing platform 444, draft shield 441, and weigh cup 442 to contain sample plugs 443. To weigh a plug, coring tool 415 is moved over hole 446 and extended into weigh cup 442, and a plug is ejected into the weigh cup. To allow the microbalance to settle to sufficient accuracy it may be necessary for all actuators to stop moving. The weigh station can be used to weigh a population of plugs to characterize a powder bed packed with predetermined conditions. To characterize a powder bed, typically 40 pellets are randomly sampled from the bed to obtain an average mass and a standard deviation. If the values are acceptable, subsequent beds are packed under the same conditions and production pellets are produced. A suitable microbalance for weighing plugs in the range from 1 microgram to 2 grams with an accuracy of +/−0.25 micrograms is microbalance model UMX2, manufactured by Mettler Toledo, GmbH, with corporate headquarters in Im Langacher, 8606 Greifensee, Switzerland.

To punch a plug, tube actuator 425 is retracted, coring tool 415 is moved over a grille hole in source receptacle assembly 405, tube actuator 425 is extended to push coring tool 415 through a grille hole into powder bed 400, and then actuator 425 is retracted. To eject a plug, coring tool 415 is moved to a target location, tube actuator 425 is extended, pin actuator 423 is extended to eject a plug, then actuator 423 is retracted and actuator 425 is retracted.

To reduce static electricity buildup ion blower 480 is mounted above coring tool 415 and blows ionized air onto the components below it. A suitable ion blower is model 4165 made by NRD LLC, 2937 Alt Blvd, PO Box 310, Grand Island, N.Y. 14072, USA.

Example 2

Manipulating Solids by Extruding a Plug of Powder

This example illustrates an alternative method and apparatus to produce a plug of powder. The average particle size of the powder should be less than about 200, 100, 50, 10, 5, 1, 0.1, or 0.01 micrometers. This embodiment has two significant advantages over the method described in Example 1. It requires less time and labor since a uniform powder bed does not have to be prepared, and secondly, it requires less powder to create the same number of plugs. In other words, this embodiment may prove to be more efficient and less wasteful than coring a plug of powder.

Figure 10A:
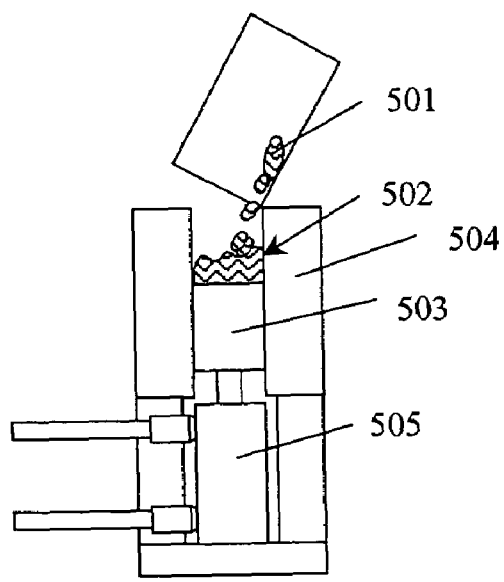
FIG. 10 illustrates a method of extruding powder from a source chamber into a dose chamber to create a plug of powder.

In a specific embodiment of this method and apparatus, plugs of powder are fabricated via the following process. First, as shown in FIG. 10A, a known mass of powder 501 (e.g., less than about 1 gram, 500 mg, 100 mg, 25 mg, 1 mg, 500 micrograms, 250 micrograms, or 100 micrograms) is dispensed into a cylindrical source chamber 502 with source piston 503 located in a downward position. Source block 504 is then clamped to slide plate 506 by keeper plate 509, as shown in FIG. 10B.

Figure 10B:
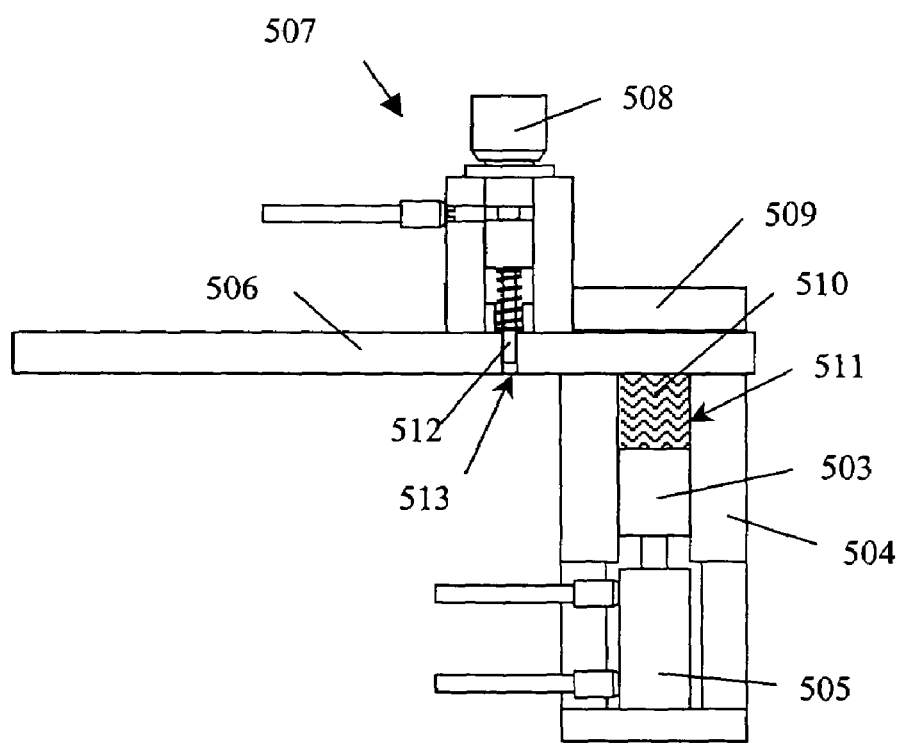
Figure 10C:
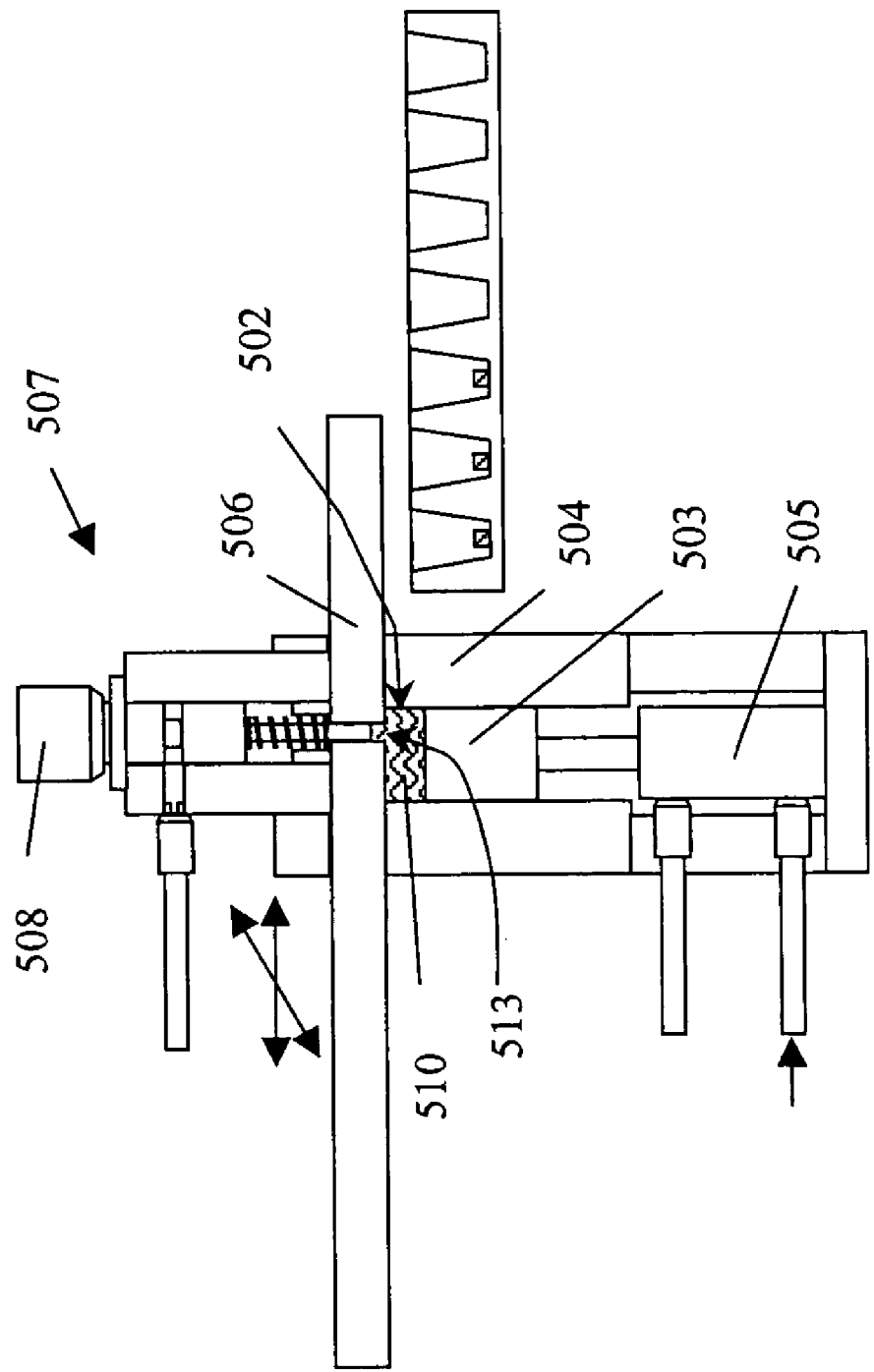
Figure 11A:
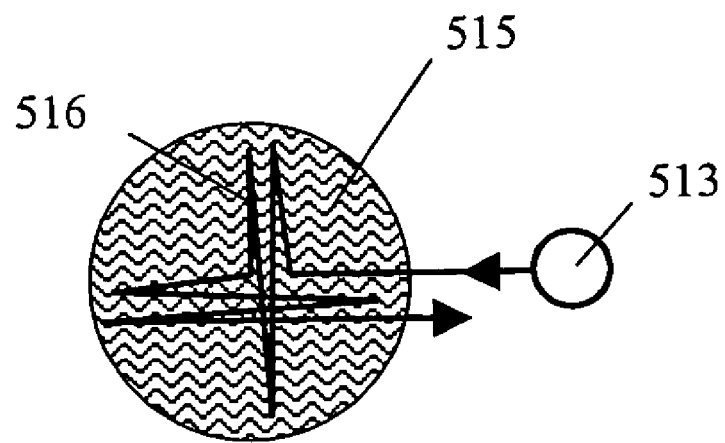
FIG. 11 illustrates examples of trajectories for moving and filling the dose chamber above the powder surface.
Figure 11B:
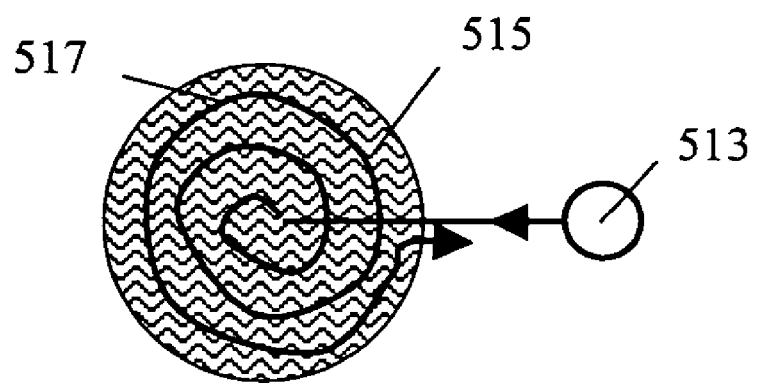

Next, as shown in FIG. 10C, pneumatic cylinder 505, or other means of moving the piston head closer to the slide plate 506, presses source piston 503 with typically about 5 to about 50 psi of pressure and as such, powder 510 against slide plate 506. Slide plate 506 is then moved so dose chamber 513 traverses over the powder surface 515, for example, in a criss-cross trajectory 516 as shown in FIG. 11A. Alternatively, other trajectories such as a spiral trajectory 517 as shown in FIG. 11B can be employed. As a guideline, the traversed distance should be greater than ten times the source chamber diameter, and the path should cover different portions of the source area 515 to achieve repeatable filling of dose chamber 513. To improve the flow of powder 510 into the dose chamber 513, the powder in the source chamber can be subjected to vibration or mixing.

The size and mass of the plug can be changed by adjusting the height of the dose chamber 513 with micrometer device 508 shown in FIG. 10B. Preferably, the ratio of the height to the diameter of dose chamber 513 is greater than 0.2 and less than 0.8, otherwise a different diameter dose chamber should be installed.

Figure 12A:
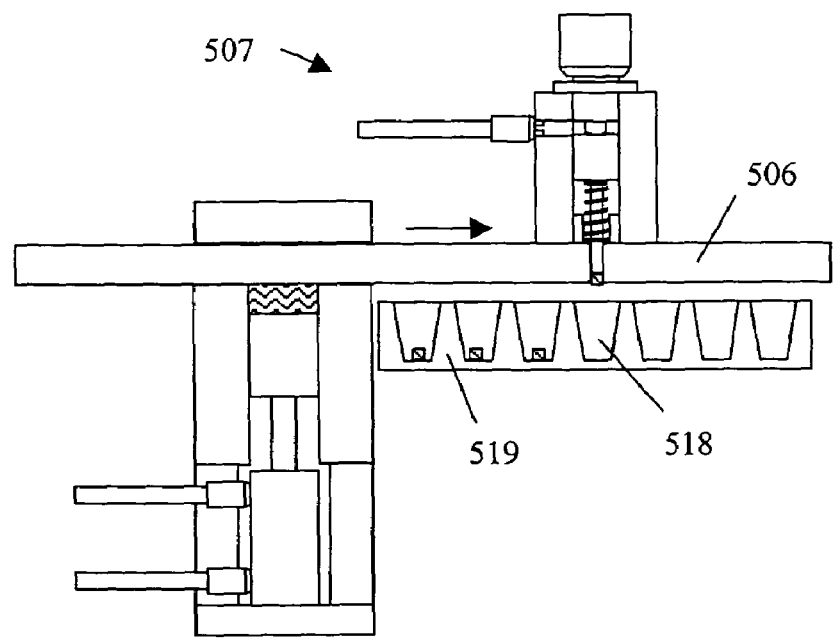
FIG. 12 illustrates a method of ejecting a plug of powder from the dose chamber into a receiving plate.
Figure 12B:
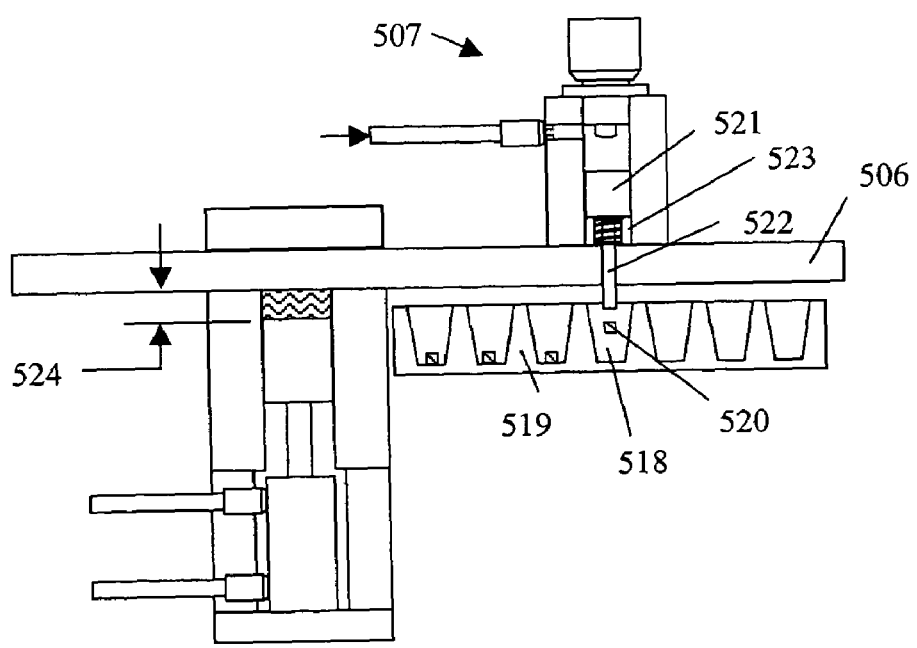

After powder 510 fills dose chamber 513, pressurized air to pneumatic cylinder 505 is switched off. Then, as shown in FIG. 12A, slide plate 506 is moved relative to source block 504 so dose chamber 513 is positioned above target well 518. Next, as shown in FIG. 12B, pressurized air propels ejector pin 522 downwards and ejects plug 520 into target well 518. Ejector piston 521 hits hard stop 523 and decelerates suddenly, thereby flinging powder off of ejector pin 522. Ejector pin 522 is then retracted, slide plate 506 is moved back, and pressurized air is supplied to pneumatic cylinder 505 to press powder 510 again. The fill and eject processes are repeated until source powder height 524 (see FIG. 12B) reaches a minimum, typically 0.4 mm, at which point source chamber 502 is refilled.

Slide plate 506, ejector pin 512, source block 504 and source piston 503 should be made from a hard, wear resistant material that provides a long wear life without lubrication. Suitable materials are tungsten carbide, zirconia, silicon carbide and alumina. If the device only needs to dispense soft powders, a less costly alternative is to use hardened 440C stainless steel coated with a hard ceramic thin film, such as sapphire coating type MH provided by Surface Conversion Sciences Corporation (State College, Pa.). Passive components of the dispense device are preferably made from corrosion resistant stainless steel, such as type 316. To create plugs that have a mass of 50 micrograms, a suitable dose chamber diameter is 0.5 mm, and a suitable source chamber diameter is 2 mm to 5 mm. Slide plate 506 should be 150 mm long or greater to allow a portion of it to remain clamped to source block 504 while allowing dose chamber 513 to reach all wells of an industry standard microtiter plate, which has a footprint of 85 mm by 127 mm.

The mating faces of slide plate 506 and source block 504 should be ground to a flatness of 2 micrometers or better to minimize escape of powder particles. Dose chamber 513 and source chamber 502 should be honed to a roundness of under 2 micrometers, and ejector pin 512 and source piston 503 should be lapped to a roundness of under 2 micrometers, to allow a nominal radial clearance between the respective parts to be within 5 micrometers. Surfaces of ejector pin 512 and source piston 503 that contact powder should be ground flat to within 2 micrometers. Edges on dose chamber 513, source chamber 502, ejector pin 512 and source piston 503 should be left sharp to discourage particles from lodging between the sliding surfaces. To minimize wear, all faces in sliding contact should be polished to a surface finish of less than 0.2 micrometers.

Figure 13A:
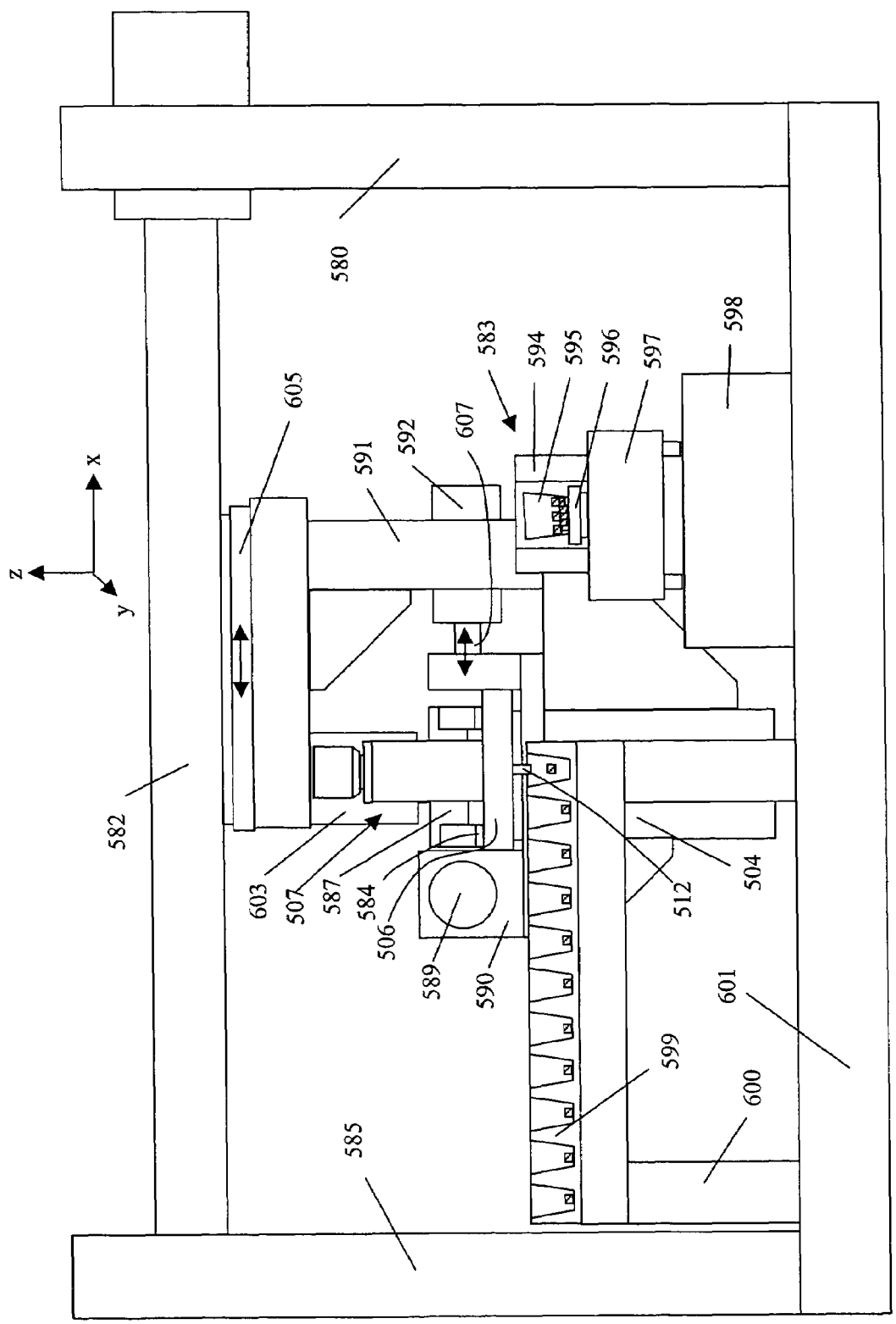
FIG. 13 illustrates the front and side view of a specific apparatus to extrude plugs of powder which includes a dispensing assembly, x and y linear servos, a receiving plate, a weigh station and a supporting base and frame.
Figure 13B:
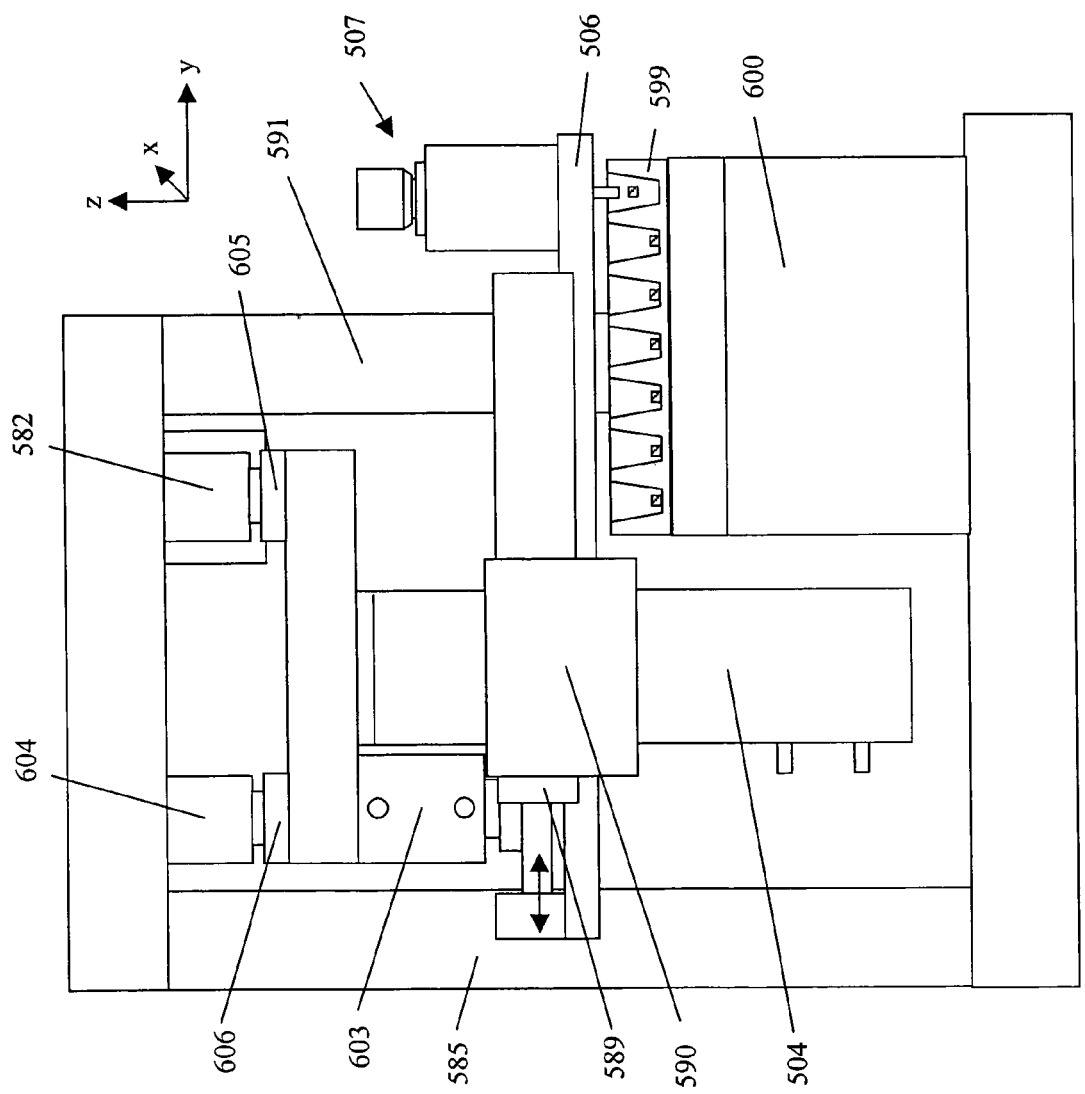

FIGS. 13A and 13B show the front and side view, respectively, of a machine that incorporates dispense device 507 which can dispense into receiving plate 599 and into weigh cup 595 on microbalance 597. Receiving plates can be an industry standard 96 well, 384 well, or 1536 well format, or a custom format. Receiving plate 599 is supported by pedestal 600 on machine base 601. Slide plate 506 is moved relative to source block 504 by x linear actuator 592 and y linear actuator 589. Suitable actuators are from the ROBO CYLINDER® series made by Intelligent Actuator, Inc., Japan. Pneumatic cylinder 603 connected to yoke 587 presses slide plate 506 against source block 504. Yoke 587 has feet 584 made from ultrahigh molecular weight, polyethylene to minimize sliding friction. Pushrod 607 of servo 592 connects to shuttle frame 590, which in turn is connected to servo body 589, thereby allowing x and y movement of slide plate 506 relative to source block 504.

Linear actuator 582, supported by columns 585 and 580, moves dispense device 507 in the x direction to allow dispensing into receiving plate 599. As shown in FIG. 13B, dispense device 507 is supported by C-frame 591 which connects to carriages 605 and 606. Slave linear guide 504 provides added support for C-frame 591. Suitable linear actuators and supporting control hardware and software are made by Intelligent Actuator, Inc., Japan.

Weigh station 583 shown in FIG. 13A allows plugs to be weighed for characterization and statistical tracking. Weigh station 583 comprises microbalance 597 with weighing platform 596, weigh cup 595, and draft shield 594. Microbalance 597 is supported by granite pedestal 598. A suitable microbalance is the UMX2 model made by Mettler Toledo, Switzerland.

Example 3

Manipulating Solids by Extruding Multiple Plugs of Powder Simultaneously

Figure 14A:
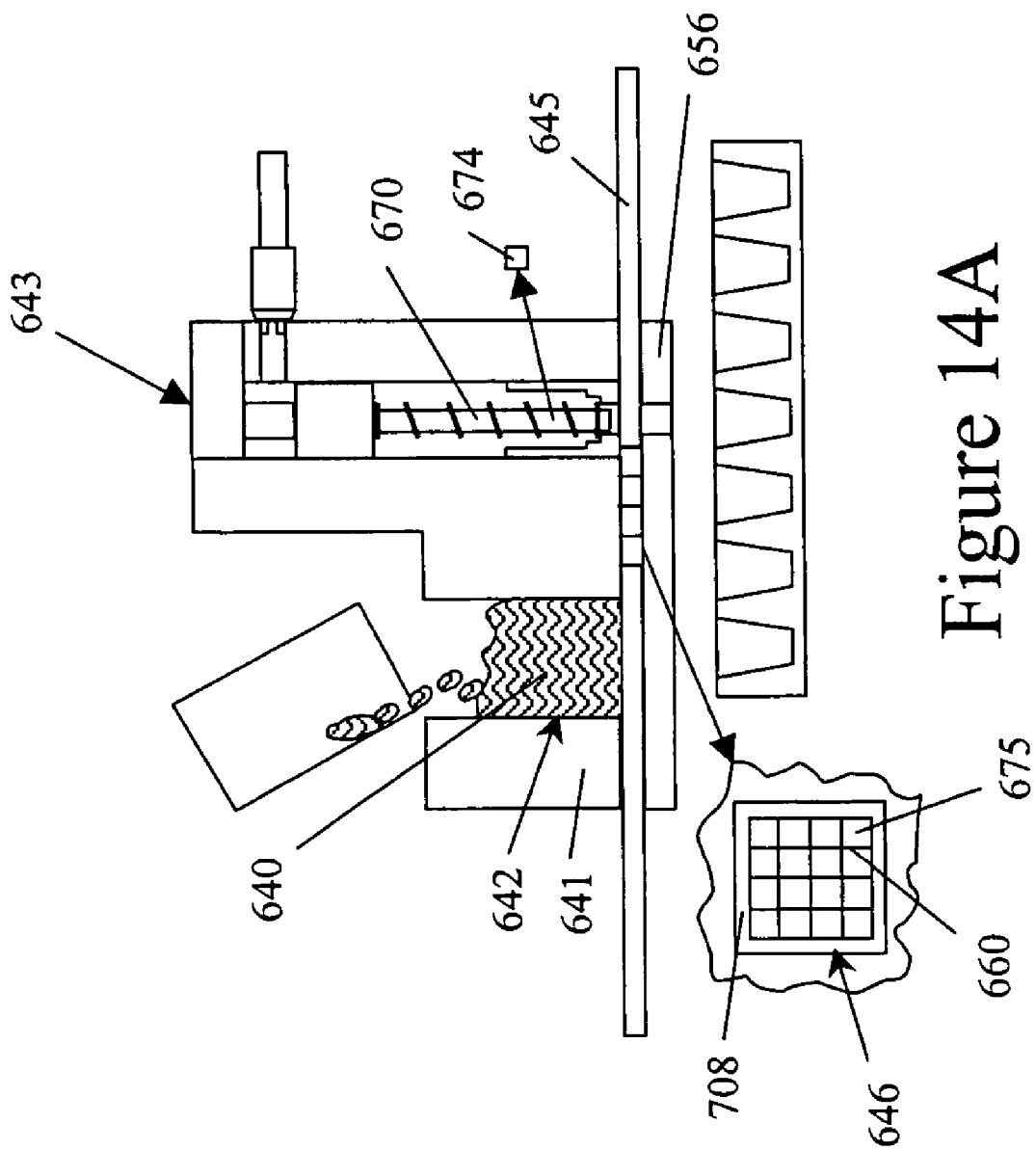
FIG. 14 illustrates a method of preparing solids for extrusion.

This example is based on a similar method and apparatus as Example 2 except that it demonstrates a new method and apparatus for extruding multiple plugs of powder simultaneously. To begin, FIG. 14A shows that a known mass of powder 640 (e.g., less than about 1 gram, 500 mg, 100 mg, 25 mg, 1 mg, 500 micrograms, 250 micrograms, or 100 micrograms) is dispensed into a source chamber 642. Then, in FIG. 14B, assembly 648 comprising pneumatic cylinder 651 and source piston 649 is attached above source chamber 642. At the base of source chamber 642 is slide plate 645 which is in between source block 641 and keeper 656. Powder 640 is initially compressed inside source chamber 642 against slide plate 645 by supplying air to pneumatic cylinder 651 at typically about 5 to about 50 psi.

Figure 14B:
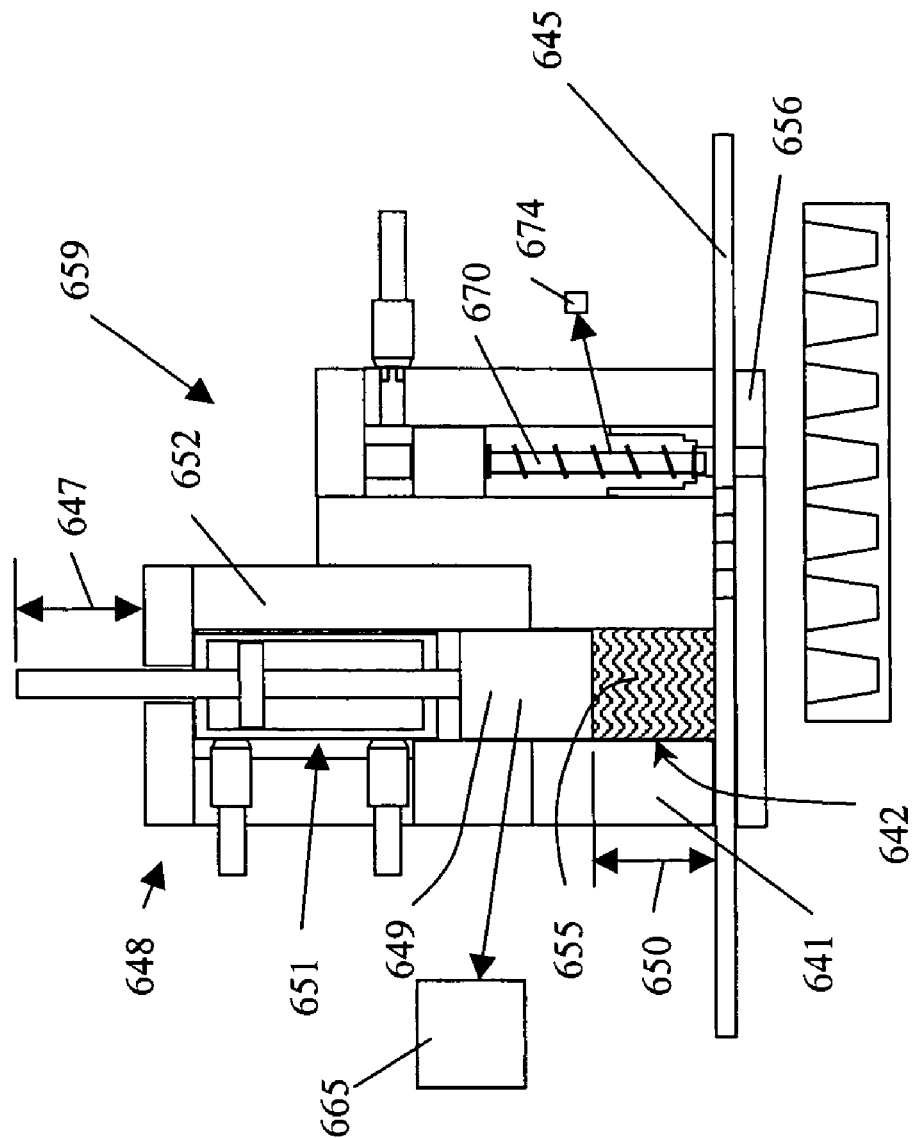
Figure 15:
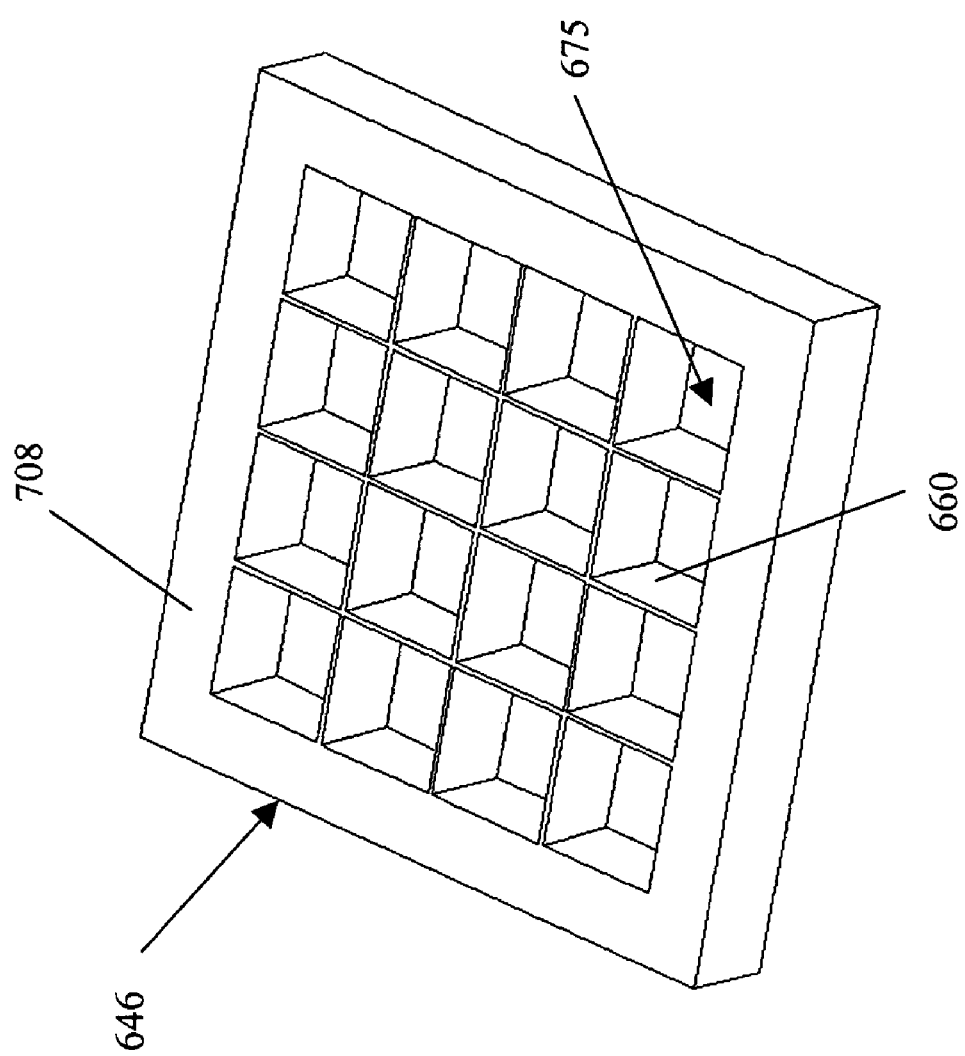
FIG. 15 illustrates the grid cutter utilized in the method shown in FIG. 14.

FIG. 14B also shows that source piston 649 has square cross section 665 sized to fit precisely into square source chamber 642 (round or other cross section shapes can also be used). Slide plate 645 includes multiple hollow partitions such as grid cutter 646 (See FIG. 15), which comprises frame 708 holding a grid of thin blades such as 660 which form square partitions such as 675. FIG. 15 shows an isometric view of grid cutter 646. Ejector pin 670 has a square cross section 674, sized to fit precisely into grid partitions such as 675. However, source chamber 642, source piston 649, ejector pin 670, and partitions 675 in grid cutter 646 can be designed to have any arbitrary shape including, circular, rhombic, or hexagonal shape such that the parts fit appropriately within each other.

Figure 16A:
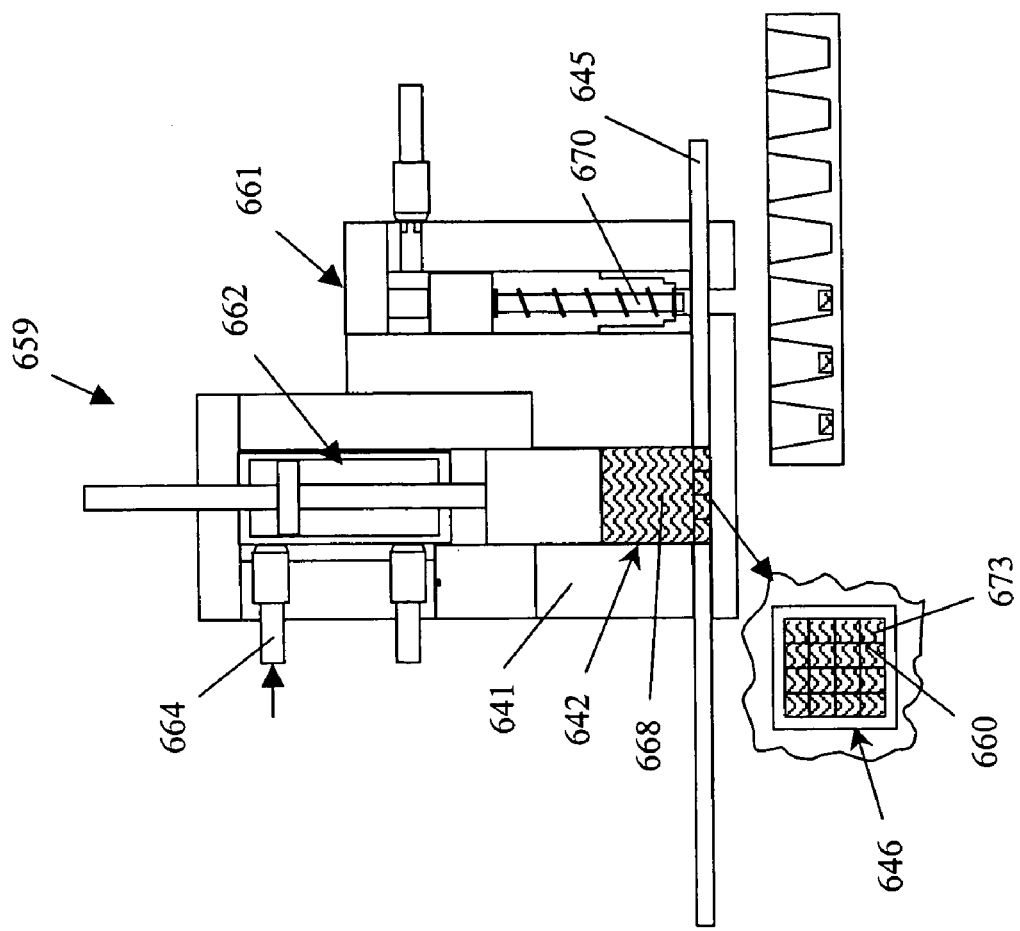
FIG. 16 illustrates a method of extruding multiple plugs of powder and ejecting the plugs into a receiving plate.
Figure 16B:
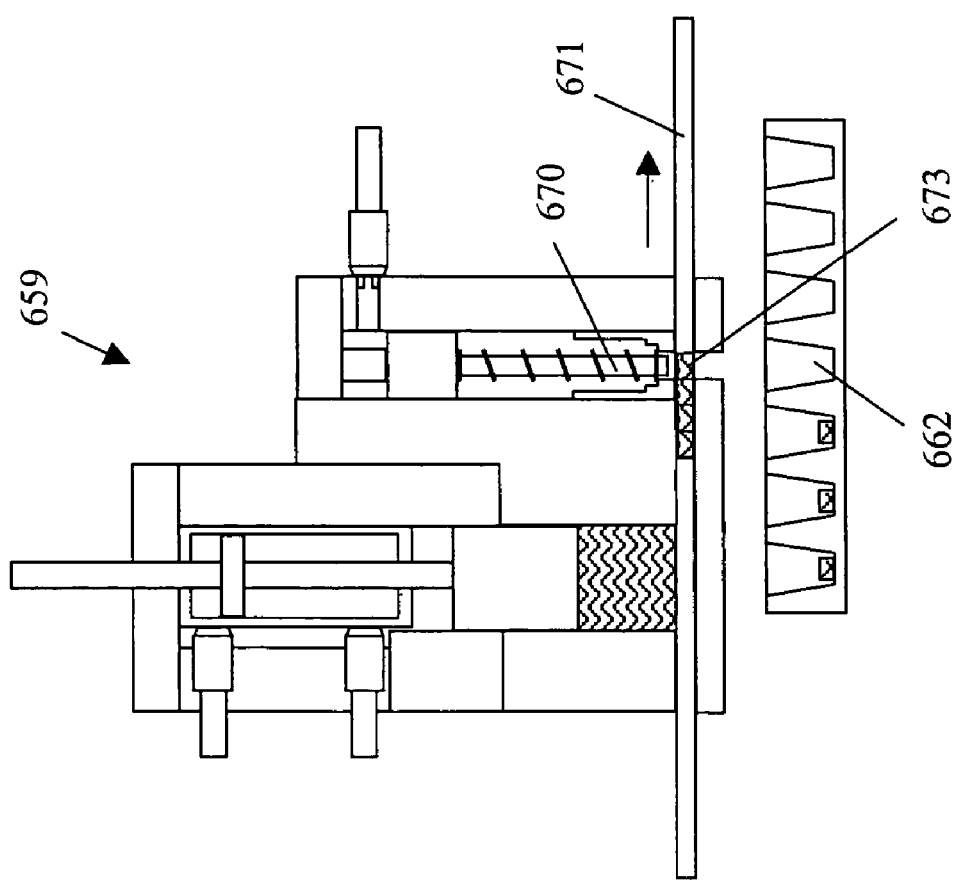
Figure 16C:
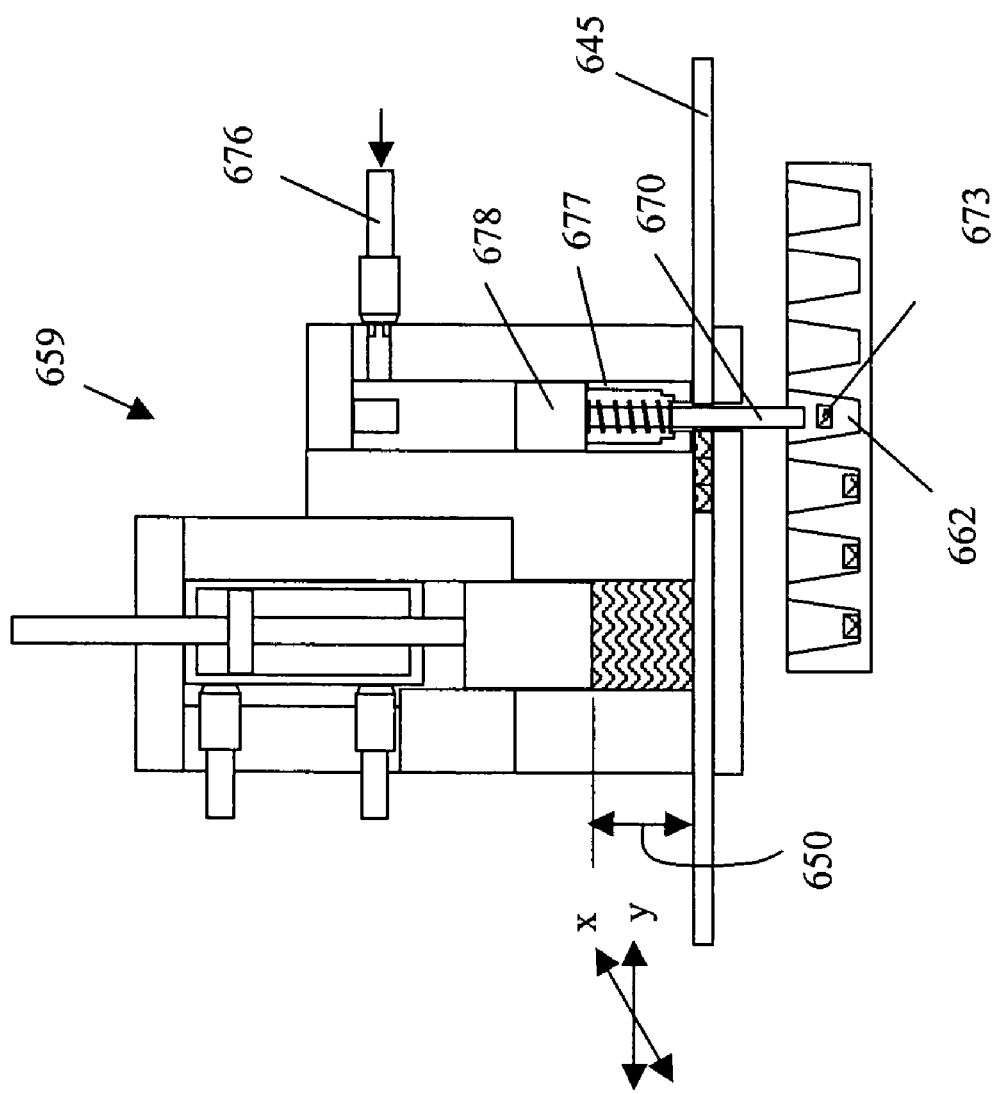

After powder 655 is initially compressed to achieve a uniform packing density of powder in source chamber 642, the pressurized air supply to port 664 (See FIG. 16A) of pneumatic cylinder 662 is released and slide plate 645 is moved directly below source chamber 642. Then, as shown in FIG. 16A, pressurized air is supplied to port 664 to press powder 668 through blades 660 of grid cutter 646. Pressurized air to port 664 is then switched off, and slide plate 645 is moved so plug 673 is under ejector pin 670, as shown in FIG. 16B. Dispense device 659 is also moved so plug 673 is over target well 662. Next, as shown in FIG. 16C, pressurized air is supplied to port 676 and it propels ejector pin 670 down to eject powder plug 673 into target well 662. Ejector piston 678 hits hard stop 677 and decelerates suddenly, thereby flinging virtually all powder off ejector pin 670. Slide plate 645 is then translated incrementally so another partition is under ejector pin 670, and the eject process is repeated. The extrude and eject processes are repeated until source powder height 650 reaches a value that is less than the slide plate thickness. The minimum source powder height can be detected with a standard hall effect sensor.

Figure 17:
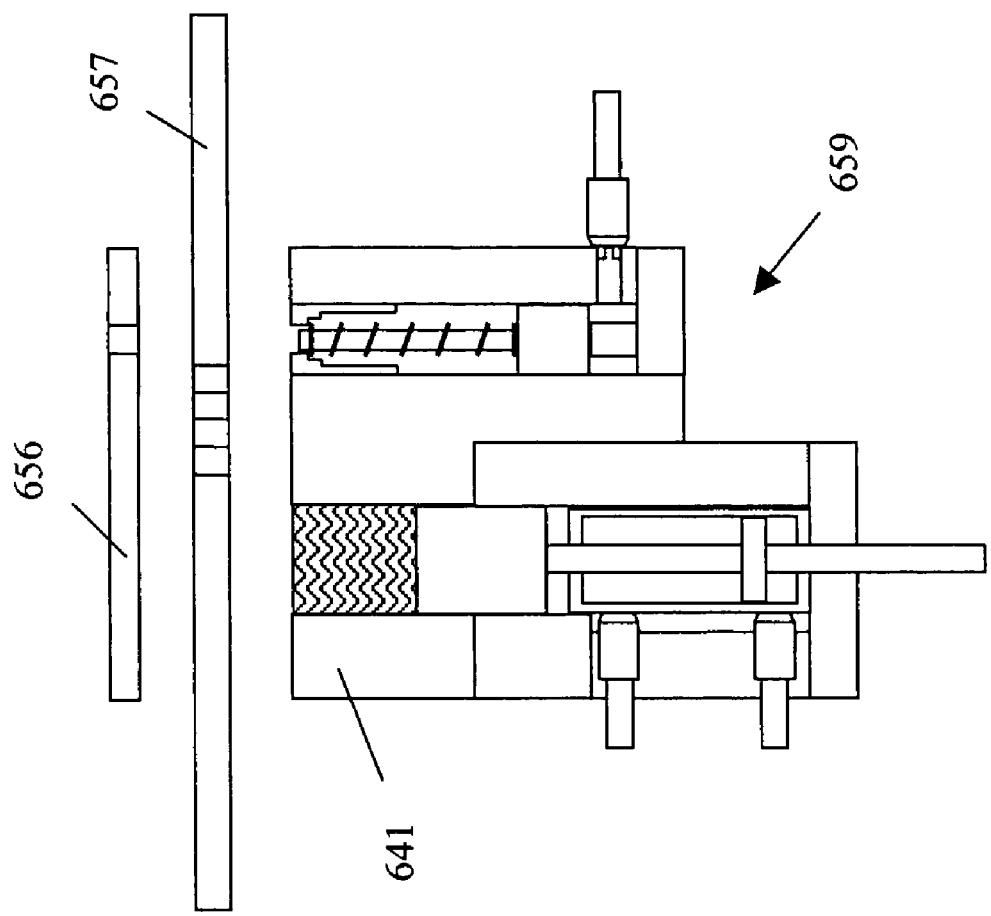
FIG. 17 illustrates a method of installing a slide plate to vary the thickness of the plugs of powder produced.
Figure 18A:
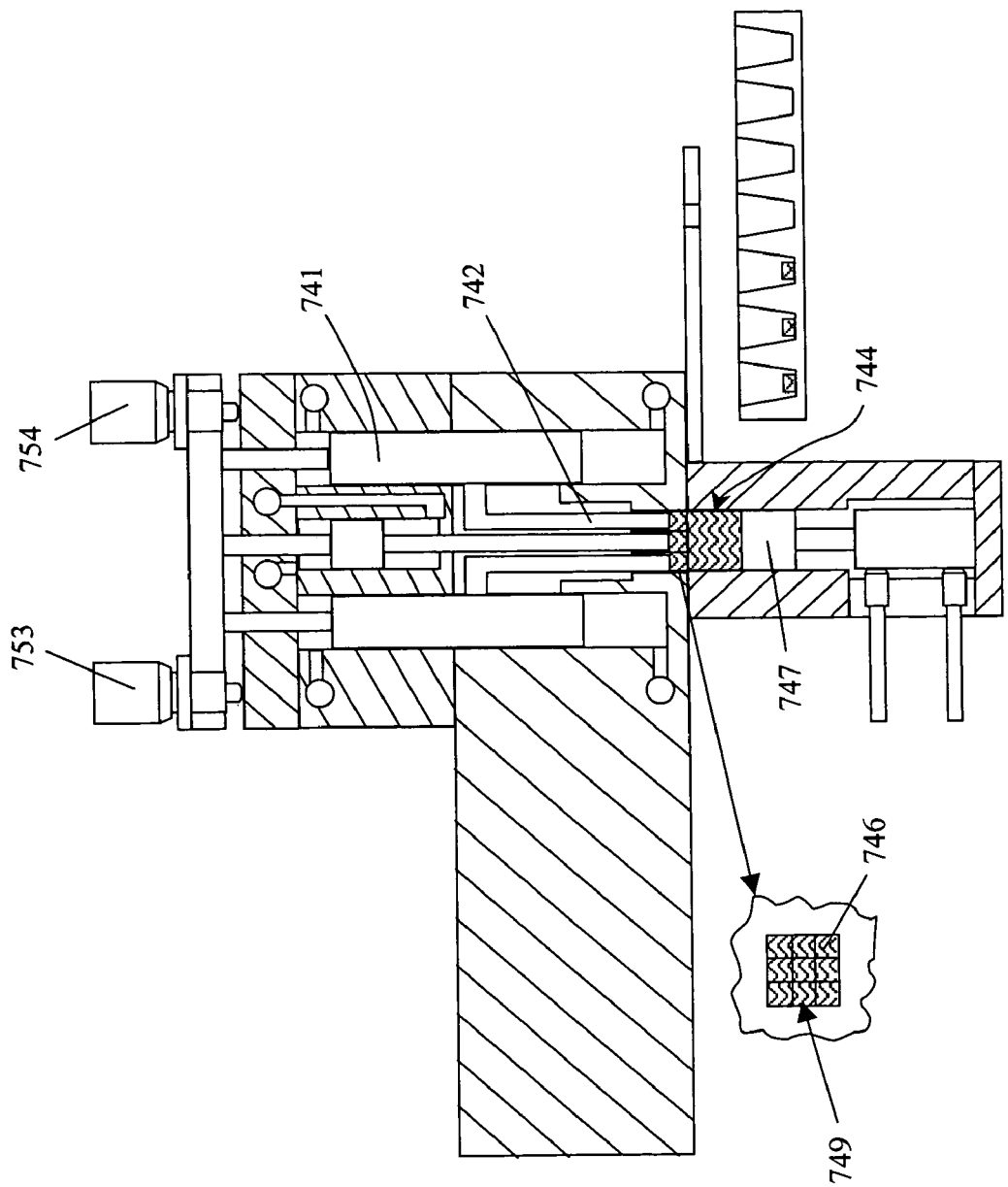
FIG. 18 illustrates a method of extruding multiple plugs of powder of different thicknesses using more than one ejector pin.
Figure 18B:
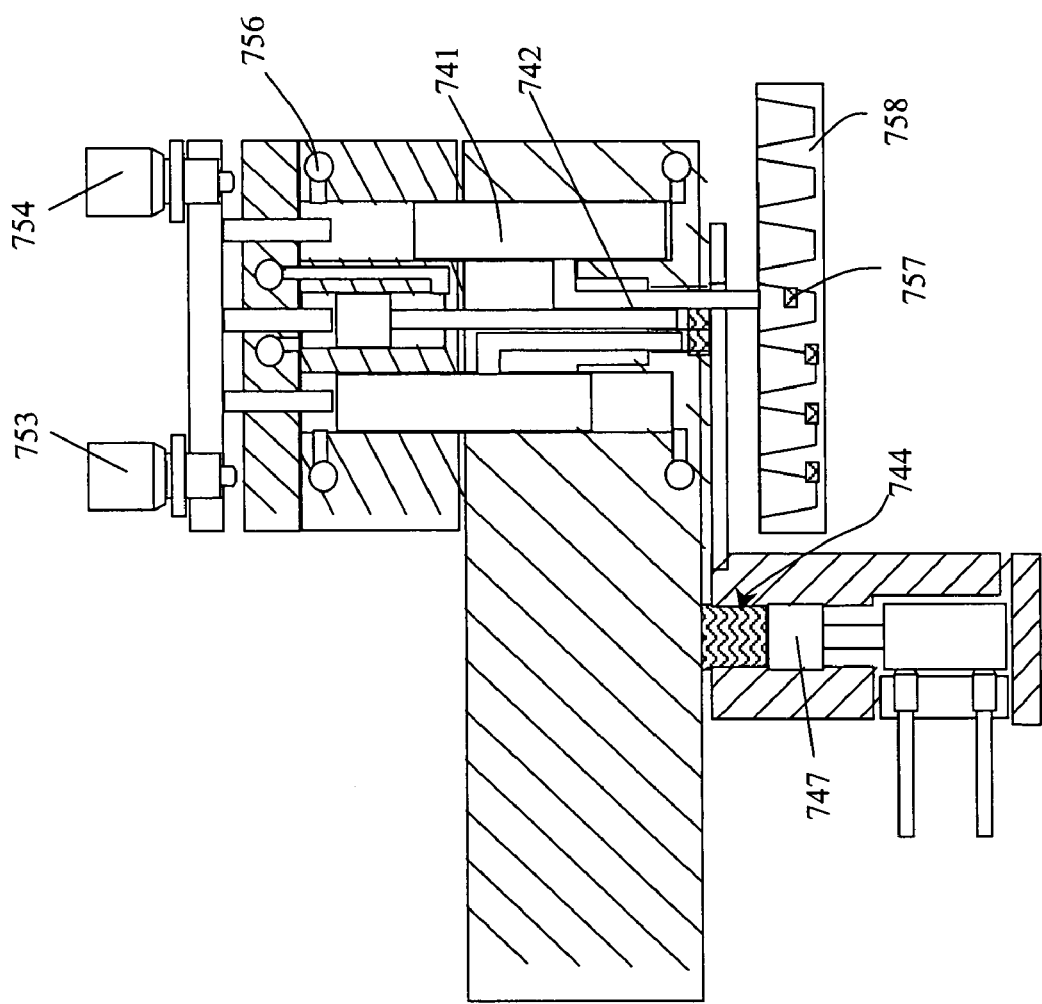

For this embodiment shown in FIGS. 16A through 16C, the average packing density of powder 668 and the thickness of slide plate 645 determine the average mass of plugs produced. The average packing density of powder 668 is estimated by measuring rod height 647 (FIG. 14B) which determines powder height 650, as shown in FIGS. 14B and 16A-C. For example, the average packing density is equal to the mass of powder 668 divided by the powder height 650 and the base area of source chamber 642. Thus, the average mass of powder plug 673 is equal to the packing density times the thickness of slide plate 645 and base area of partition 675. An assortment of slide plates with different thicknesses is made available to provide an average plug mass that is acceptably close to a target value. As a non-limiting example to install a new slide plate 657, FIG. 17 shows dispense device 659 inverted and keeper 656 is removed and reattached. Alternatively, another embodiment is shown in FIGS. 18A and 18B where the height of each partition 746 in grid cutter 749 is controlled by independent micrometers 753 and 754 connected to individual ejector pins 742.

Slide plate 645, ejector pin 670, source block 641 and source piston 649 should be made from a hard, wear resistant material that provides a long wear life without lubrication. Non-limiting suitable materials include tungsten carbide, zirconia, silicon carbide or alumina. If only soft powders are being deposited, a less costly alternative is to use hardened 440C stainless steel coated with a hard ceramic thin film, such as sapphire coating type MH provided by Surface Conversion Sciences Corporation (State College, Pa.). The structural components of the dispense device are preferably made from a corrosion resistant stainless steel, such as type 316. Grid cutter insert 646 is preferably made from a tungsten carbide plate whose faces are ground and polished. The partitions can be cut by plunge or wire electrical discharge machining.

Determining the various parameters necessary to make plugs of specific masses can be done using techniques and materials well known in the art. For example, to create plugs that have a mass of approximately 50 micrograms, a suitable thickness for slide plate 645 and cutter insert 646 is 0.4 mm, and a suitable partition dimension is 0.4 mm wide by 0.4 mm long. A suitable cutter wall thickness is 75 micrometers. The mating faces of slide plate 645, source block 641, and keeper 656 should be ground to a flatness of 2 micrometers or better to minimize escape of powder particles. Source chamber 642 walls should be lapped to an accuracy of under 2 micrometers, and ejector pin 670 and source piston 649 walls should be lapped to an accuracy of under 2 micrometers. The nominal clearance between square ejector pin 670 and a grid cutter partition such as 675 should be 10 micrometers or less. Ejector pin 670 and source piston 649 faces that contact powder 640 should be ground flat to within 2 micrometers. The edges on grid cutter 646, ejector pin 670, source chamber 642, and source piston 649 should be left sharp to discourage particles from lodging between the sliding surfaces. To minimize wear, all of the faces in sliding contact should be polished to a surface finish of less than 0.2 micrometers.

Figure 19A:
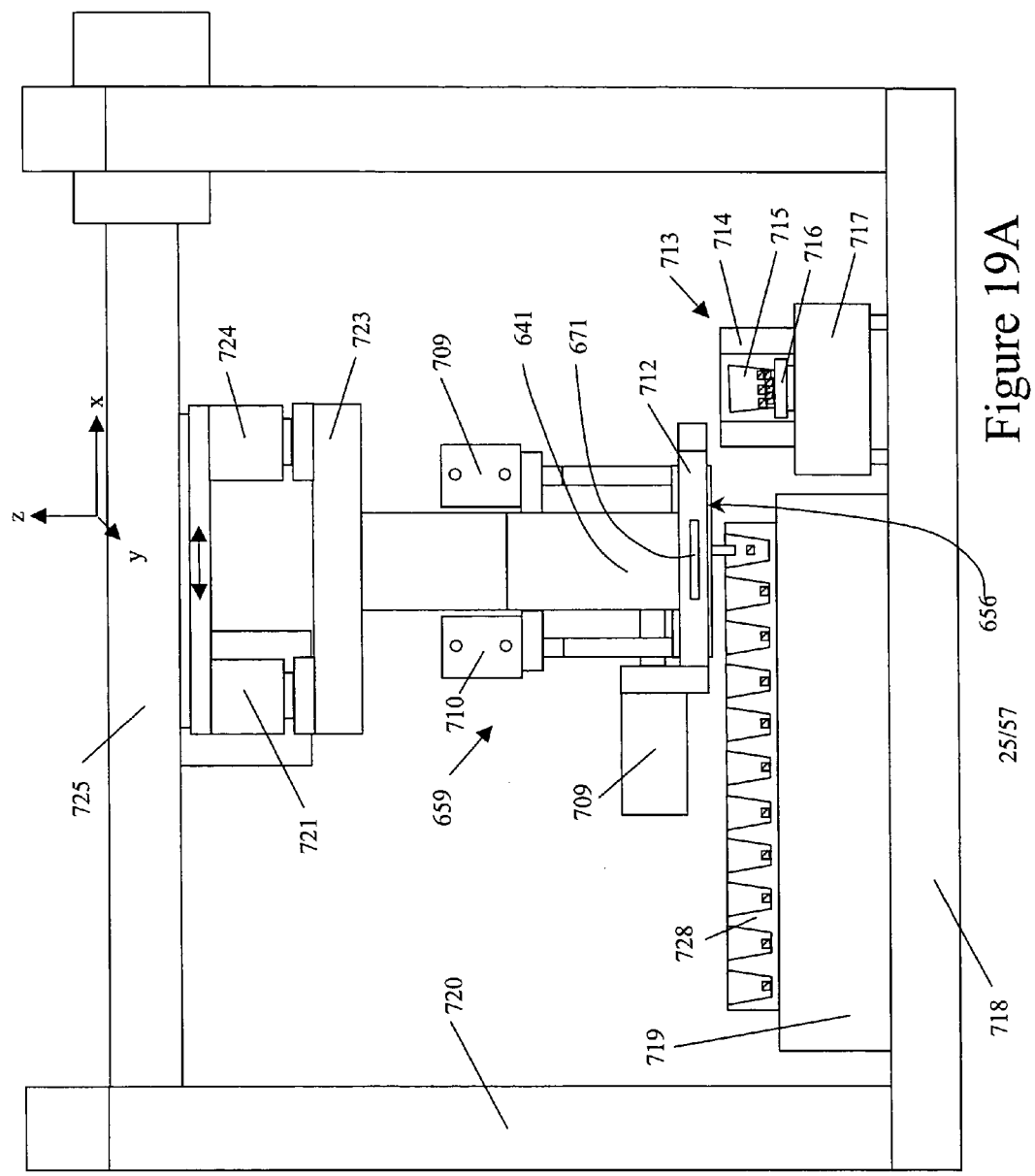
FIG. 19 illustrates the front and side view of a specific apparatus to extrude multiple plugs of powder which includes a dispensing assembly, x and y linear servos, a receiving plate, a weigh station and a supporting base and frame.
Figure 19B:
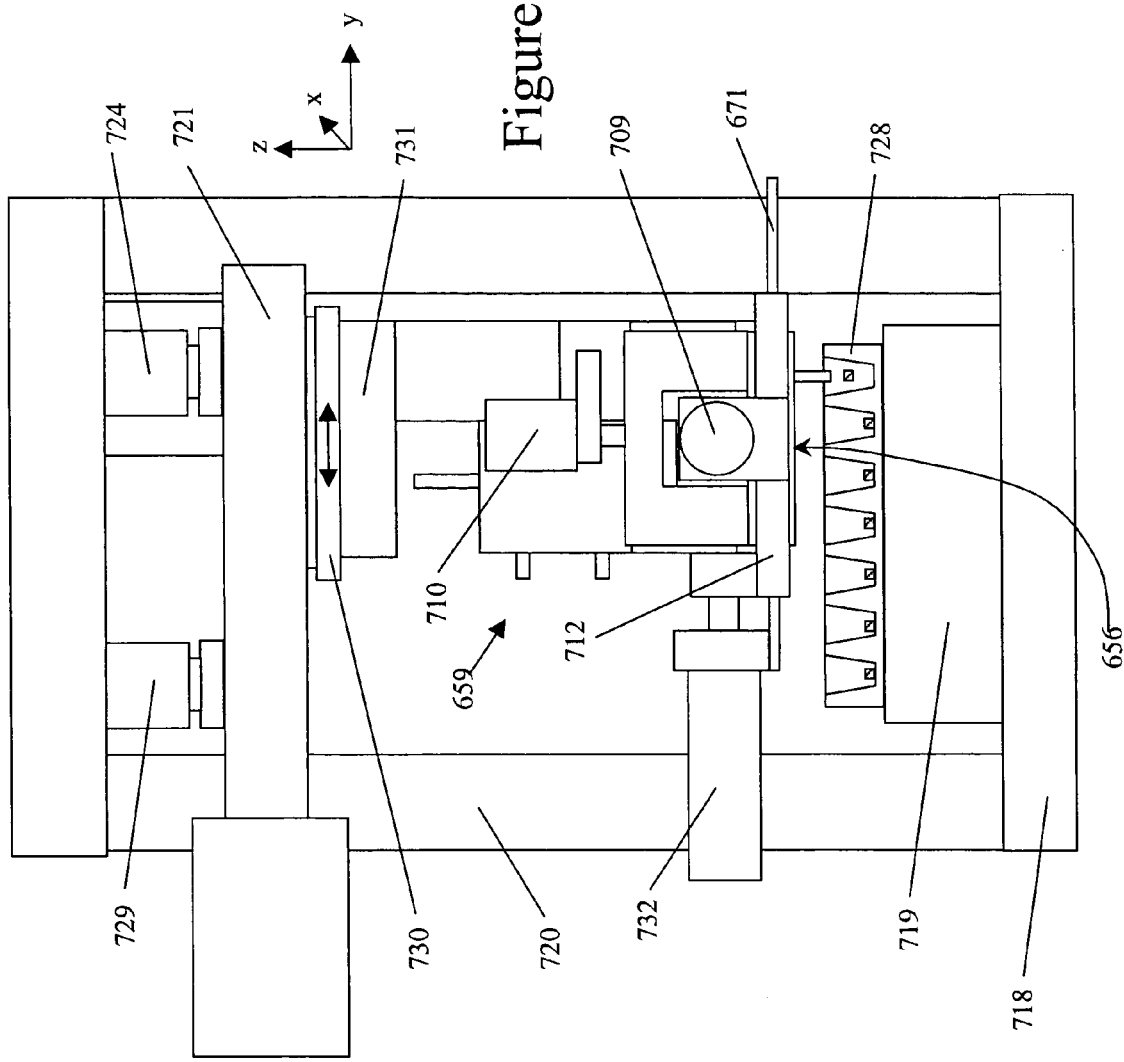

FIGS. 19A and 19B show a machine that incorporates dispense device 659, which can dispense into receiving plate 728 and into weigh cup 715 on microbalance 717. Receiving plates can be an industry standard 96 well, 384 well, or 1536 well format, or a custom format. Receiving plate 728 is supported by pedestal 719 on machine base 718.

Slide plate 645 is moved in both x and y directions relative to source block 641 by x servo 709 (See FIG. 19A) and y servo 732 (See FIG. 19B). Suitable servos are the ROBO CYLINDER® series made by Intelligent Actuator, Inc., Japan. Part 712 couples the x and y servos to slide plate 645. Clamping pneumatic cylinders 709 and 710 force keeper 656 to hold slide plate 645 against source block 641.

X linear actuator 725 and y linear actuator 721 move dispense device 659 relative to machine base 718. Slave z linear guide 729 and y linear guide 721 provide added stiffness to the support of dispense device 659. Suitable linear actuators and supporting control hardware and software are made by Intelligent Actuator, Inc., Japan.

Weigh station 713 allows plugs to be weighed for characterization and statistical tracking. As shown in FIG. 19A, it comprises microbalance 717, weigh cup 715 on weighing platform 716, and draft shield 714. A suitable microbalance is the UMX2 model made by Mettler Toledo, Switzerland.

Example 4

Manipulating Solids by Producing a Slurry Suspension

The physical characteristics of some solids make them more amenable to manipulation using a carrier. Consequently, this invention encompasses a method of manipulating solids that utilizes slurries. In this method, a solid or mixture of solids is combined with a liquid vehicle to form a slurry mixture, which is dispensed by using standard liquid handling devices (e.g., pipettes). The liquid vehicle is then removed (e.g., by evaporation, filtration, or sedimentation) to provide the solids. Long drying times and low drying temperatures are preferably used to promote crystal formation. Advantageously, a liquid vehicle can be selected such that it allows the ready manipulation of a given solid but does not dissolve a substantial portion of solid. By avoiding the formation of a solution into which the solid is dissolved, the method allows the manipulation of controlled amounts of solids without substantially affecting their solid forms.

The selection of a liquid vehicle that can be used to provide a slurry of a solid that is easy to manipulate (e.g., prepare, handle, and/or dispense) can be done with little or no routine experimentation. Preferred liquid vehicles are readily removed (e.g., evaporated) and do not chemically react with the solid. The solid or solids being manipulated are also insoluble or have a low solubility (e.g., less than about 10 mg/mL, 1 mg/mL, 0.1 mg/mL, 0.01 mg/mL or 0.001 mg/mL) in preferred liquid vehicles. In a specific method, the liquid vehicle comprises a wetting agent and water. The purpose of the wetting agent is to lower the surface tension of the water. Examples of wetting agents include, but are not limited to, alcohols such as isopropyl alcohol and methanol, sodium lauryl sulfate, polyvinylpyrrolidone (PVP), and TWEEN®.

In a specific method, samples of the slurry suspension are collected into vials for high-performance liquid chromatography (HPLC) analysis during the dispensing step. These vials are used to validate how much solid was actually transferred during each dispense. In a specific method, solid-state analysis is performed after the liquid vehicle is removed (e.g., vacuum or evaporated) to verify that the solid has not substantially changed in form. Examples of techniques that can be used for this determination include, but are not limited to, NMR spectroscopy (e.g., $^1$H and $^{13}$C NMR), Raman spectroscopy (e.g., resonance Raman spectroscopy), X-ray spectroscopy, powder X-ray diffraction, absorption and emission spectroscopy (e.g., infrared, visible, and ultraviolet absorption and emission), birefringence, differential scanning calorimetry (DSC), and thermogravimetric analysis (TGA).

Example 5

Manipulating Solids by Using Adhesive Surfaces

In another embodiment of the invention, solids (e.g., powders) are manipulated using an adhesive surface to which a controlled amount of solid can be adhered. Particular methods of this embodiment utilize a surface comprised of two or more adhesive areas separated by non-adhesive areas (i.e., areas to which a given solid will not adhere or will adhere more weakly than it does to an adhesive area). Preferably, the adhesive areas are of approximately the same size and shape. Examples of specific sizes of adhesive areas include, but are not limited to, less than about 5 cm$^2$, 2.5 cm$^2$, 1 cm$^2$, 50 mm$^2$, 10 mm$^2$, 1 mm$^2$, and 0.5 mm$^2$.

Adhesive areas can be formed in a variety of ways. Examples include, but are not limited to, adhering an adhesive to a non-adhesive backing, overlaying an adhesive backing with a non-adhesive mask, and treating regions of a non-adhesive backing with chemicals, radiation, plasma, or other means sufficient to render those regions adhesive. Such methods are well known in the art. See, e.g., U.S. Pat. Nos. 6,284,329, 6,221,268, and 6,096,156, each of which is incorporated herein by reference.

Figure 20:
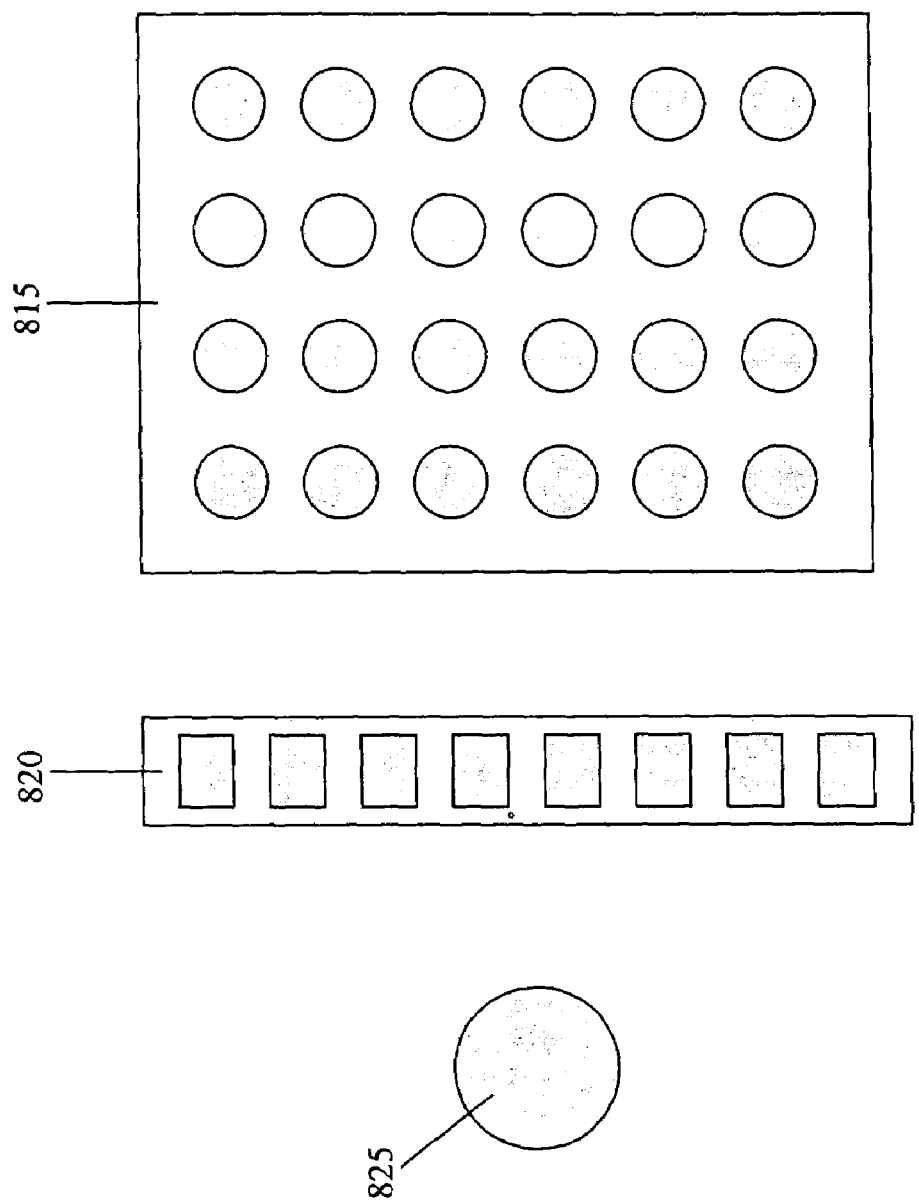
FIG. 20 illustrates various arrangements of adhesive areas on a surface to manipulate solids.

FIG. 20 provides various non-exhaustive illustrations of possible adhesive patch arrangements, which include arrays 815, strips 820, and wafers 825. The surface area of the adhesive and particle size of the powder will affect the amount of solid attached to a specific area 825. The pattern can be a familiar array of shapes, such as an array of circles, squares, lines, or other structures arranged in a pattern such as a grid or a spiral. Suitable backing materials can be stiff (e.g., made of glass or plastic) or flexible (e.g., plastic carrier film).

Figure 21:
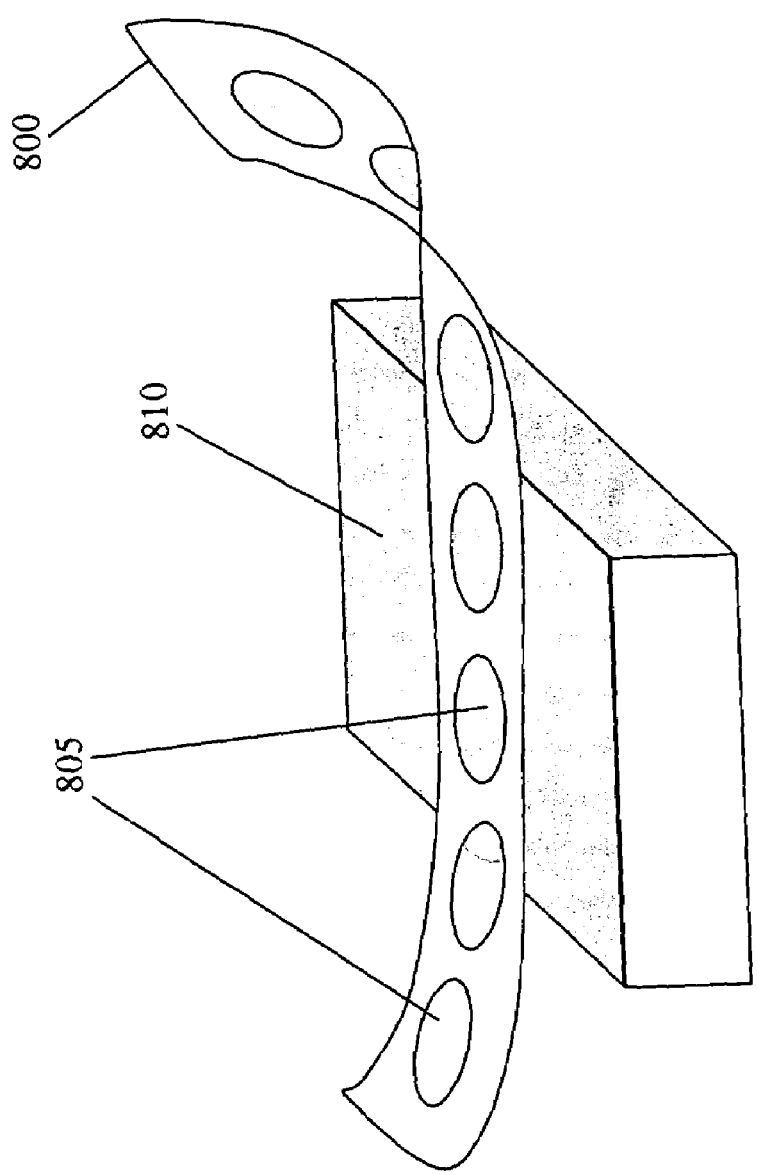
FIG. 21 illustrates a method of applying solids to the adhesive areas on a surface.

The patterned surface is preferably de-ionized using an ion-gun to reduce non-specific and undesirable electrostatic interactions that can affect powder adhesion. Powder is then applied to the surface by, for example, pushing the surface into a powder bed, dipping the surface into a powder, spreading the powder across the surface and tapping off the excess, or sprinkling the powder over the surface and tapping off the excess. If any powder remains electrostatically adhered to undesired sections of the surface, an ion air-gun can be used to gently blow it off of the surface. FIG. 21 illustrates an example of this embodiment, wherein sticky adhesive patches 805 on a de-ionized substrate 800 are contacted with a bed of powder 810. In one embodiment, less than about 1 mg of powder is adhered to an adhesive area. In another embodiment, less than about 0.5 or 0.25 mg of powder is adhered to an adhesive area.

After the solid preferentially adheres to the adhesive areas, the solid is removed from the substrate and transferred to a container or receptacle for further utilization (e.g., study, or experimentation). In a specific method, the solid is dissolved in a solvent and the resulting solution is transferred to the receptacle. Preferably, the adhesive (if one is used) is not soluble or is only sparingly soluble in the solvent. In another method, the solid is transferred using a liquid or gel in which the solid is insoluble or only sparingly soluble, but to which it adheres or in which it is trapped with enough affinity to facilitate its removal from the adhesive area. An example of such a liquid is polyethylene glycol (PEG).

Figure 22:
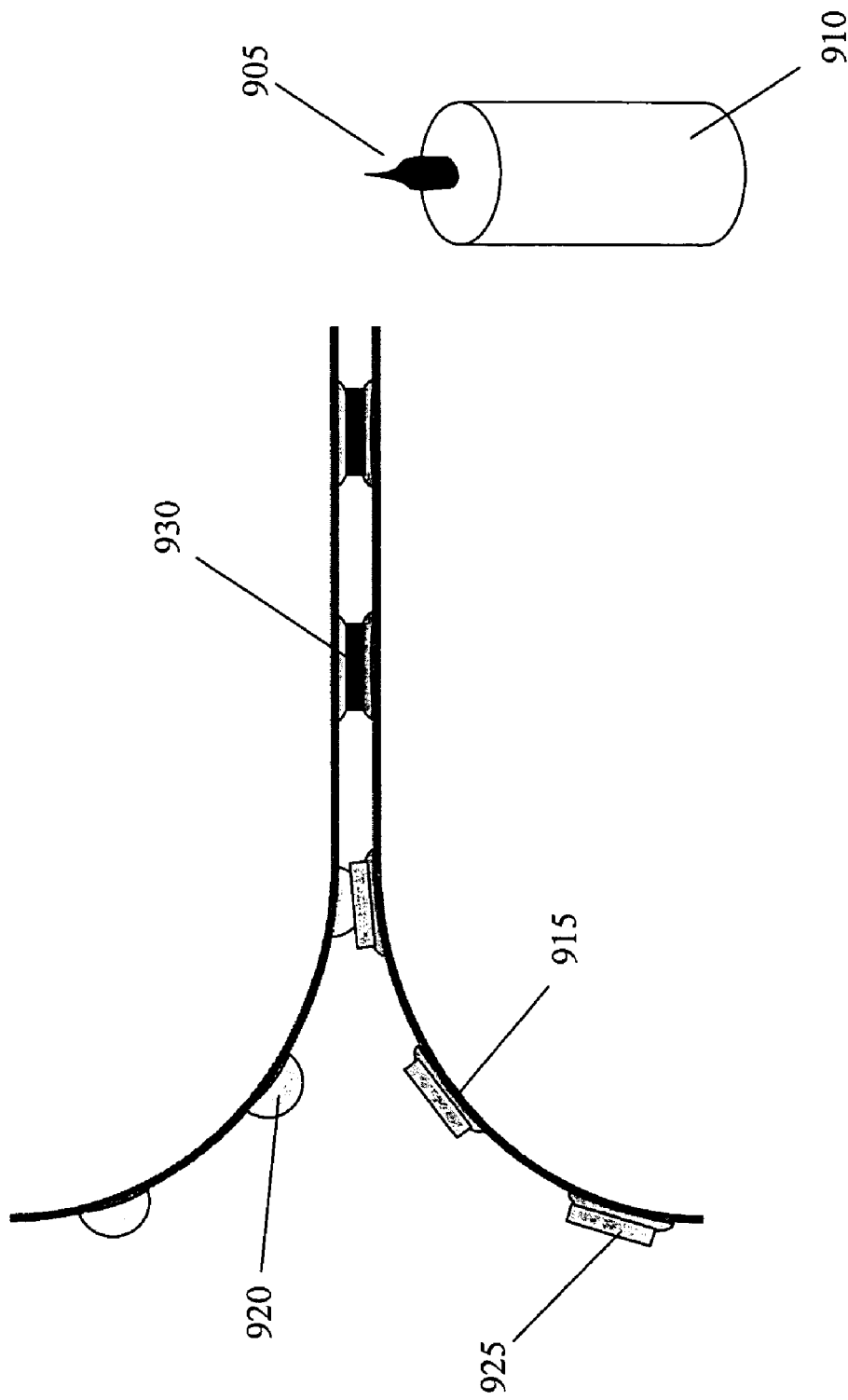
FIG. 22 illustrates a method of mixing solids adhered to an adhesive area with a solvent, reagent or excipient suspended on a separate surface such that the resultant agglomeration can be easily dispensed into a container.

FIG. 22 illustrates a way by which a solid adhered to an adhesive area on a substrate or backing can be dispensed into a container (e.g., a well in a multi-well plate). According to this particular method, a reagent, solvent, or excipient 920 adhered or otherwise suspended on a backing is contacted with solid 925 adhered to a strip or array of adhesive areas 915 to provide a mixture 930. The reagent, solvent, or excipient is selected such that the resulting mixture will not remain adhered to the strip or array 915 and will form an easily dislodged or displaced agglomeration 905. The agglomeration can thus be readily dispensed into a suitable container 910 using, for example, a centrifuge, vibration, vacuum, or simply gravitational force. Preferred reagents do not react with, or substantially affect the form of, the solid being manipulated, and do not dissolve the adhesive. The reagent can optionally be removed using a variety of techniques such as, but not limited to, evaporation, filtration, and sedimentation.

Depending on the particular use to which the solid is put, it may or may not need to be removed from the adhesive area to which it is adhered. In one embodiment of the invention, the solid is utilized (e.g., studied) while still adhered to an adhesive area on a backing. For example, a variety of experiments can be conducted in series or in parallel directly on a sheet or strip of solid samples, such as those shown in FIG. 20.

In a specific method, solid-state analysis is performed to verify that the solid has not substantially changed in form during transfer. Examples of techniques that can be used for this determination include, but are not limited to, NMR spectroscopy (e.g. $^1$H or $^{13}$C NMR), Raman spectroscopy (e.g., resonance Raman spectroscopy), X-ray spectroscopy, powder X-ray diffraction, absorption and emission spectroscopy (e.g., infrared, visible, and ultraviolet absorption and emission), birefringence, differential scanning calorimetry (DSC), and thermogravimetric analysis (TGA).

Example 6

Transferring Solids from One Container into Another Container

During the process of manipulating small amounts of solid, it may be necessary to transfer the solid content inside one container into a different container. For example, weighing small amounts of solid on a precision microbalance (e.g., the Sartorius SC2 Ultra Micro) requires a low-mass container (e.g., less than 2 g) in order to achieve sufficient mass resolution (e.g., 0.1 microgram readability). However, further processing of those solids may require a higher-strength container or a two-dimensional array format, both of which would exceed the mass limit of such a microbalance. For such applications and others, various methods and apparatuses for transferring solids from one container into another container are described below.

Figure 23A:
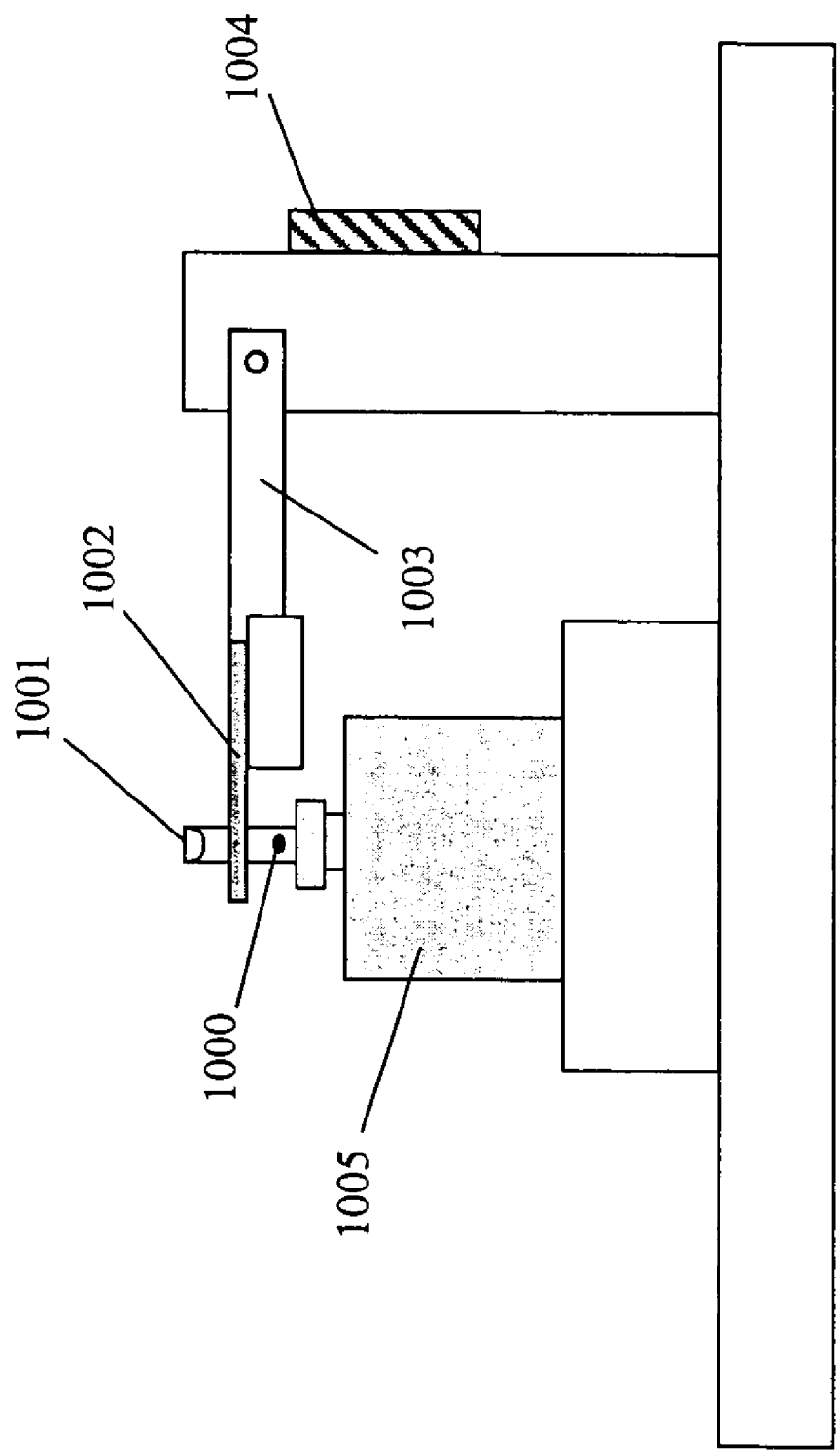
FIG. 23 illustrates a method of transferring solids from one container into another container by turning the original container upside-down.
Figure 23B:
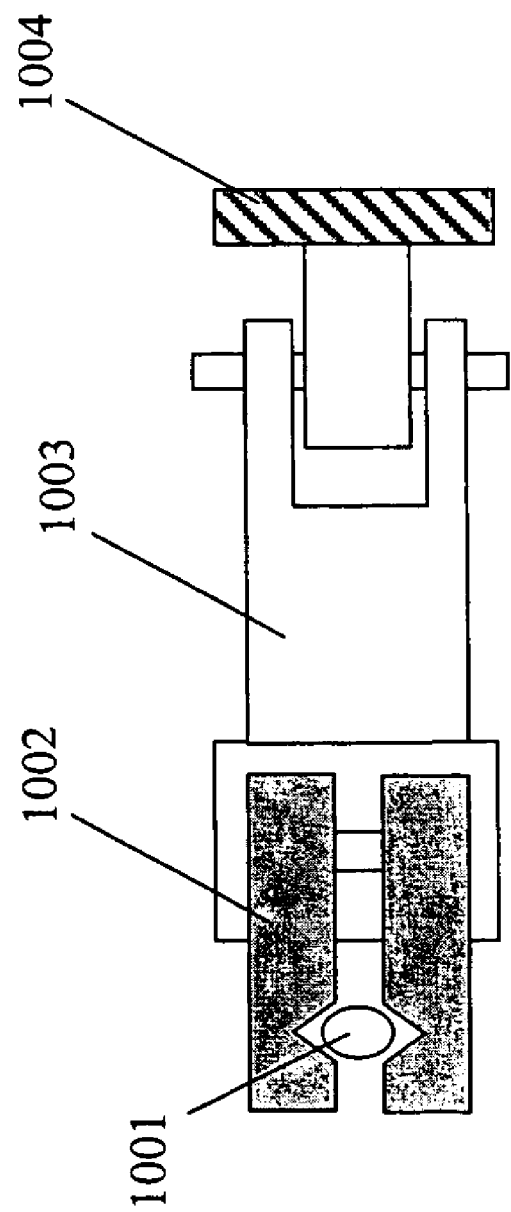
Figure 23C:
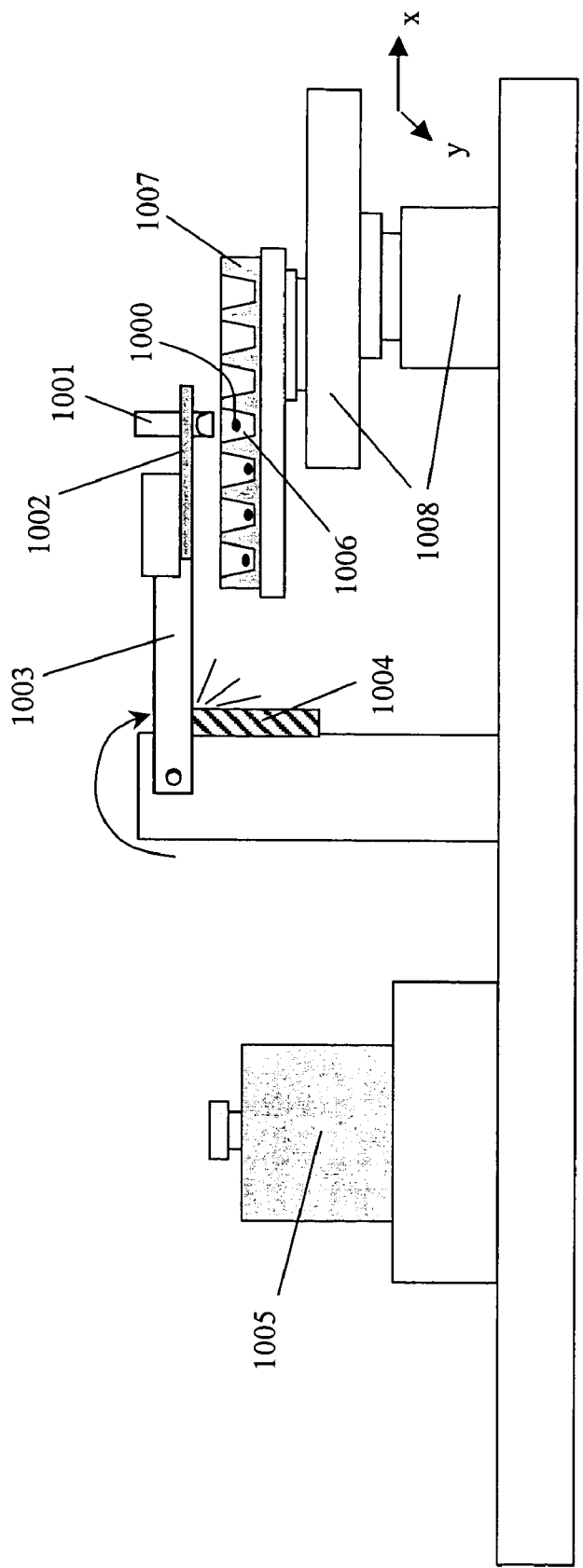

In a specific method and apparatus, the container that originally holds the solids 1000 is a conventional open-faced vessel 1001 that can be weighed by a microbalance 1005 as shown in FIG. 23A. The solids 1000 are transferred into a different container, such as a well in a multi-well plate, by employing a pneumatic clamp 1002 that is attached to a swing arm 1003 and grips the vessel 1001. FIG. 23B shows a top view of the clamp 1002 and swing arm 1003 of the embodiment. As illustrated in FIG. 23C, the swing arm 1003 accelerates the vessel 1001 through an arc trajectory and impacts a hard stop 1004 which causes the solids 1000 to exit the open-faced vessel 1061 and enter a target well 1006 in a multi-well plate 1007. The position of the target well 1006 is located by a pair of x and y linear actuators 1008 to be directly below the stopped-position of the vessel 1001.

Figure 24:
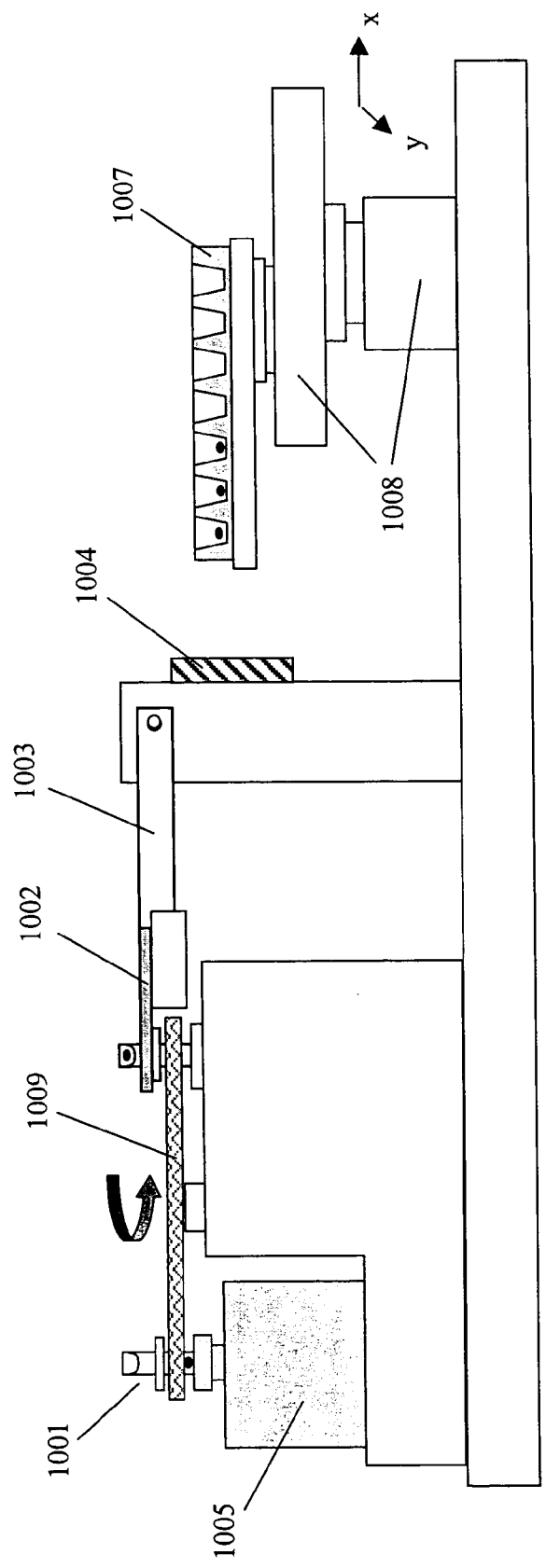
FIG. 24 illustrates a method of increasing the throughput of the transfer process by incorporating a carousel with two or more stations.

To increase the process throughput of the swing-arm embodiment, a carousel 1009 can be incorporated, as shown in FIG. 24. The carousel 1009 rotates two or more vessels 1001 between the microbalance 1005 for weighing and the position of the pneumatic clamp 1002 for transfer. As a result, transfer and weighing can occur simultaneously.

Figure 25A:
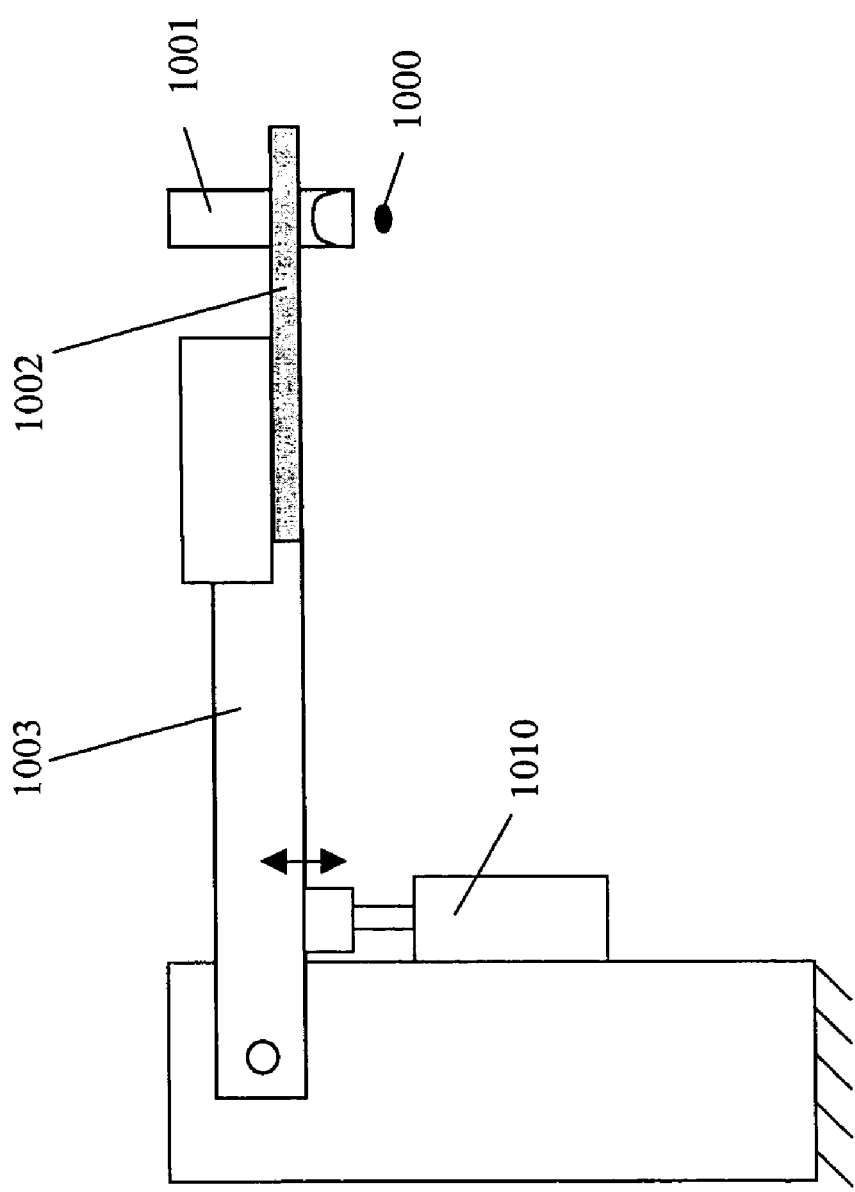
FIG. 25 illustrates a method of enhancing the release of solids from a container by applying external vibration to the swing arm or the container.
Figure 25B:
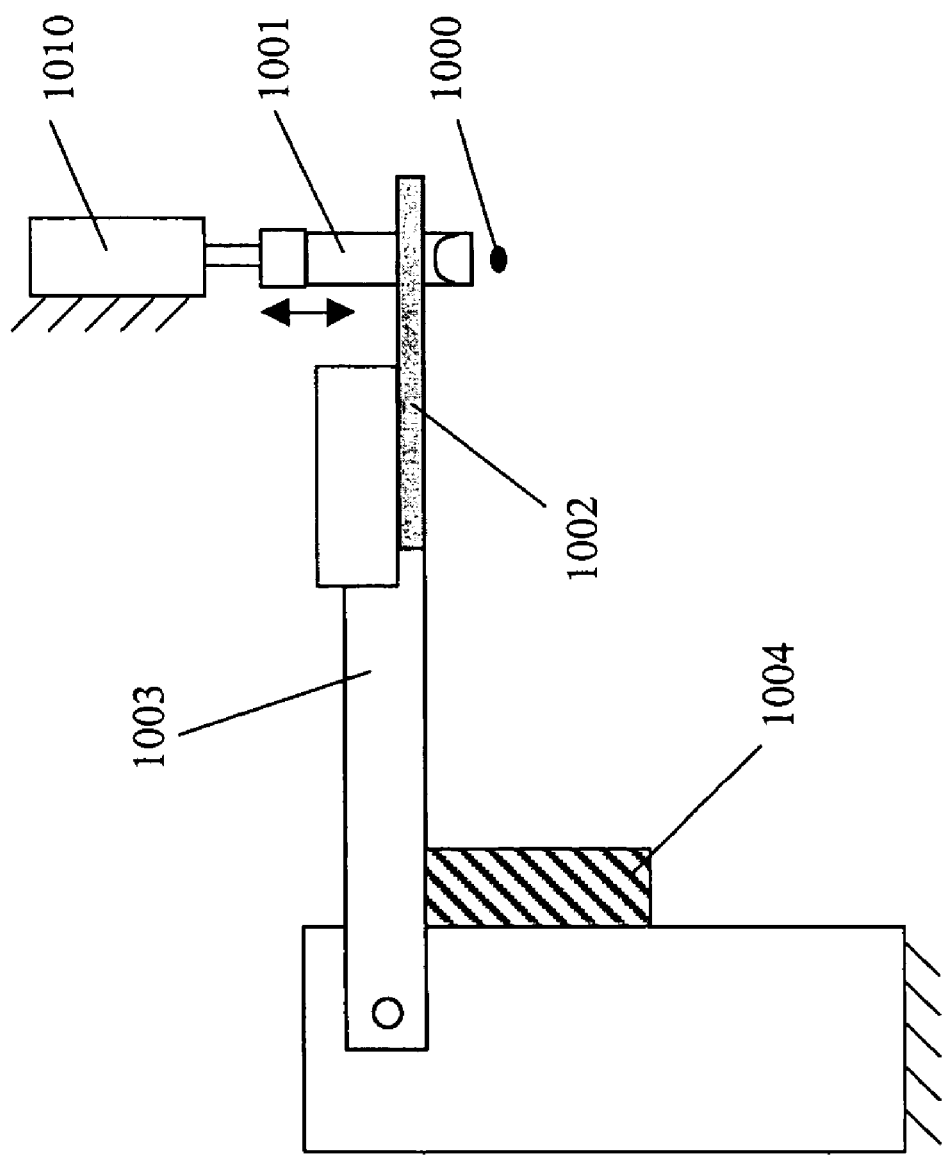
Figure 26A:
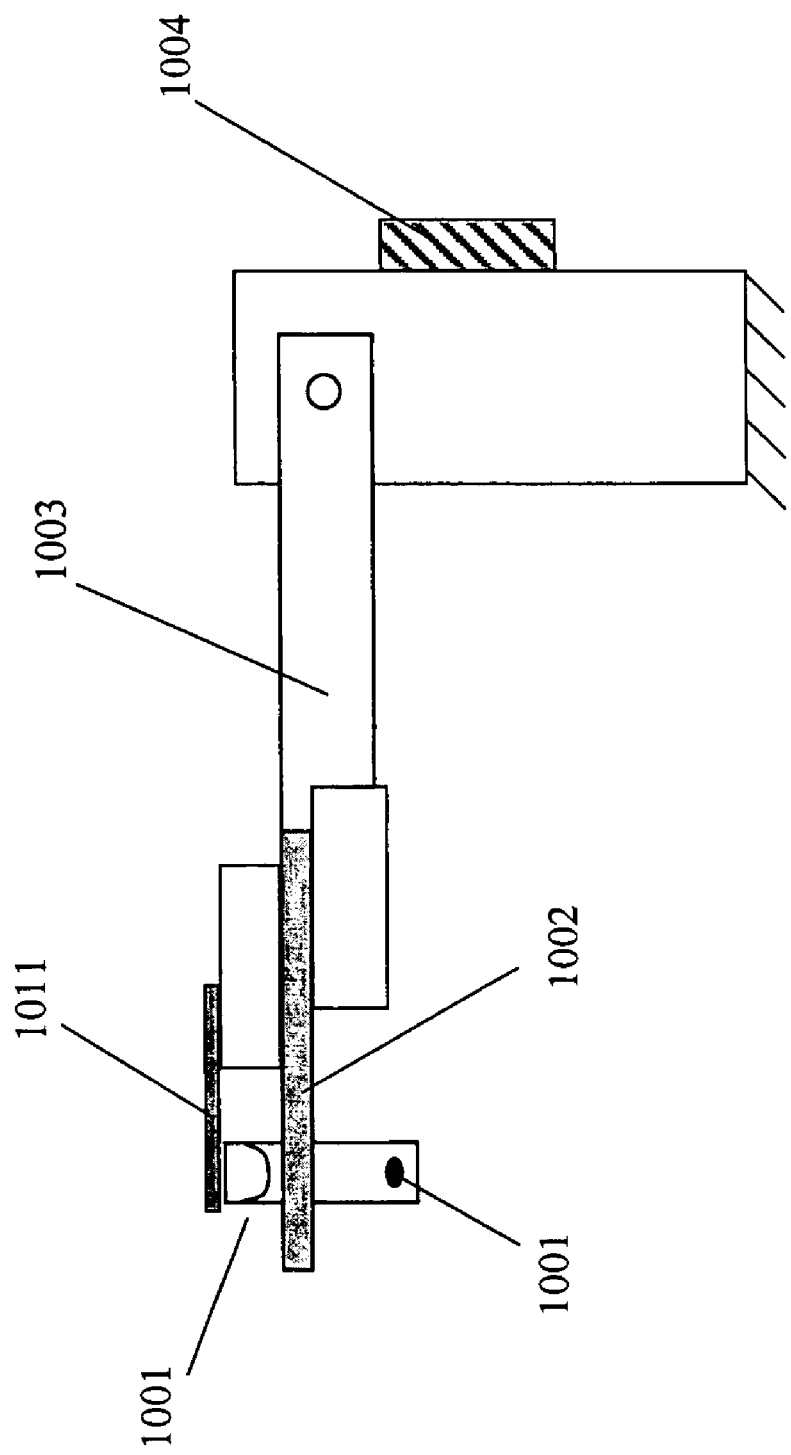
FIG. 26 illustrates a method of preventing the premature release of solids from a container by incorporating a retractable seal on the container.
Figure 26B:
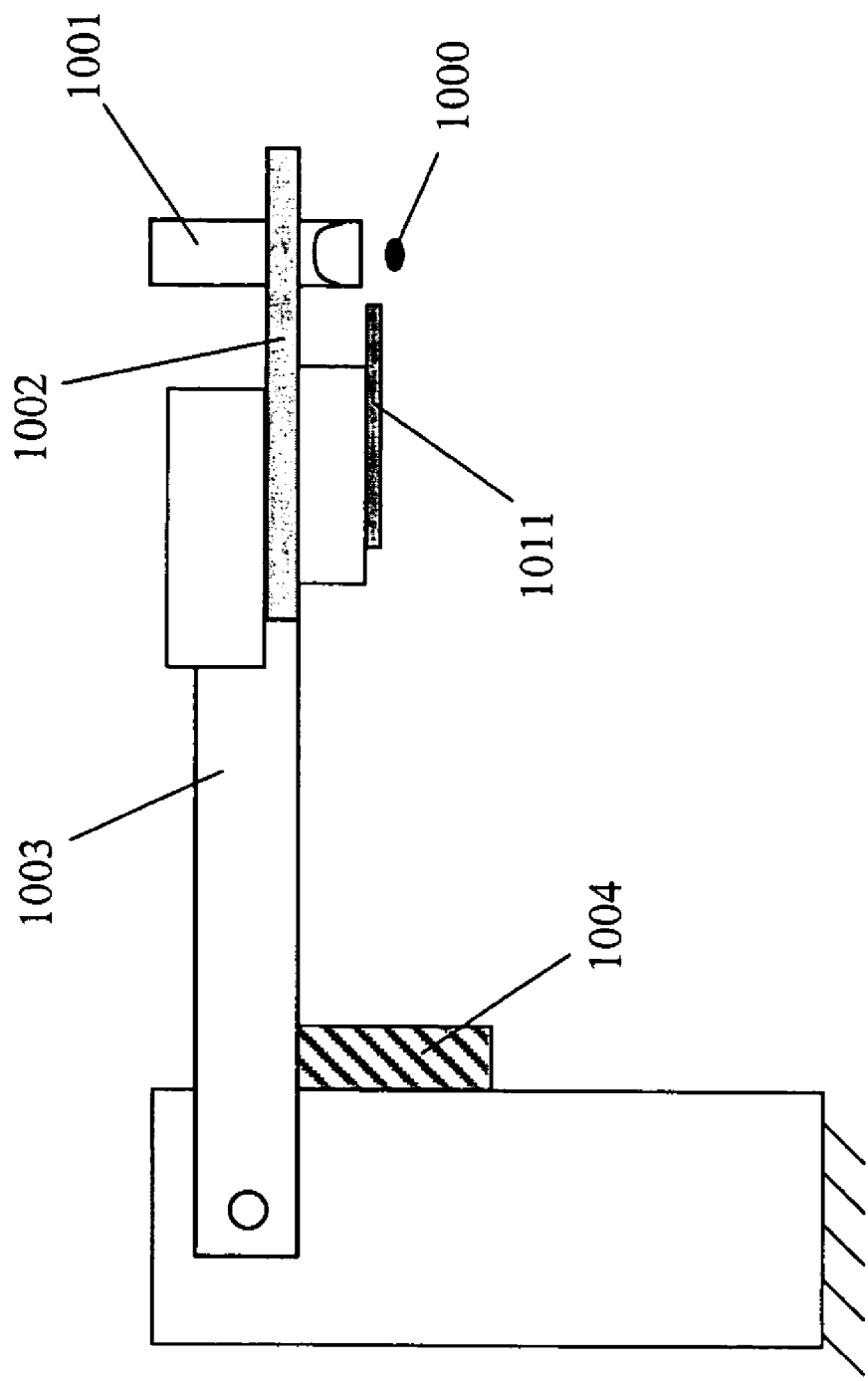

To enhance the release of solids from the vessel 1001 in the swing-arm embodiment, a vibrating actuator 1010 can be incorporated to apply repeated taps either to the swing arm 1003 as shown in FIG. 25A, or directly to the vessel 1001 as shown in FIG. 25B. The frequency of the vibration would typically be between about 1 Hz and about 50 kHz. To prevent pre-mature release of the solids 1000 from the vessel during the swinging motion, a retractable shield 1011 can be placed over the open-faced vessel 1001 as shown in FIG. 26A, and retracted just prior to dispense as shown in FIG. 26B.

Figure 27:
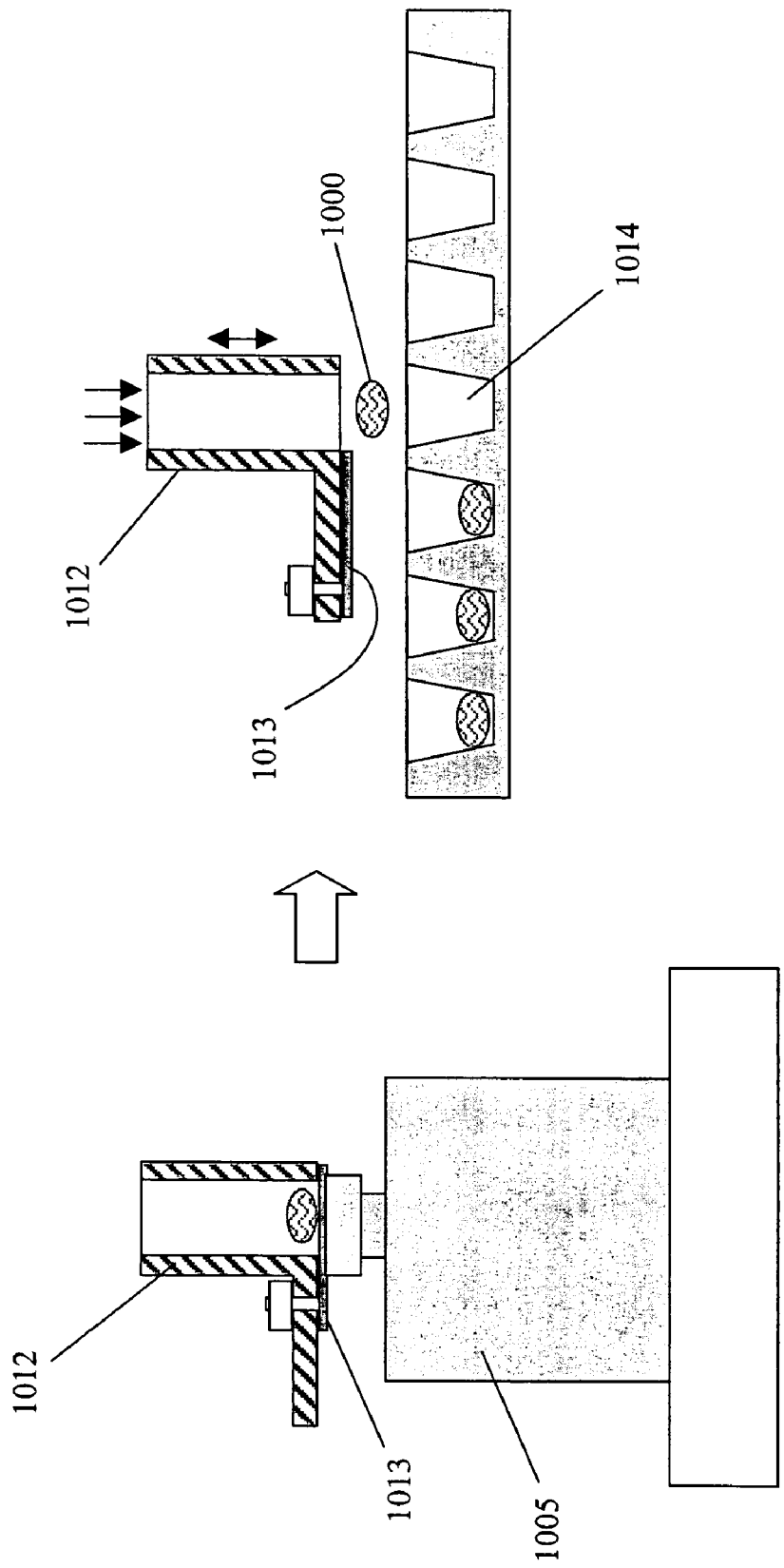
FIG. 27 illustrates a method of transferring solids from one container into another by utilizing a container with a retractable bottom plate.

An example of an alternative method and apparatus to transfer solid content from one container to another utilizes a container 1012 that can be weighed by a microbalance 1005 as shown in FIG. 27. The container 1012 incorporates a retractable bottom plate 1013 that can be removed to release the solids 1000 into a receiving container 1014. To enhance the solids release from the container 1012, the container can be shaken or impacted with an actuator, or a pulse of gas can be applied through the container.

Figure 28A:
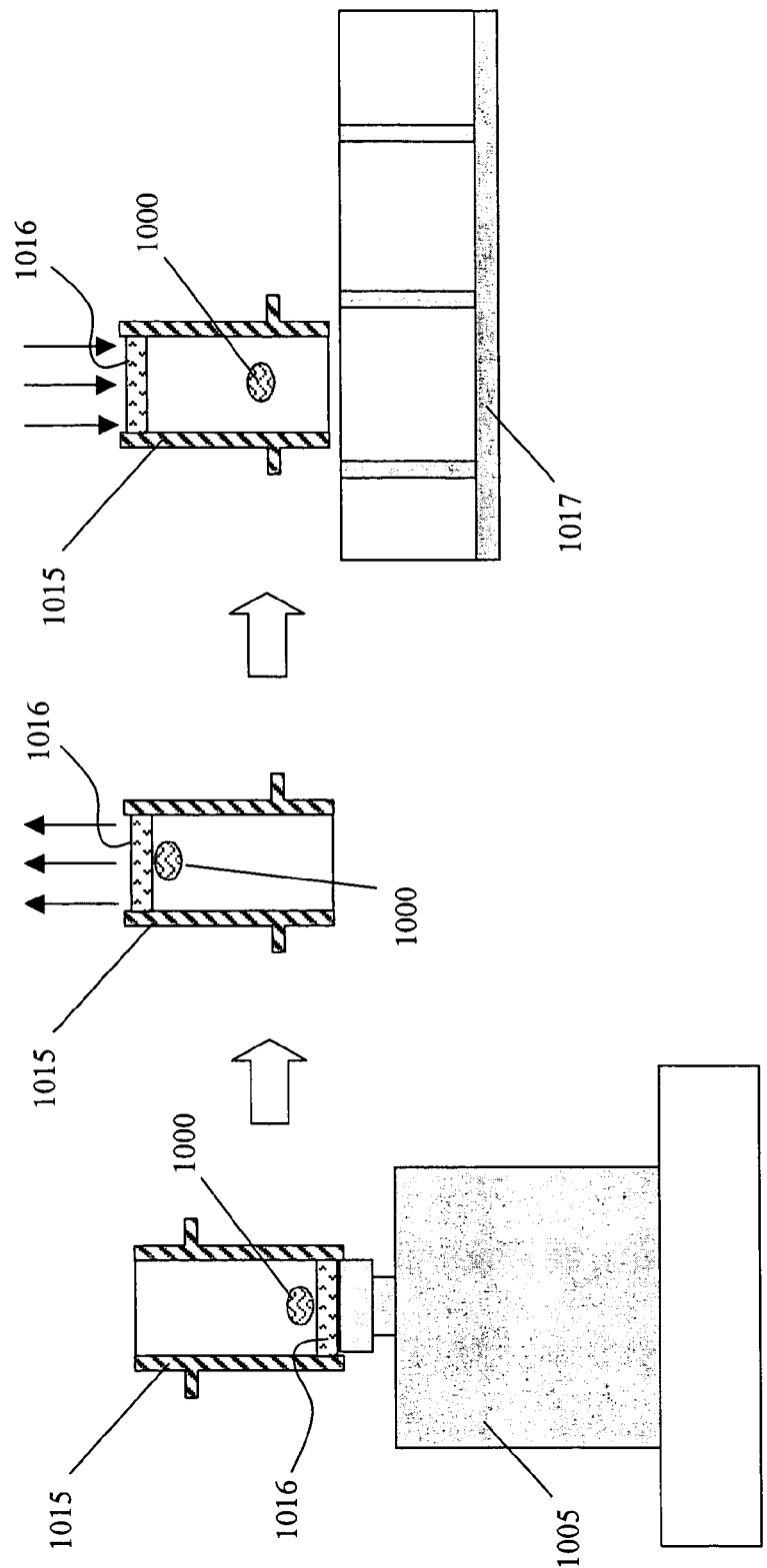
FIG. 28 illustrates a method of transferring solids from one container into another by utilizing a container with a filter plate.
Figure 28B:
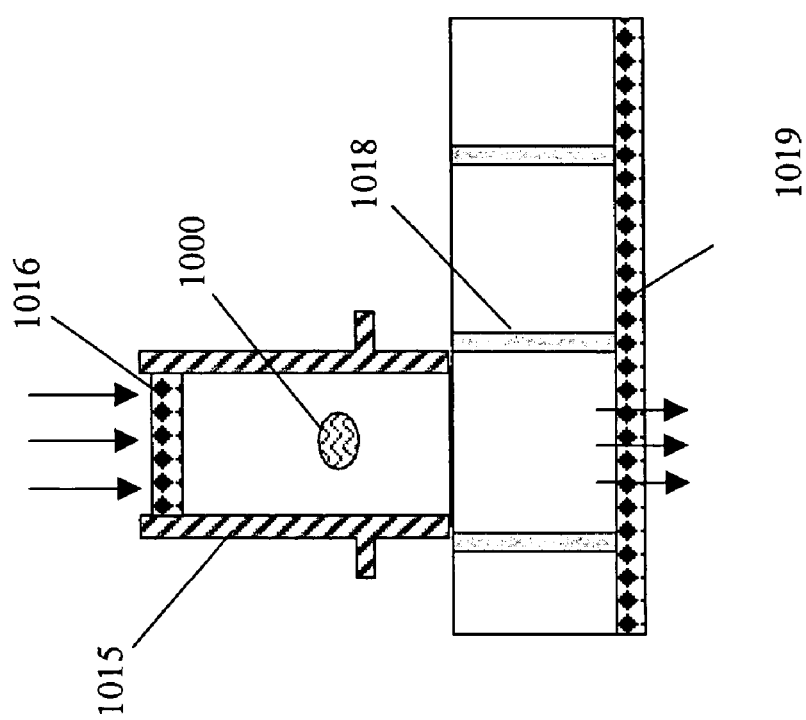

Another example of a method and apparatus to transfer solids content from one container to another comprises a container 1015 that can be weighed by a microbalance 1005 as shown in FIG. 28A. The container 1015 incorporates a gas permeable bottom plate 1016. To transfer the solids content 1000, vacuum pressure is applied through the bottom plate 1016, the container 1015 is inverted, and then, the vacuum pressure is removed or positive pressure is applied through the bottom plate to release the solids 1000 into the receiving container 1017, as shown in FIG. 28A. To enhance the solids release from container 1015, a receiving container 1018 can incorporate its own gas permeable bottom plate 1019 which allows a continuous current of gas to run through both containers, as shown in FIG. 28B.

Figure 29:
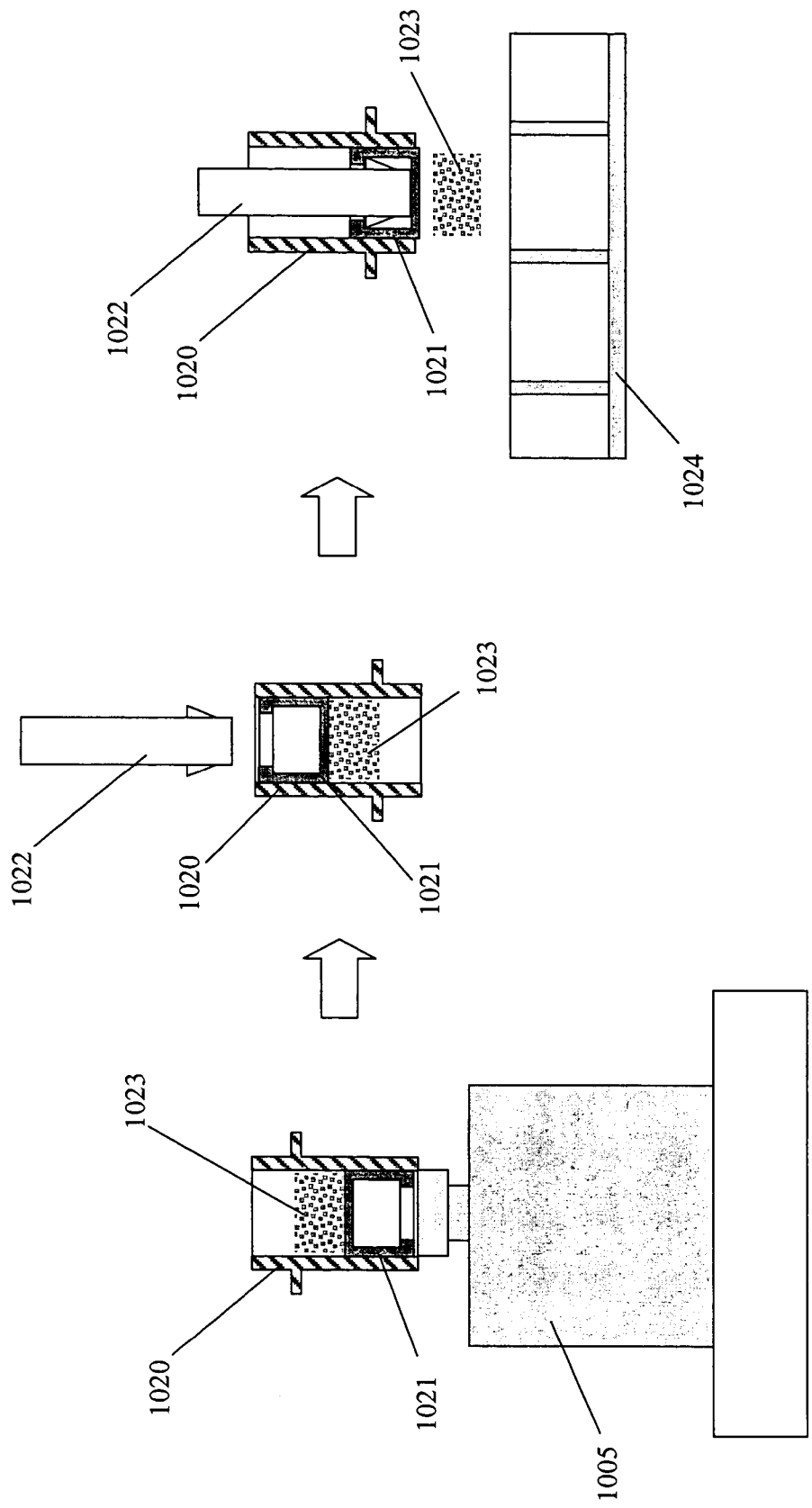
FIG. 29 illustrates a method of transferring solids from one container into another by utilizing a container with an internal piston.

In some cases, the solids content of a container may be strongly adhered to the container walls and require a release force greater than gravity, low-pressure gas, or inertial vibration. In such cases, an example of a method and apparatus to transfer the solids content from one container to another is illustrated in FIG. 29. The solid-containing container 1020 can be weighed by a microbalance 1005 and is designed to allow an internal piston 1021 to slide through the container. The container 1020 is inverted and a pin 1022 is used to push the internal piston 1021 and solids content 1023 through the container 1020 and into a receiving container 1024.

Figure 30:
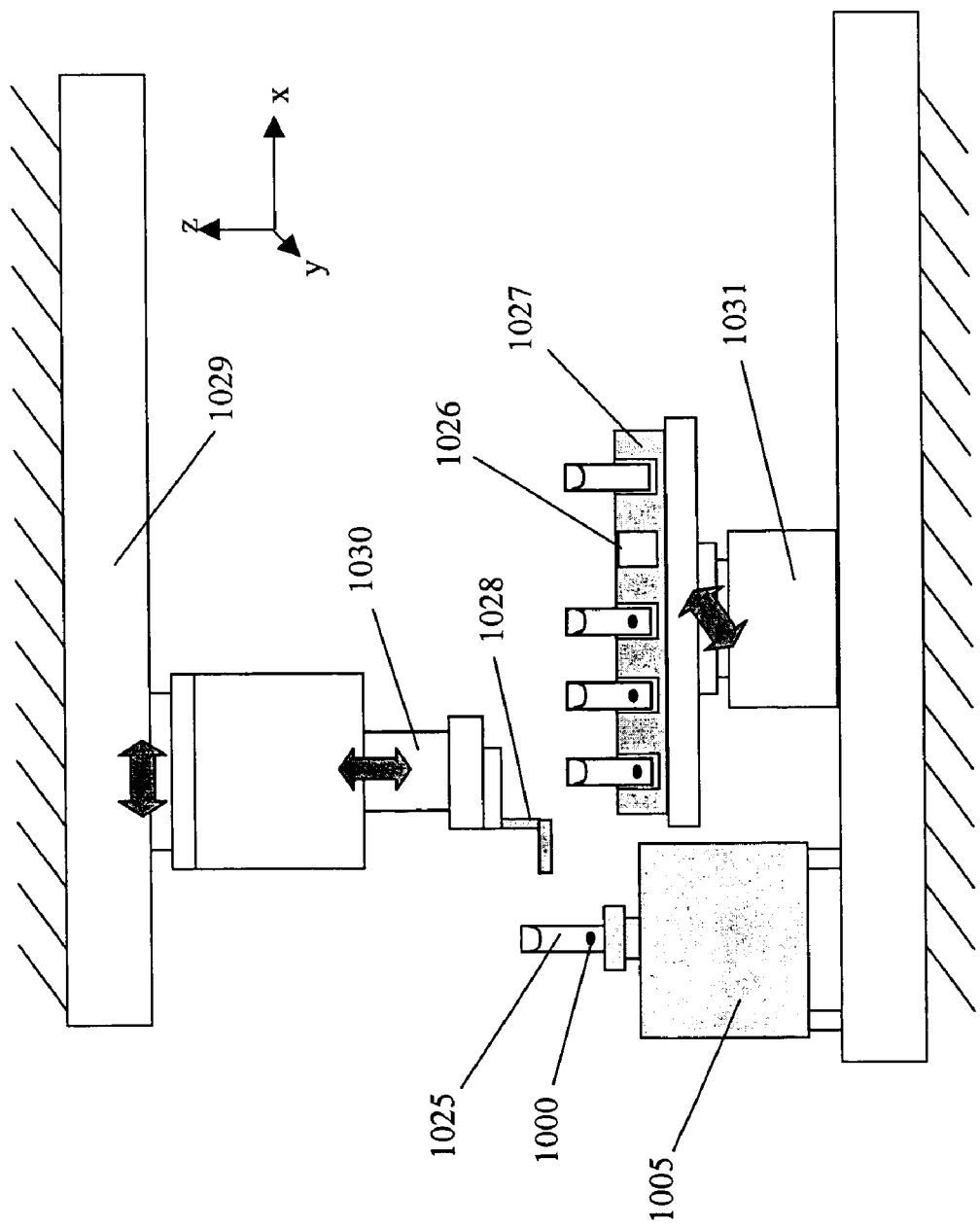
FIG. 30 illustrates a method of placing a container holding solids into another container to achieve a two-dimensional array of containers.
Figure 31:
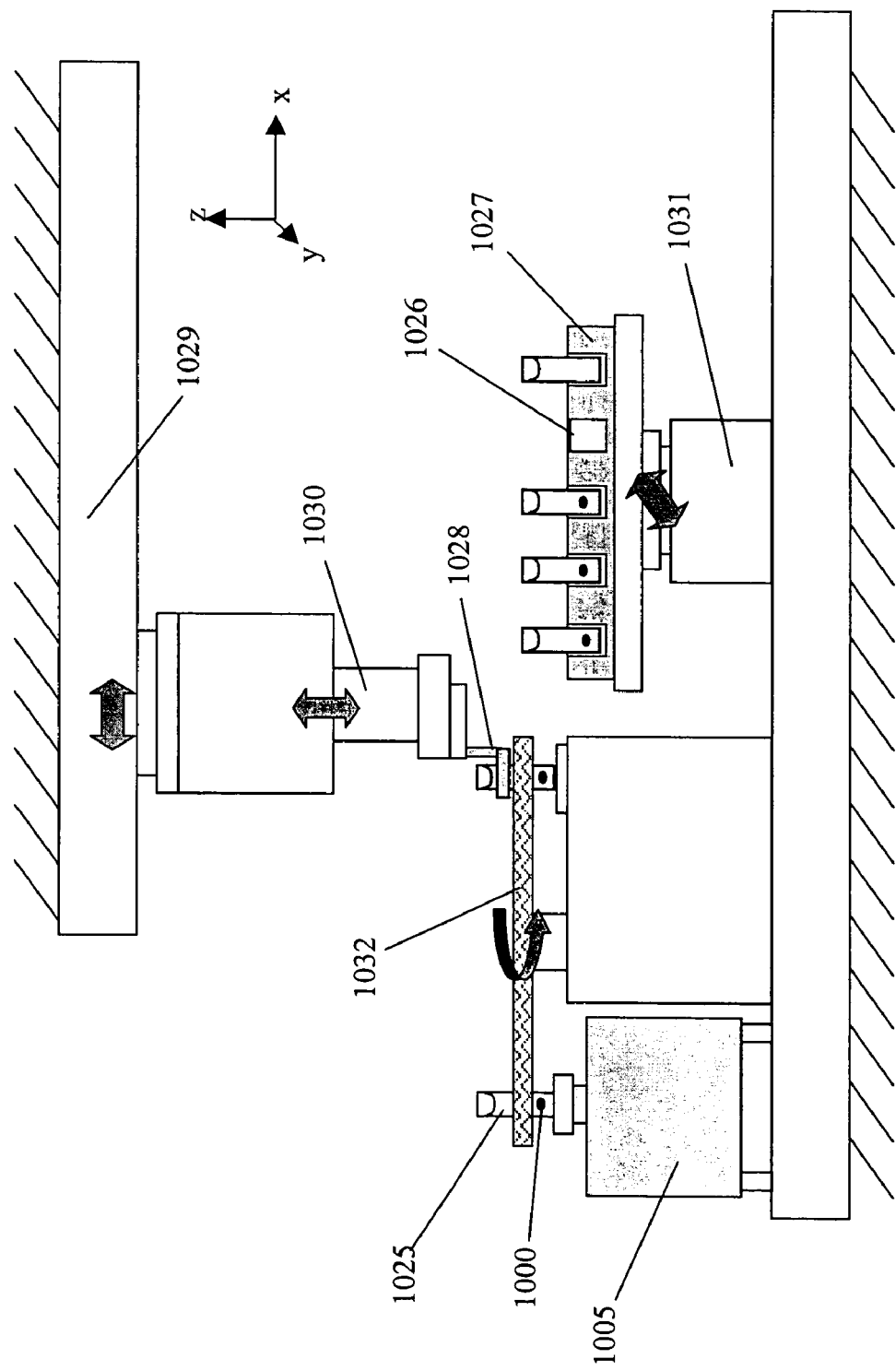
FIG. 31 illustrates a method of increasing the throughput of pick-and-placing containers by incorporating a carousel with two or more stations.

In a separate method and apparatus, the solids are not removed from their original container during transfer to expedite the process. As shown in FIG. 30, the solid 1000 is transferred into a two-dimensional array format by utilizing a vessel 1025 that can be weighed by a microbalance 1005 and that fits inside a well 1026 in a receiving plate 1027 that has a two-dimensional array of wells. The vessel 1025 is manipulated by a robot arm or a pneumatic gripper 1028 mounted to x-linear stage 1029 and z-linear stage 1030. The receiving plate 1027 sits on a y-linear stage 1031. For certain applications, the vessel is designed to fit completely inside the well such that the receiving plate can be sealed with a conventional plate seal (e.g., a pressure-adhesive film, heat-activated film, or rubber capmat) for further processing of the solids. As shown in FIG. 31, the throughput of this transfer process can be enhanced by incorporating a carousel 1032 that allows vessels to be weighed and transferred simultaneously.

Example 7

Mixing Small Amounts of Solids

In applications such as high-throughput preformulation screening of drug compounds, it is necessary to mix small amounts of different powders, with the total sample volume typically less than 1 mg. Mixing achieves intimate particulate contact between compounds such that any resulting chemical or physical interactions can be analyzed. Several methods and apparatuses to mix small amounts of solids are described here.

Figure 32A:
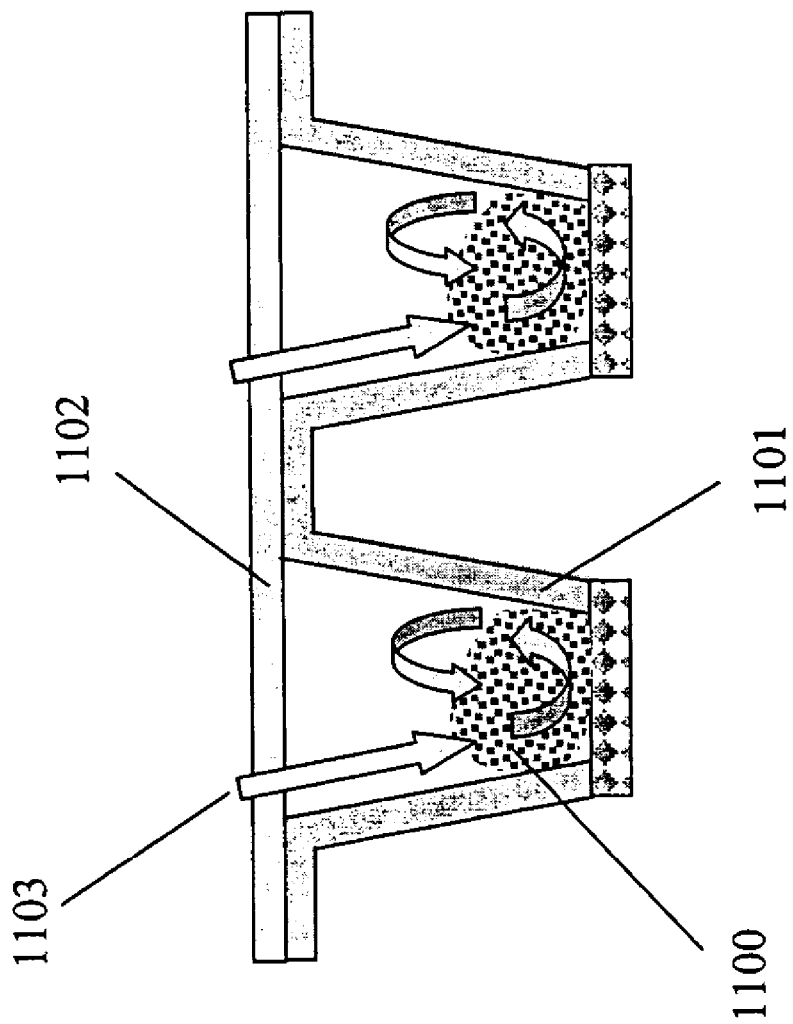
FIG. 32 illustrates a method of mixing solids in a sealed container using turbulent gas jets.
Figure 32B:
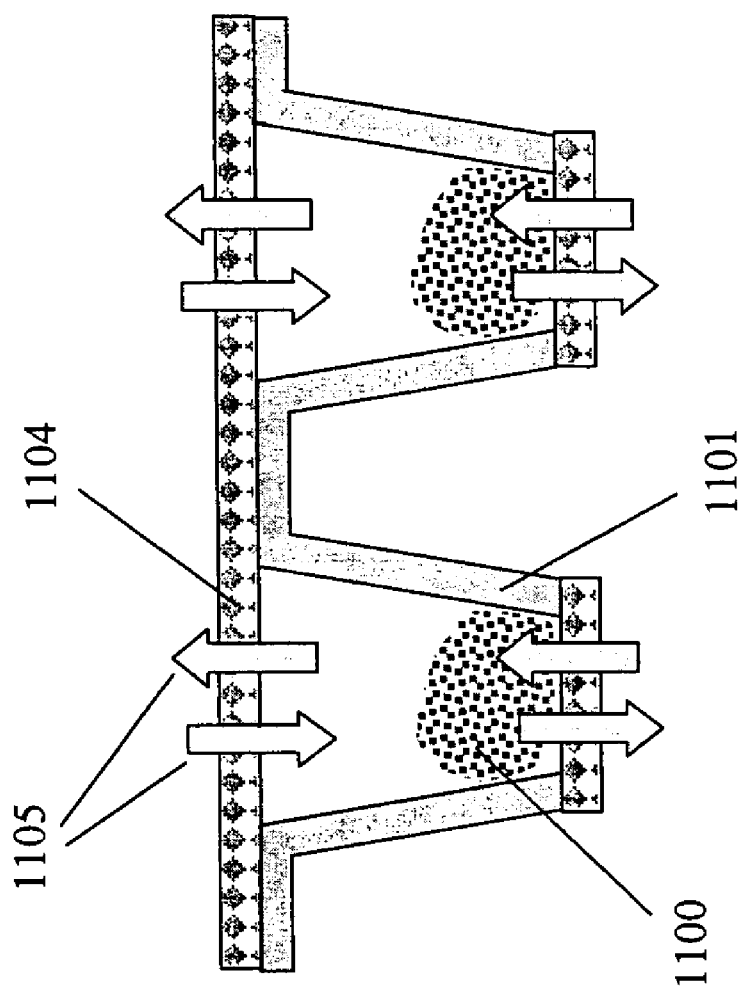

In a specific method and apparatus as shown in FIG. 32A, the solids 1100 (e.g., powders) are contained in a conventional multi-well plate 1101 with filter-bottom wells (e.g. Unifilterm plate by Whatman, Clifton, N.J.). The top of the microplate is sealed with a lid 1102 that seals each well independently from each other (e.g. Capmats by Whatman). The lid is pierced to inject gas into a well. One well can be mixed at a time, or several wells in parallel, or all the wells in the plate can be mixed simultaneously. By directing a jet of gas 1103 into each well, turbulent air flow is created and the powders are forced to mix. The filter at the bottom of each well allows the gas to escape while retaining the powders. Alternatively, it is also possible to seal the top of a multi-well plate 1101 with a filter plate 1104, so that short bursts of gas 1105 can be cycled back and forth, across each well to mix the solids 1100, without piercing the plate 1104 as shown in FIG. 32B.

In a separate method and apparatus, the powders are contained in a commercial microplate or individual vials carried in a block. The vials are sealed with screw, snap, or crimp caps and clamped down to the carrier block, or each well in the microplate is sealed with a lid. After sealing the powder receptacles, the powders are mixed by shaking or vibrating the microplate or carrier block at high or low frequency for a period of time. The microplate or carrier block can also be rotated around different axes to achieve powder mixing. To enhance mixing, a small magnetic stirrer or spherical ball coated with a chemically-inert material can be placed into each well or vial. After sealing the powder receptacles, the powders are mixed by either shaking the microplate/carrier block which causes the internal ball to mix the powders, or by shaking the magnetic stirrer with an oscillating magnet.

Figure 33:
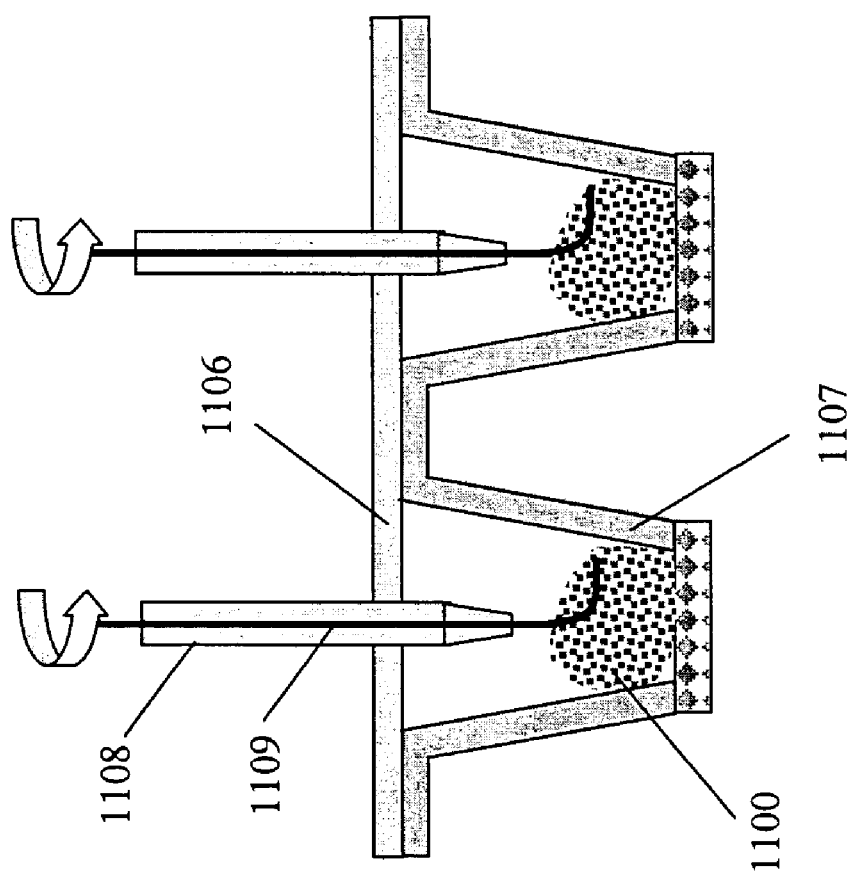
FIG. 33 illustrates a method of mixing solids in a sealed container using rotating wire.
Figure 34:
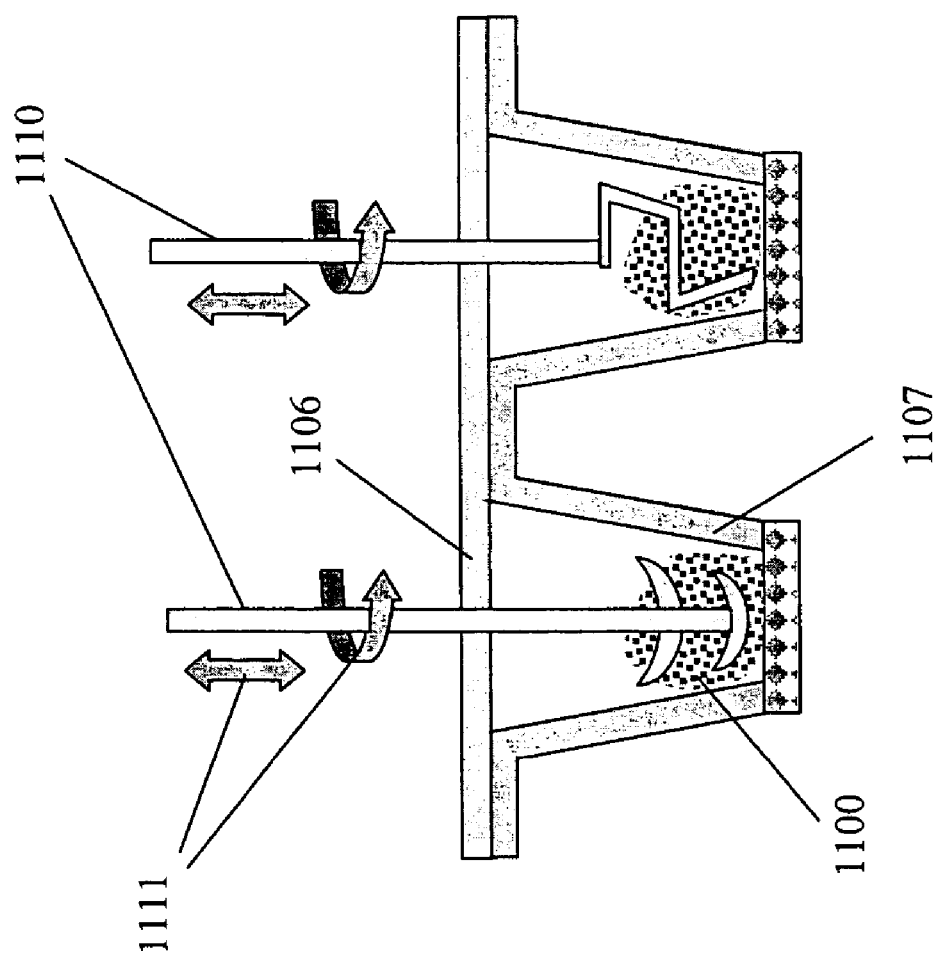
FIG. 34 illustrates a method of mixing solids in a sealed container using rotating blades.

A similar method and apparatus for mixing involves using a pierceable seal 1106 on top of microplate 1107 or vial and inserting a flexible wire 1109 into each receptacle, as shown in FIG. 33. The wire 1109 can be sheathed in a stationary housing 1108 while a motor spins the wire 1109 to mix the powders 1100. Various designs of stirrer blades 1110 and blade motions 1111 can be utilized to mix the powders, as shown in FIG. 34. After mixing, the stirrer wire 1109 or blade 1110 can be removed from the receptacle and cleaned. If the powder level in each receptacle is shallow enough, it is possible to mix the powders without sealing the receptacle. One well or vial can be mixed at a time, or several wells or vials can be mixed simultaneously.

Figure 35:
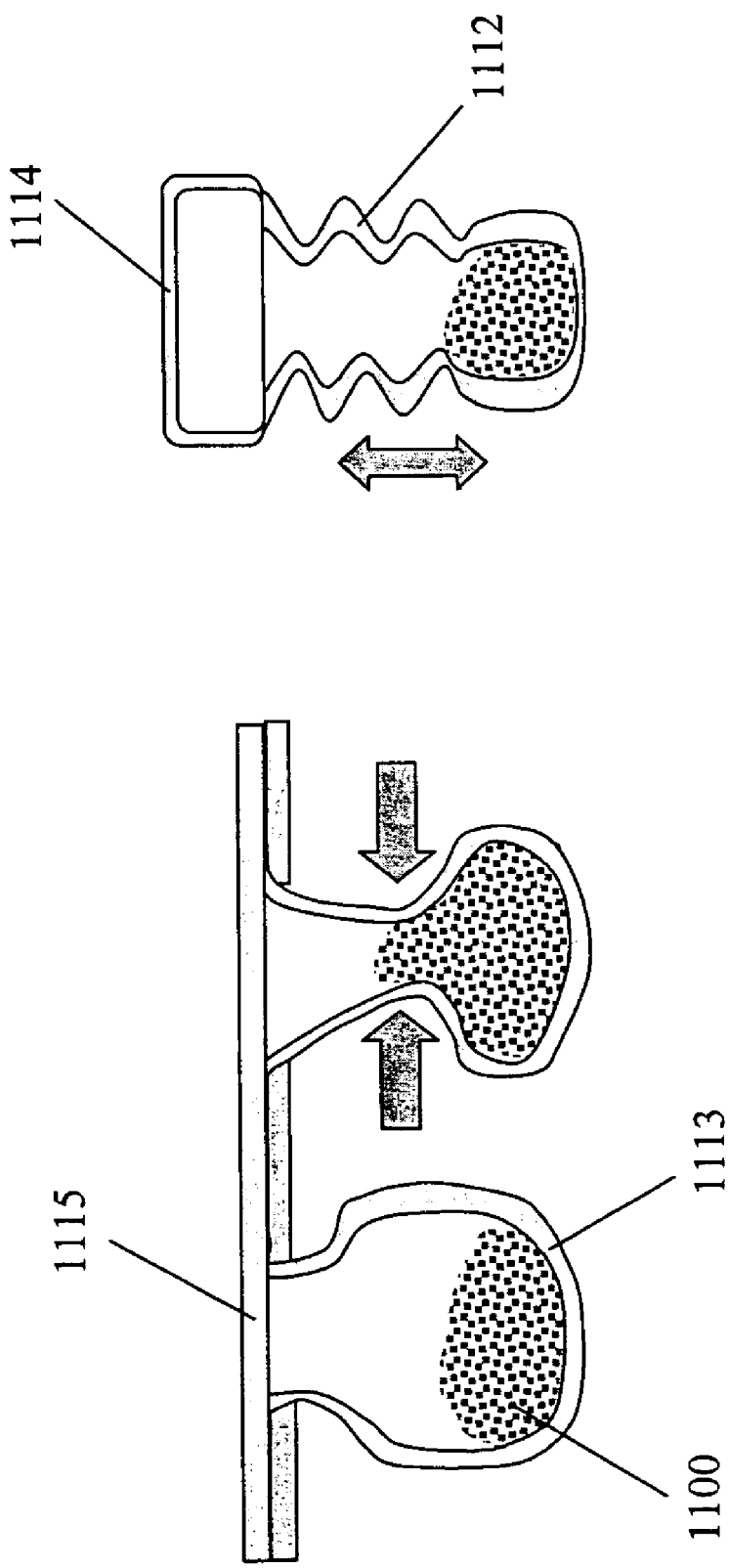
FIG. 35 illustrates a method of mixing solids in a sealed container by compressing the walls of the container.

FIG. 35 shows another example of mixing where the powder 1100 is contained in compressible vials 1112 or a microplate fabricated with compressible wells 1113. For example, the vials or wells can be fabricated from an elastic material such as silicone rubber or they can be fabricated with collapsible plastic bellows. The vials are sealed with a flexible or gas-permeable cap 1114, while the top surface of the microplate is sealed with a filter plate 1115 to allow air to escape. The vials or wells are squeezed repeatedly in the same or different directions to mix the powders.

Figure 36:
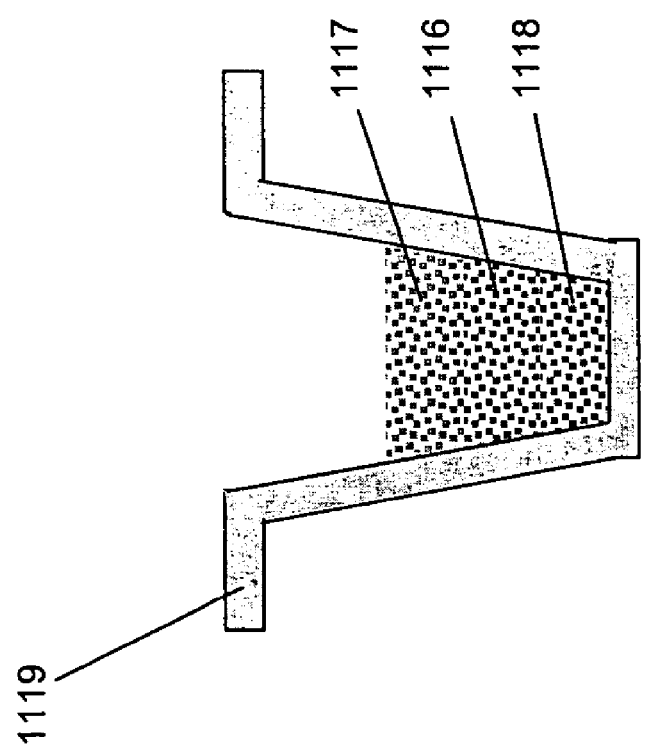
FIG. 36 illustrates a method of mixing solids by dispensing alternate layers of different solids into a container.

In another example, instead of employing an active means of mixing compounds, it is possible to achieve particulate contact between different compounds by layering the powder dispensed inside each receptacle 1119, as shown in FIG. 36. This method would allow an active ingredient 1116 to interact with excipient 1117 and a different excipient 1118.

Example 8

Dispensing and Weighing Solids in a Two-Dimensional Array Format with a Conventional Microbalance Previously described in this invention are examples of methods and apparatuses to manipulate small amounts of powder. For applications such as high-throughput screening of drug compound stability, it is often desirable to dispense as well as weigh controlled amounts of solids rapidly and accurately without substantially affecting their form. Weighing small amounts (e.g., amounts less than about 5 mg, 2.5 mg, 1 mg, 750 micrograms, 500 micrograms, 250 micrograms, 100 micrograms, 50 micrograms, 25 micrograms, 10 micrograms, 5 micrograms, or 1 microgram) of solid on a conventional microbalance (e.g., SC2 Ultra Micro by Sartorius) restricts the total mass weighed (e.g., less than 2 g) in order to achieve sufficient mass resolution (e.g., 0.1 microgram readability). In other words, during mass measurement on a microbalance, the solids should be contained by a lightweight container. However, further processing of those solids may require them to be in a two-dimensional array format, such as a multi-well plate which is too massive for a precision microbalance.

Figure 37:
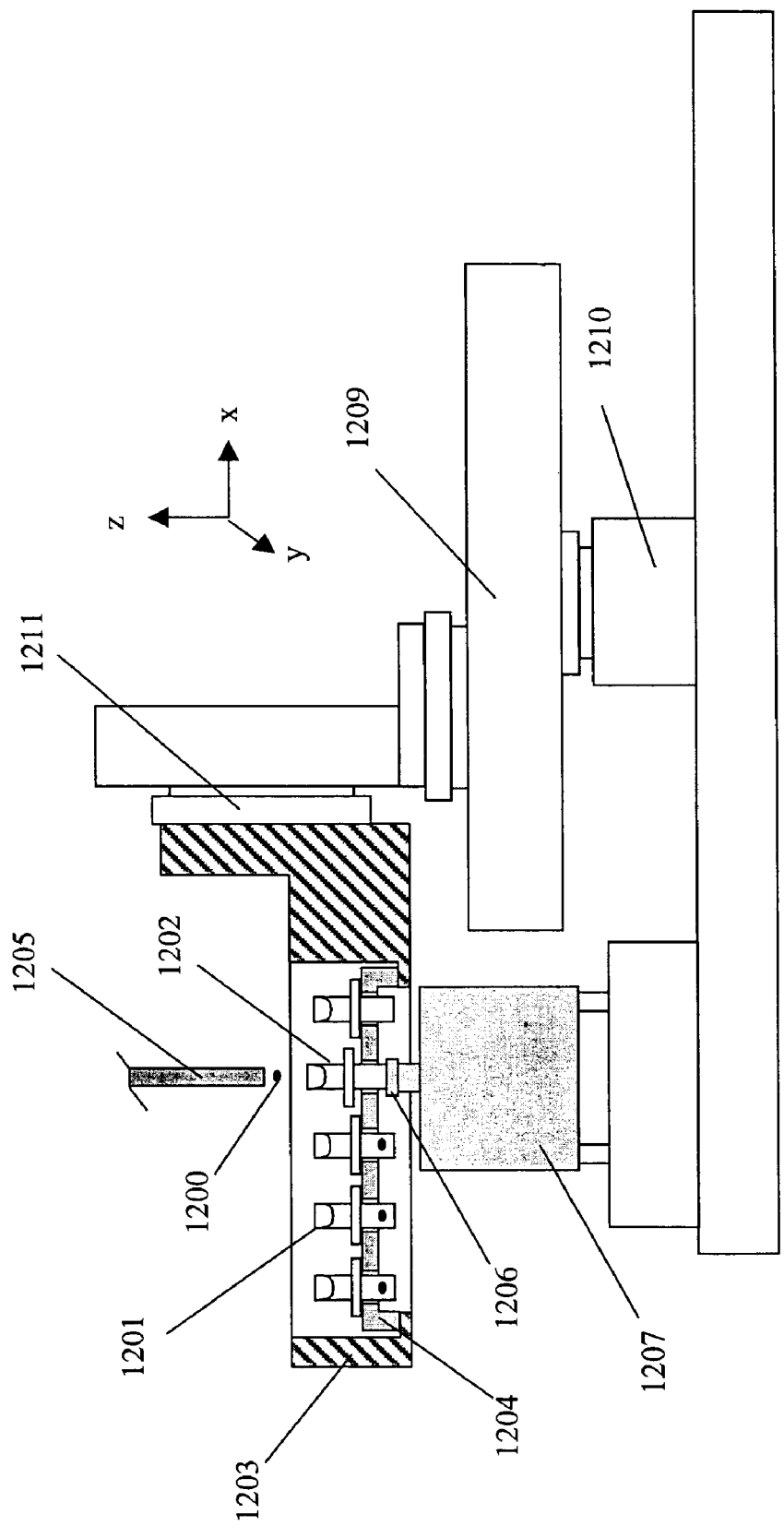
FIG. 37 illustrates a method of weighing individual samples as part of a two-dimensional array of samples.

FIG. 37 illustrates a method and apparatus that enables a controlled amount of solid 1200 to be dispensed by a dispensing device 1205 directly into a two-dimensional array format and weighed by a precision microbalance 1207. The apparatus comprises a cradle 1203 that supports a tray 1204 that has a two-dimensional array of through-holes. Each through-hole supports a low-mass container 1201 such that the container can slide in and out of the hole easily. The cradle 1203 is attached to a vertical actuator 1211 which is mounted to an x-linear actuator 1209 and a y-linear actuator 1210. The x and y actuators position the tray 1204 such that a desired container 1202 is directly above the weigh platform 1206 of the microbalance 1207. Then, the vertical actuator lowers the tray 1204 such that the desired container 1202 is supported by the weigh platform 1206 and no longer in contact with the tray 1204. As a result, a controlled amount of solid 1200 can be dispensed into the desired container 1202 and weighed individually by the microbalance 1207 while it is part of a two-dimensional array. After the desired container 1202 is weighed, it is removed from the microbalance 1207 by employing the vertical actuator 1211 to lift the tray 1204 such that the container 1202 is supported by the tray again.

Example 9

Dispensing and Weighing Solids with an Integrated Mass Sensor

Previously described in this invention are the limitations of weighing small amounts (e.g., amounts less than about 5 mg, 2.5 mg, 1 mg, 750 micrograms, 500 micrograms, 250 micrograms, 100 micrograms, 50 micrograms, 25 micrograms, 10 micrograms, 5 micrograms, or 1 microgram) of solid particles with a conventional microbalance (e.g., SC2 Ultra Micro by Sartorius). The current example describes novel methods and apparatuses that can dispense and weigh solids without a conventional microbalance. A transfer device is used to capture and dispense a controlled amount of solid. Transfer devices of the present invention can comprise a coring tool as described in Example 1, micromechanical tweezers, or microelectrodes that attract particles using electric or magnetic fields. A mass sensor is designed to quantify the mass of the captured solids by measuring the mechanical response of the transfer device before and after the solids are captured. Similarly, the mass sensor can quantify the mass of dispensed solids by measuring the mechanical response of the transfer device before and after the solids are dispensed.

In general, the mechanical response of a structure to an applied input force exhibits a unique resonant frequency that is a function of its stiffness and mass. Therefore, the loading or unloading of solids onto a transfer device produces a proportional change in the resonant frequency of the device. As a result, the mass of the solids can be calculated from the measured shift in resonant frequency, assuming that the stiffness of the device does not change and that the solids are securely attached to the device. To increase the sensitivity of this measurement, the transfer device is preferably stiff and lightweight. Specific transfer devices of the invention are very small, and can be made using microfabrication techniques.

To generate a mechanical response from transfer device, a transient force is applied to the transfer device, preferably at a location away from the attached solids. This is done using any of a variety of motion transducers known in the art, such as a piezoelectric actuator, solenoid shaker, impact hammer, acoustic speaker, electrostatic comb drive, or similar means. Different excitation signals can be applied to the motion transducer, such as a sweeping sine wave, impulse, step, or noise inputs to cause the transfer device to resonate.

The mechanical response of the transfer device to the excitation is measured using any of a variety of instruments known in the art, such as a capacitance sensor, accelerometer, phase Doppler velocimeter, piezoelectric sensor, strain gauge, or similar means. Preferably, the sampling frequency of the motion sensor is at least two times faster than the resonant frequency of the transfer device to prevent aliasing. The motion sensor provides an analog voltage signal that corresponds to the movement of the transfer device. Commercial data-acquisition hardware and software is used to record and analyze the transient signal data to obtain a frequency spectrum of the transfer device's mechanical response. The frequency at which the device displays the maximum amplitude of vibration is its resonant frequency. If a piezoelectric transducer is used to impart motion to the transfer device, the resonant frequency of the piezoelectric transducer itself can be correlated to the added mass of attached particles. This can be accomplished with an oscillator circuit that takes advantage of the electrical impedance of resonance inherent to piezoelectric transducers.

Figure 38:
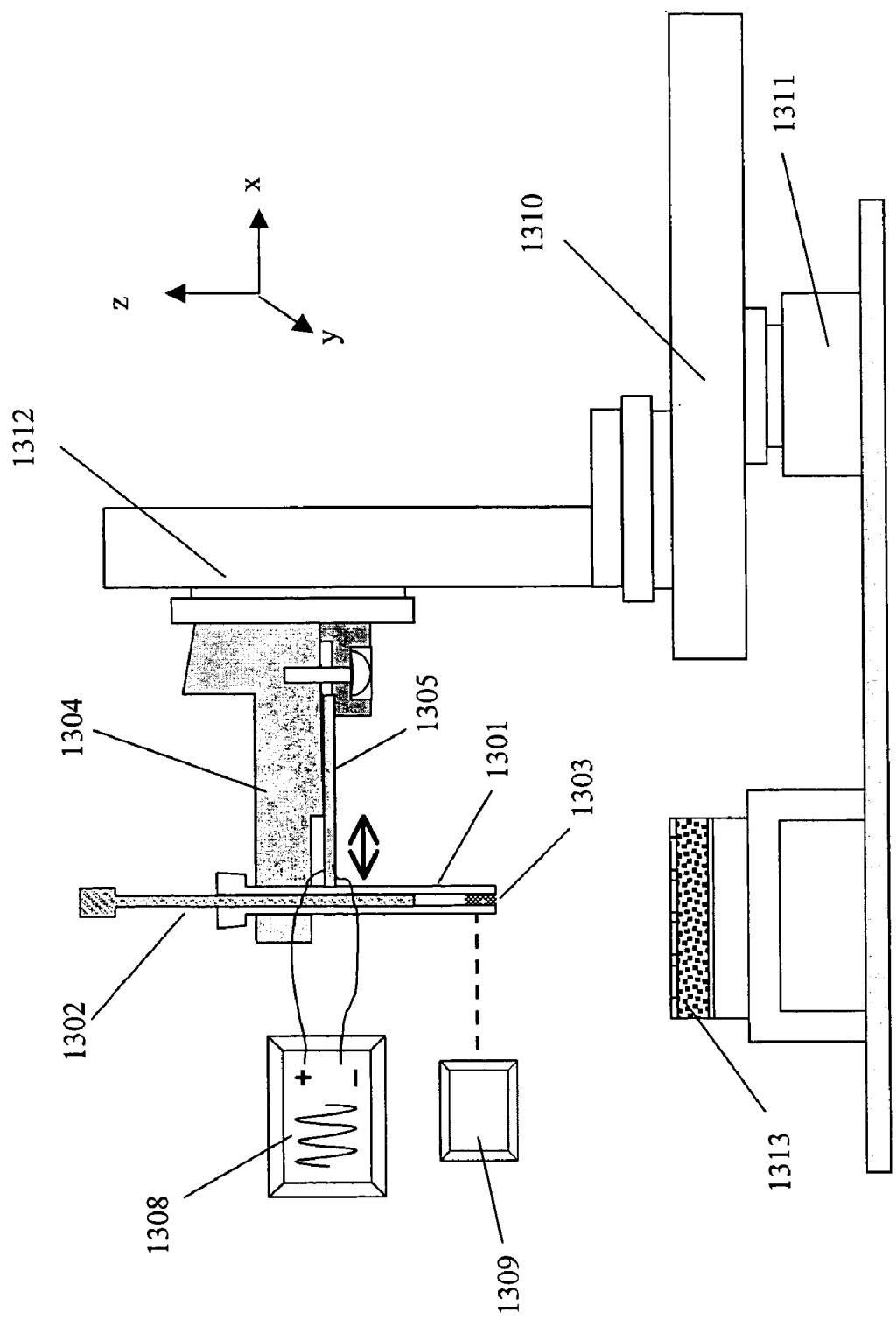
FIG. 38 illustrates a method of dispensing and weighing a plug of powder using a coring device and an integrated mass sensor.

FIG. 38 provides a general illustration of a particular embodiment of the invention, wherein a coring tool is utilized as the transfer device. The coring tool 1301 is a thin-walled stainless steel tube (25.5 standard gauge hypodermic tube, 9 mm in length). The coring tool 1301 contains an internal piston 1302 that is a stainless steel rod (0.34 mm in diameter, 10 mm in length) that slides through the tube to eject a plug 1303 of powder. The coring tool 1301 is securely mounted onto a fixture 1304 that is connected to a set of x- 1310, y- 1311, and z- 1312 linear actuators. The actuators manipulate the coring tool in and out of a powder bed 1313 to extract a plug of powder. Further details of the coring method and apparatus are given in Example 1.

Figure 39:
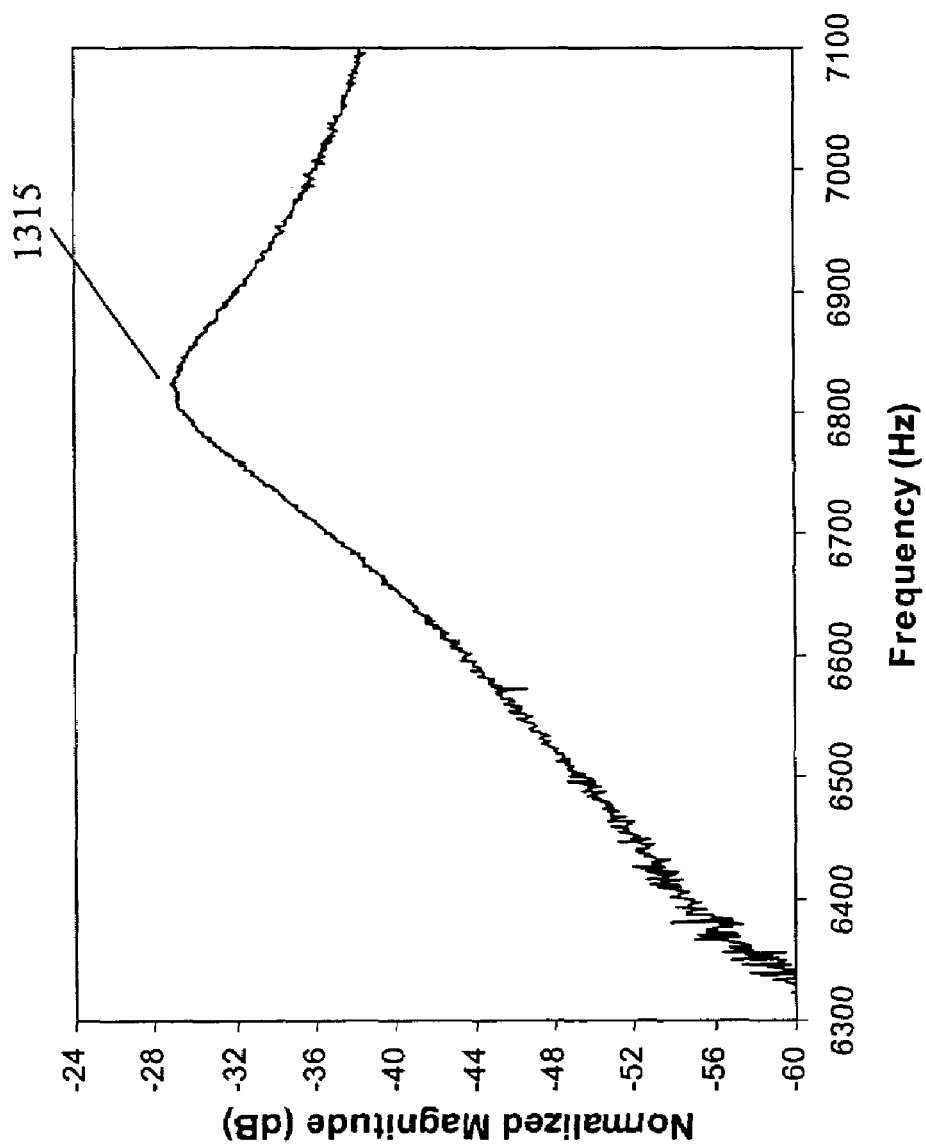
FIG. 39 illustrates a typical frequency spectrum of the mechanical response of a coring tube that is used to identify its resonant frequency.

In the embodiment shown in FIG. 38, a piezoelectric ceramic actuator 1305 (Piezo Systems, Cambridge, Mass., Part No. T220/A4-203Y) is affixed between the coring tube 1301 and the fixture 1304. When the internal piston 1302 is withdrawn from the tube 1301, a swept-sine voltage signal, 2 V peak-to-peak between 6.3 kHz and 7.1 kHz, is generated by a function generator 1308 (Model 33120A, Agilent, Palo Alto, Calif.) and applied to the piezoelectric actuator which causes the tube to vibrate. The displacement of the coring tube 1301 in the direction perpendicular to its length is measured with a laser displacement sensor 1309 (e.g., Model LC-2420 by Keyence Corp of America, Woodcliffe, N.J.). For each measurement, 12 consecutive frequency spectra are acquired using commerical data-acquisition hardware (Model #PCI-6052E DAQ board, National Instruments, Austin, Tex.) and customized software (LabVIEW™ Sound and Vibration Toolset, National Instruments, Austin, Tex.). The spectra are averaged linearly with 25% overlap to reduce spectral noise. FIG. 39 shows a typical frequency response of the coring tube when it is empty. The peak 1315 in the spectrum indicates that the resonant frequency of the tube is about 6.8 kHz.

Figure 40:
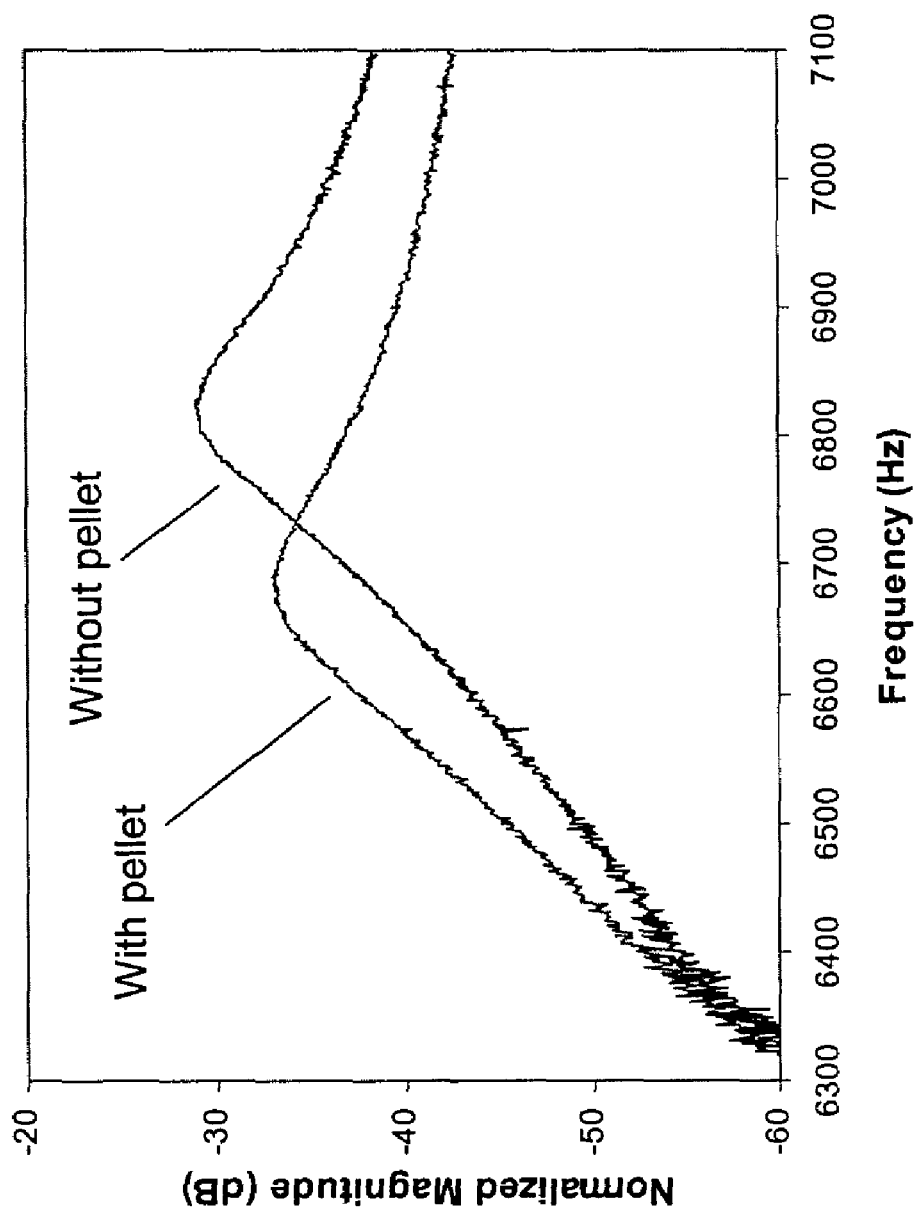
FIG. 40 illustrates a typical shift in the frequency response of the coring tube when a mass is ejected from the tube.
Figure 41:
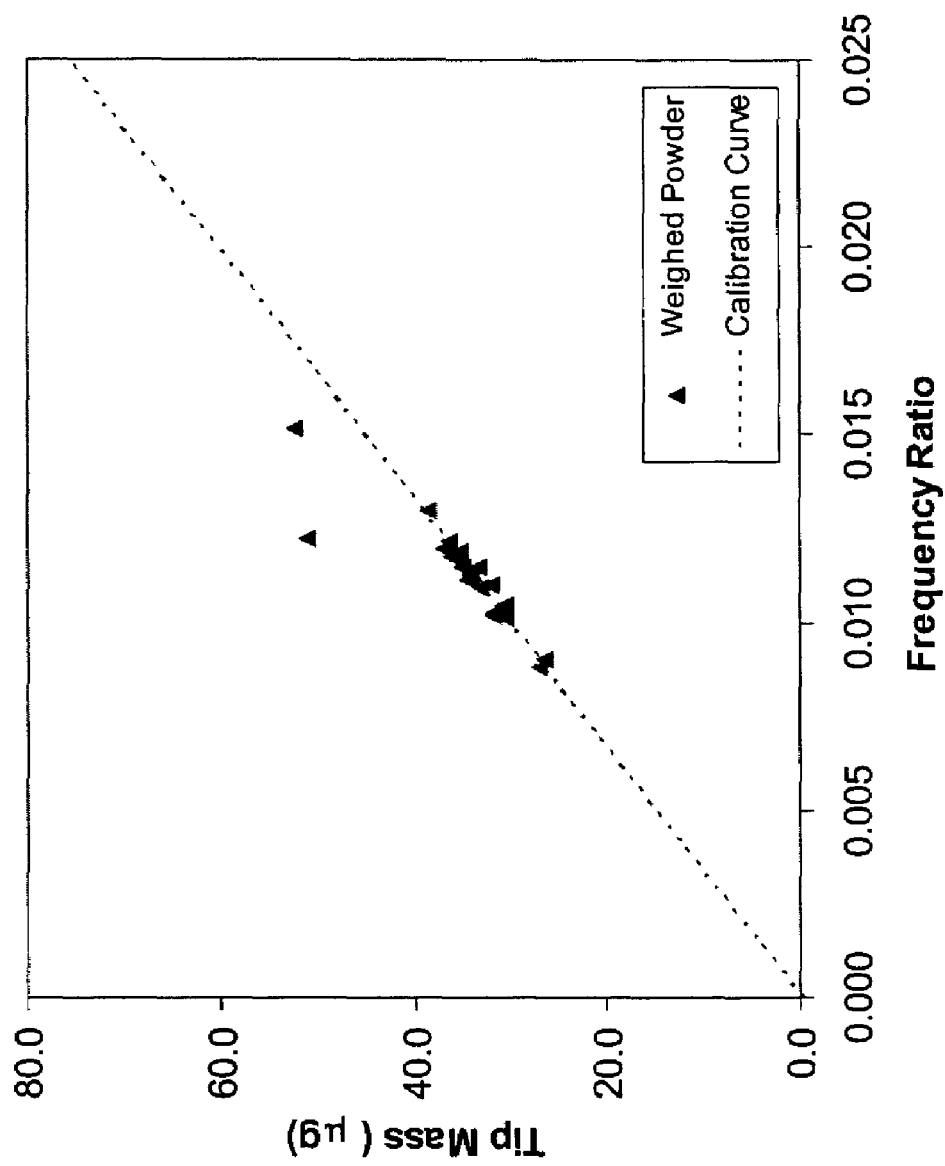
FIG. 41 illustrates a correlation between the measured frequency ratio and the amount of mass dispensed from a coring tube.

When the transfer device, or in this case the coring tube 1301, captures a small amount of solid or releases a small amount of solid, its resonant frequency will shift from its original value. For example, FIG. 40 shows a 140 Hz increase in the resonant frequency of a coring tube when a solid pellet weighing 62.2 micrograms is dispensed by the coring tube. Therefore, two frequency measurements are made to resolve the mass of the amount added or substracted from the transfer device. In this embodiment, the relationship between the shift in resonant frequency and the amount of mass dispensed by the coring tube is determined by a calibration procedure. During calibration, the shift in resonant frequency is measured for several different samples whose masses are determined off-line by a conventional microbalance. For the system described in FIG. 38, linear regression by least-squares fitting was performed on the calibration data to determine the following correlation (2):

$$m = 3040 \times (f_o - f_m)/f_o - 0.66 \qquad (2)$$

where m is the dispensed mass expressed in micrograms, and $f_m$ and $f_o$ are the resonant frequencies of coring tube expressed in Hertz, before and after the mass is dispensed, respectively. FIG. 41 illustrates strong agreement between the calibration curve and experimental data from weighed quantities of pharmaceutical powder, such as acetaminophen and naproxen, ranging from 26 micrograms to 38 micrograms.

Figure 42:
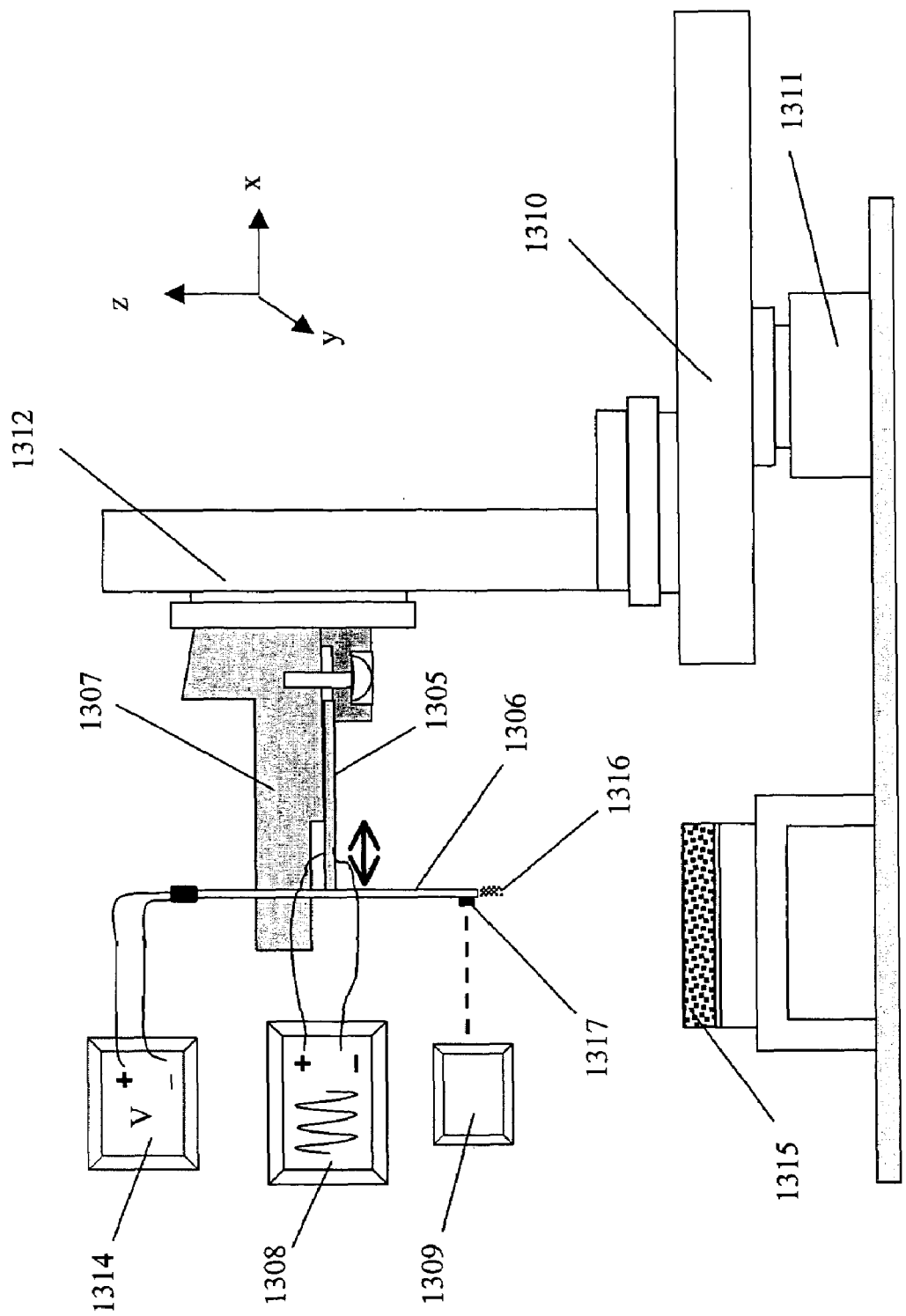
FIG. 42 illustrates a method of dispensing and weighing a plug of powder using an electrode assembly and an integrated mass sensor.

FIG. 42 illustrates another embodiment of the invention, wherein the transfer device is an electrode assembly 1306 that attracts dielectric particles 1316 to its tip surface by imposing a non-uniform electric field near the particles. This phenomenon is scientifically referred to as dielectrophoresis and does not require particles to be charged in order to manipulate them. In dielectrophoresis, when the permittivity of a dielectric particle is greater than that of its surrounding medium, a non-uniform electric field causes uncharged dielectric particles to move towards regions of stronger electric field intensity, regardless of the polarity of the field.

There are various means by which a non-uniform electric field can be generated. Configurations suitable for use in the invention will be readily apparent to those of ordinary skill in the art. Examples of suitable configurations include, but are not limited to, concentric electrodes, parallel electrodes, and interdigitated electrodes. Increasing the number of electrodes or the perimeter of an electrode will tend to increase the amount of solid attached to it, since the electric field is usually greatest at the boundary or edge of an electrode.

Depending on the complex permittivity of the particles and the surrounding medium, the strength of the electric field necessary to attract and hold the particles will also depend on their size and nature. However, electric fields used in typical embodiments of the invention range in strengths from about $10^5$ V/m to about $10^8$ V/m, from about $10^6$ V/m to about $10^7$ V/m, or from about $2 \times 10^6$ V/m to about $5 \times 10^6$ V/m. Specific transfer devices and methods of their manufacture and use that may be used in methods and devices of the invention are disclosed in U.S. patent application Ser. No. 09/976,835, filed Oct. 12, 2001, the entirety of which is incorporated herein by reference.

In the particular embodiment shown in FIG. 42, an assembly 1306 of two concentric metal electrodes (FHC Inc., Bowdoinham, Me., Part No. CBHFM75) is used as the transfer device. A high voltage power supply 1314 (Trek Inc., Medina, N.Y., Model No. 623B) applies positive voltage to the inner electrode while the outer electrode is grounded to create a non-uniform electric field at the tip of the assembly. The electrode assembly is supported by a fixture 1307 which is mounted to a set of x, y, and z linear actuators. The actuators manipulate the electrode assembly toward a powder bed 1315 to extract a controlled amount of dielectric powder 1316.

Referring to FIG. 42, the mechanical response of the transfer device is generated using a thin piezoelectric ceramic actuator 1305 (Piezo Systems, Cambridge, Mass., Part No. T220/A4-203Y) affixed between the base of the electrode assembly and the fixture. A swept-sine voltage signal, 1 V peak-to-peak between 3.6 kHz and 4.0 kHz, is generated by a function generator 1308 (Model 33120A, Agilent, Palo Alto, Calif.) and applied to the piezoelectric actuator to excite the electrode assembly. The displacement on the electrode assembly in the direction perpendicular to its length is measured with a laser displacement sensor 1309 (Keyence Corp., Woodcliff Lake, N.J., Model No. LC2420A). Here, a small piece of specular material 1317 (3M Radiant mirror film) is epoxied on the tip of the transfer device to aid in the measurement.

Figure 43:
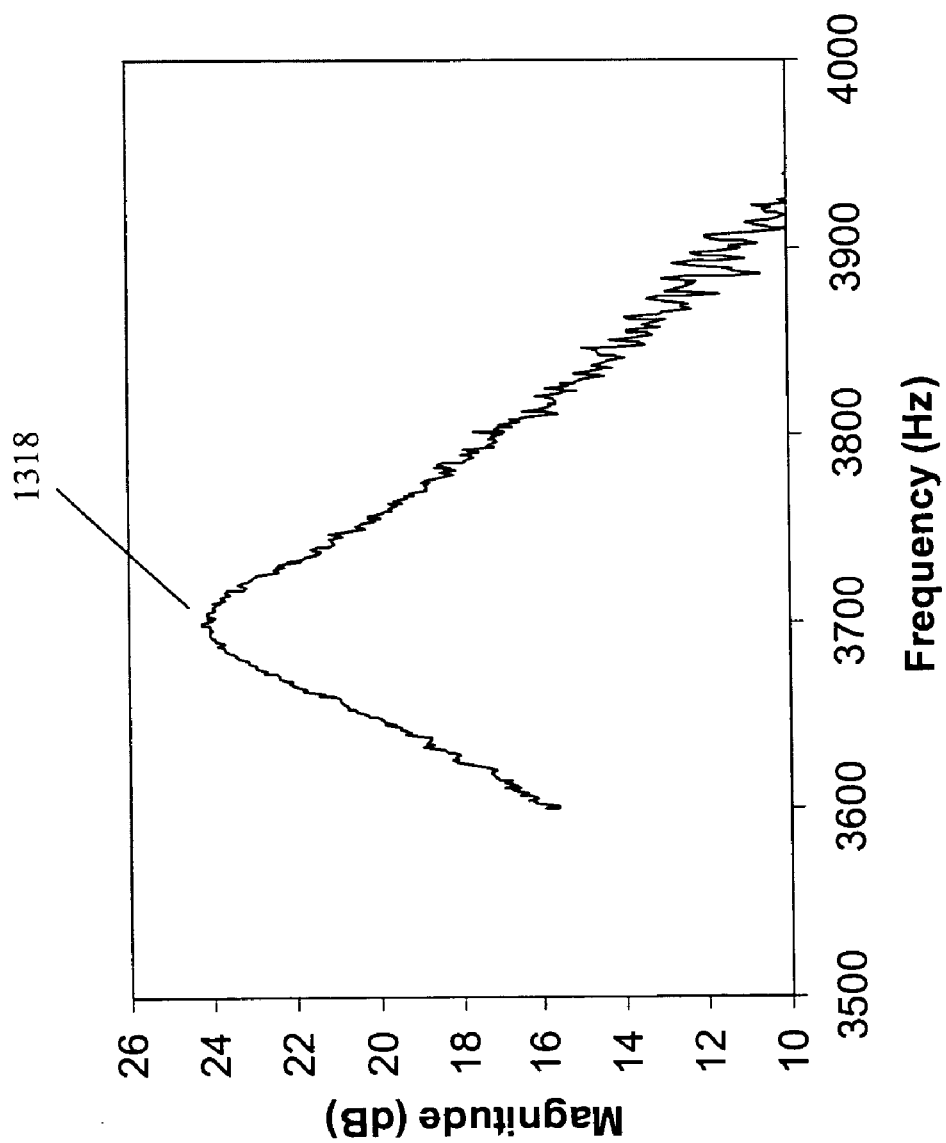
FIG. 43 illustrates a typical frequency spectrum of the mechanical response of an electrode assembly that is used to identify its resonant frequency.
Figure 44:
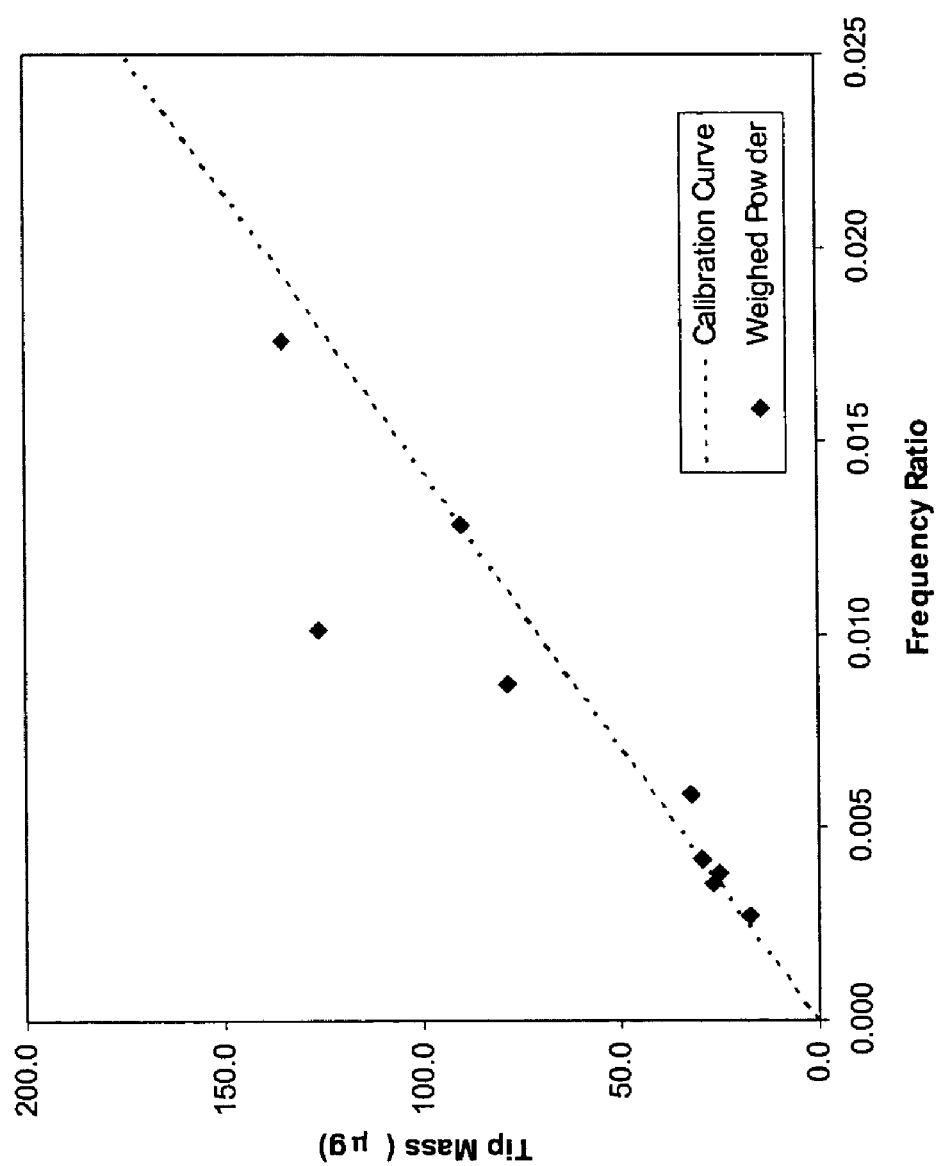
FIG. 44 illustrates a correlation between the measured frequency ratio and the amount of mass dispensed from an electrode assembly.

For each measurement, 10 consecutive frequency spectra are acquired using a commercial dynamic signal analyzer (Hewlett Packard, Model 35660A) and averaged linearly with 50% overlap to reduce spectral noise. FIG. 43 shows a typical frequency response of the electrode assembly. The peak 1318 in the spectrum indicates that the resonant frequency of the electrode assembly is about 3.7 kHz. In this embodiment, the relationship between the shift in resonant frequency and the amount of mass captured by the electrode assembly is determined by a calibration procedure. During calibration, the shift in resonant frequency is measured for several different samples whose masses are determined off-line by a conventional microbalance. For the system described in FIG. 42, linear regression by least-squares fitting was performed on the calibration data to determine the following correlation (3):

$$m = 6968 \times (f_o - f_m)/f_o - 0.0586 \qquad (3)$$

where m is the captured mass expressed in micrograms, and $f_o$ and $f_m$ are the resonant frequencies of electrode assembly expressed in Hertz, before and after the mass is captured, respectively. FIG. 44 illustrates good agreement between the calibration curve and experimental data from weighed quantities of pharmaceutical powder, such as aspirin and avicel, ranging from 17 micrograms to 90 micrograms.

While the invention has been described with respect to particular embodiments, it will be apparent to those skilled in the art that various changes and modifications may be made without departing from the spirit and scope of the invention as recited by the appended claims.

What is claimed is:

1. A method for dispensing a controlled mass of a solid, which comprises:
    (a) processing the solid into a powder with an average particle size of less than about 200 micrometers;
    (b) forming a powder bed with a predetermined mass and uniform height from a portion of the powder;
    (c) providing a grille plate with an array of holes sized so that a tube can pass through each with a small clearance;
    (d) holding the grille plate on top of the powder bed;
    (e) inserting a tube through a hole of the grille plate a controlled distance into the powder bed to obtain a plug of powder, wherein the tube has an interior that accommodates a means for ejecting materials from within the tube;
    (f) lifting the tube from the powder bed;
    (g) moving the tube over a target location; and
    (h) ejecting a plug of powder onto target location.

2. A method for dispensing a controlled mass of a solid, which comprises:
    (a) processing the solid into a powder with an average particle size of less than about 200 micrometers;
    (b) providing a source receptacle assembly comprising:
        (1) a source receptacle with sides, a top face, a bottom face, and at least one cylindrical hole that passes through and is perpendicular to the bottom face; and
        (2) a base plate that is removeably attached to the bottom face;
    (c) dispensing a predetermined mass of the powder into the cylindrical hole;
    (d) providing a cylindrical pin with at least one flat, perpendicular end face;
    (e) inserting the cylindrical pin into the cylindrical hole and pressing the pin into the powder with a predetermined force;
    (f) rotating the cylindrical pin through an angle of at least 1 degree of rotation with the predetermined force applied;
    (g) rotating and lifting the pin simultaneously out of the cylindrical hole;
    (h) inserting a tube a controlled distance into the powder to obtain a plug of powder, wherein the tube has an interior that accommodates a means for ejecting materials from within the tube;
    (i) lifting the tube from the powder bed;
    (j) moving the tube over a target location; and
    (k) ejecting a plug of powder onto target location.

3. A method for dispensing a controlled mass of a solid, which comprises:
    (a) processing the solid into a powder with an average particle size of less than about 200 micrometers;
    (b) providing a source receptacle assembly comprising:
        (1) a source receptacle with sides, a top face, a bottom face, and at least one cylindrical hole that passes through and is perpendicular to the bottom face; and
        (2) a close fitting cylinder disposed inside of the cylindrical hole; and
        (3) a cylinder locking means which allows the close fitting cylinder to be either locked to or disengaged from the source receptacle;
    (c) dispensing a predetermined mass of the powder into the cylindrical hole through the top face of the source receptacle;
    (d) providing a slide plate with at least one flat face;
    (e) pressing the flat face of the slide plate against the top face of the source receptacle;
    (f) disengaging the cylinder locking means;
    (g) pressing the cylinder into the powder with a predetermined force;
    (h) rotating the cylinder through an angle of at least 1 degree of rotation with the predetermined force applied;
    (i) engaging the cylinder locking means;
    (j) sliding the slide plate off of the top face of the source receptacle;
    (k) inserting a tube a controlled distance into the powder to obtain a plug of powder, wherein the tube has an interior that accommodates a means for ejecting materials from within the tube;
    (l) lifting the tube from the powder bed;
    (m) moving the tube over a target location; and
    (n) ejecting a plug of powder onto target location.

* * * * *